United States Patent
Pimentel et al.

(10) Patent No.: US 9,956,292 B2
(45) Date of Patent: May 1, 2018

(54) ANTI-METHANOGENIC COMPOSITIONS AND USES THEREOF

(71) Applicants: Cedars-Sinai Medical Center, Los Angeles, CA (US); Synthetic Biologics, Inc., Rockville, MD (US)

(72) Inventors: Mark Pimentel, Los Angeles, CA (US); Ruchi Mathur, Los Angeles, CA (US); Steve Kanzer, Boca Raton, FL (US); Vince Wacher, Rockville, MD (US)

(73) Assignees: Cedars-Sinai Medical Center, Los Angeles, CA (US); Synthetic Biologics, Inc., Rockville, MD (US)

( * ) Notice: Subject to any disclaimer, the term of this patent is extended or adjusted under 35 U.S.C. 154(b) by 0 days. days.

(21) Appl. No.: 14/826,115

(22) Filed: Aug. 13, 2015

(65) Prior Publication Data

US 2016/0045604 A1   Feb. 18, 2016

Related U.S. Application Data

(60) Provisional application No. 62/036,948, filed on Aug. 13, 2014, provisional application No. 62/043,649, (Continued)

(51) Int. Cl.
*A61K 47/38* (2006.01)
*A61K 31/351* (2006.01)
(Continued)

(52) U.S. Cl.
CPC ............ *A61K 47/38* (2013.01); *A61K 9/2846* (2013.01); *A61K 9/2886* (2013.01);
(Continued)

(58) Field of Classification Search
CPC ...... A61K 31/351; A61K 47/02; A61K 47/12; A61K 47/32; A61K 47/38
See application file for complete search history.

(56) References Cited

U.S. PATENT DOCUMENTS

| 225,202 A | 3/1880 | Wylie |
| 5,232,946 A | 8/1993 | Hurnaus et al. |

(Continued)

FOREIGN PATENT DOCUMENTS

| AU | 2003273141 | 8/2009 |
| CA | 2486585 | 7/2012 |

(Continued)

OTHER PUBLICATIONS

Dob Son, C.L. et al., "The effect of oleic acid on the human ileal brake and its implications for small intestinal transit of tablet formulations," Pharm. Res. 16(1):92-96 (Jan. 1999).
(Continued)

*Primary Examiner* — San Ming R Hui
(74) *Attorney, Agent, or Firm* — Linda B. Huber; Nixon Peabody LLP

(57) ABSTRACT

The present invention relates to, in part, methods and compositions for the treatment of methanogen-associated disorders such as, for example, Irritable Bowel Syndrome (IBS). Particularly, modified-release formulations comprising at least one antimethanogenic statin are provided which release the antimethanogenic statin in the intestines.

22 Claims, 18 Drawing Sheets

Related U.S. Application Data filed on Aug. 29, 2014, provisional application No. 62/043,789, filed on Aug. 29, 2014, provisional application No. 62/141,355, filed on Apr. 1, 2015.

(51) Int. Cl.

| A61K 47/12 | (2006.01) |
|---|---|
| A61K 47/18 | (2017.01) |
| A61K 9/28 | (2006.01) |
| A61K 9/48 | (2006.01) |
| A61K 31/00 | (2006.01) |

(52) U.S. Cl.
CPC ............ *A61K 9/4808* (2013.01); *A61K 31/00* (2013.01); *A61K 31/351* (2013.01); *A61K 47/12* (2013.01); *A61K 47/183* (2013.01)

(56) References Cited

U.S. PATENT DOCUMENTS

| 5,447,850 | A | 9/1995 | McCann |
| 5,840,332 | A | 11/1998 | Lerner et al. |
| 5,889,038 | A | 3/1999 | Lencer et al. |
| 5,977,175 | A | 11/1999 | Lin |
| 5,985,907 | A | 11/1999 | Wolin et al. |
| 6,036,950 | A | 3/2000 | Baker et al. |
| 6,201,014 | B1 | 3/2001 | Gardiner |
| 6,299,774 | B1 | 10/2001 | Ainsworth et al. |
| 6,328,959 | B1 | 12/2001 | Kayar et al. |
| 6,368,591 | B1 | 4/2002 | Chen et al. |
| 6,495,567 | B1 | 12/2002 | Lencer et al. |
| 6,558,708 | B1 | 5/2003 | Lin |
| 6,562,629 | B1 | 5/2003 | Lin et al. |
| 6,805,852 | B2 | 10/2004 | Lin et al. |
| 6,861,053 | B1 | 3/2005 | Lin et al. |
| 9,066,962 | B2 | 6/2015 | Pimentel et al. |
| 9,192,618 | B2 | 11/2015 | Pimentel et al. |
| 9,289,418 | B2 | 3/2016 | Pimentel et al. |
| 9,358,245 | B2 | 6/2016 | Pimentel et al. |
| 9,744,208 | B2 | 8/2017 | Pimentel et al. |
| 2002/0028269 | A1 | 3/2002 | Verrips |
| 2002/0039599 | A1 | 4/2002 | Lin et al. |
| 2006/0057197 | A1* | 3/2006 | Han ................... A61K 9/1652 424/468 |
| 2006/0246045 | A1 | 11/2006 | Pimentel et al. |
| 2007/0280949 | A1 | 12/2007 | Alfa |
| 2008/0182291 | A1 | 7/2008 | Pimentel et al. |
| 2009/0233888 | A1 | 9/2009 | Lin |
| 2009/0246177 | A1 | 10/2009 | Horn et al. |
| 2010/0048595 | A1 | 2/2010 | Gordon et al. |
| 2010/0055173 | A1 | 3/2010 | Penhasi et al. |
| 2010/0172874 | A1 | 7/2010 | Turnbaugh et al. |
| 2010/0184624 | A1 | 7/2010 | Samuel et al. |
| 2012/0219527 | A1 | 8/2012 | Perdok et al. |
| 2014/0228431 | A1 | 8/2014 | Pimentel et al. |
| 2014/0271561 | A1 | 9/2014 | Pimentel et al. |
| 2016/0038562 | A1 | 2/2016 | Pimentel et al. |
| 2016/0244813 | A1 | 8/2016 | Pimentel et al. |

FOREIGN PATENT DOCUMENTS

| CN | 103142552 A | 6/2013 |
| CN | 105208861 A | 12/2015 |
| EP | 1 609 852 A1 | 12/2005 |
| EP | 2 251 017 | 11/2010 |
| EP | 1 505 989 | 2/2011 |
| EP | 2967060 A2 | 1/2016 |
| GB | 423083 A | 1/1935 |
| GB | 2 338 244 A | 12/1999 |
| JP | 60-133852 | 7/1985 |
| JP | 03-275630 | 12/1991 |
| JP | 08-310960 | 11/1996 |
| JP | 2005-526861 | 9/2005 |
| JP | 2016-516717 A | 6/2016 |
| WO | WO 2001/011077 | 2/2001 |
| WO | WO 2001/032162 | 5/2001 |
| WO | WO 2001/034123 | 5/2001 |
| WO | WO 2003/100023 | 12/2003 |
| WO | WO 2004/021972 | 3/2004 |
| WO | 2005/058861 A1 | 6/2005 |
| WO | WO 2005/115380 | 12/2005 |
| WO | 2006102350 A1 | 9/2006 |
| WO | WO2008/044236 * | 4/2008 |
| WO | 2010/088633 A1 | 8/2010 |
| WO | 2011103123 A2 | 8/2011 |
| WO | WO2012124973 * | 9/2012 |
| WO | WO 2014/152754 | 12/2014 |
| WO | 2016/025762 A1 | 2/2016 |
| WO | 2016161085 A1 | 10/2016 |

OTHER PUBLICATIONS

Lin, H.C. et al., "Intestinal transit is more potently inhibited by fat in the distal (ileal brake) than in the proximal (jejunal brake) gut," Dig. Dis. Sci. 42(1):19-25 (Jan. 1997)

Lin, H.C. et al., "Jejunal brake: inhibition of intestinal transit by fat in the proximal small intestine," Dig. Dis. Sci., 41(2):326-29 (Feb. 1996).

Naidu, A.S., et al., "Probiotic spectra of lactic acid bacteria," Crit. Rev. Food Sci. Nutr. 38(1):13-126 (Jan. 1999).

Vanderhoof, J.A., et al., "Use of probiotics in childhood gastrointestinal disorders," J Pediatr Gastroenterol Nutr. 27(3):323-32 (Sep. 1998).

Tannock, G. W, "Probiotic properties of lactic acid bacteria: plenty of scope for R & D," Trends Biotechnol. 15(7):270-74 (Jul. 1997).

Salminen, S., et al., "Clinical uses of probiotics for stabilizing the gut mucosal barrier: successful strains and future challenges," Antonie Van Leeuwenhoek. 70(2-4):347-58 [1997] (Oct. 1996) (Review).

Chaucheryras F. et al., "In vitro $H_2$ utilization by ruminal acetogenic bacterium cultivated alone or in association with an archaea methanogen is stimulated by a probiotic strain of *Saccharomyces cerevisiae*," Appl Environ Microbiol 61(9):3466-7 (Sep. 1995).

Kontula, P., et al., "The effect of lactose derivatives on intestinal lactic acid bacteria," J. Dairy Sci. 82(2):249-56 (Feb. 1999).

Alander M., et al., "The effect of probiotic strains on the microbiota of the Simulator of the Human Intestinal Microbial Ecosystem (SHIME)," Int. J. Food Microbiol. 46(1):71-79 (Jan. 1999).

Spanhaak S., et al., "The effect of consumption of milk fermented by Lactobacillus casei strain Shirota on the intestinal microflora and immune parameters in humans," Eur. J. Clin. Nutr. 52(12):899-907 (Dec. 1998).

Charteris W.P., et al., "Antibiotic susceptibility of potentially probiotic *Lactobacillus* species," J. Food Prot. 61(12):1636-43 (Dec. 1998).

Wolf, B.W. et al., "Safety and tolerance of Lactobacillus reuteri supplementation to a population infected with the human immunodeficiency virus," Food Chem. Toxicol. 36(12):1085-94 (Dec. 1998).

Gardiner, G., et al., "Development of a probiotic cheddar cheese containing human-derived Lactobacillus paracasei strains," Appl. Environ. Microbiol. 64(6):2192-99 (Jun. 1998).

Sameshima, T., et al., "Effect of intestinal Lactobacillus starter cultures on the behaviour of *Staphylococcus aureus* in fermented sausage," Int. J. Food Microbiol. 41(1):1-7 (May 1998).

Tuohy, K.M., et al., "The prebiotic effects of biscuits containing partially hydrolysed guar gum and fucto-oligosaccharides—a human volunteer study", Br J Nutr 86(3):341-8 (Sep. 2001).

McKay, L.F., et al., "Methane and hydrogen production by human intestinal anaerobic bacteria," Acta Pathol Microbiol Immunol Scand [B]. 90(3):257-60 (Jun. 1982).

Kerlin, P., et al., "Breath hydrogen testing in bacterial overgrowth of the small intestine," Gastroenterology. 95(4):982-88 (Oct. 1988).

Strocchi, A., et al., "Detection of malabsorption of low doses of carbohydrate: accuracy of various breath H2 criteria," Gastroenterology 105(5):1404-10 (Nov. 1993).

(56) References Cited

OTHER PUBLICATIONS

De Boissieu, D., et al., "Small-Bowel bacterial overgrowth in children with chronic diarrhea, abdominal pain, or both," J Pediatr. 128(2):203-7 (Feb. 1996).
Lewindon, P.J., et al., "Bowel dysfunction in cystic fibrosis: importance of breath testing," J. Pediatr. Child Health 34(1):79-82 (Feb. 1998).
Corazza, G., et al., "Prevalence and consistency of low breath H2 excretion following lactulose ingestion. Possible implications for the clinical use of the H2 breath test," Dig. Dis. Sci. 38(11):2010-16 (Nov. 1993).
Riordan, S. M., et al., "The lactulose breath hydrogen test and small intestinal bacterial overgrowth," Am. J. Gastroentrol. 91(9):1795-1803 (Sep. 1996).
Swart, G.R., et al., "$^{13}$C breath test in gastrointestinal practice," Scand. J. Gastroenterol. Suppl. 225:13-18 (1998).
Dellert, S.F., et al., "The $^{13}$C-xylose breath test for the diagnosis of small bowel bacterial overgrowth in children," J. Pediatr. Gastroenterol. Nutr. 25(2):153-58 (Aug. 1997).
King, C.E., et al., "Breath tests in the diagnosis of small intestinal bacterial overgrowth," Crit. Rev. Lab. Sci. 21(3):269-81 (1984).
Chang, C. S., et al., "Increased accuracy of the carbon-14 D-xylose breath test in detecting small-intestinal bacterial overgrowth by correction with the gastric emptying rate," Eur. J. Nucl. Med. 22(10):1118-22 (Oct. 1995).
King, C.E., et al., "Comparison of the 1-gram [14C]xylose, 10-gram lactulose-H2, and 80 gram glucose-H2 breath tests in patients with small intestine bacterial overgrowth," Gastroenterology 91(6):1447-51 (Dec. 1986).
Schneider, A., et al., "Value of the 14C-D-xylose breath test in patients with intestinal bacterial overgrowth," Digestion 32(2):86-91 (1985).
Drossman, D. A., et al, "Bowel patterns among subjects not seeking health care. Use of a questionnaire to identify a population with bowel dysfunction," Gastroenterology. 83(3):529-34 (Sep. 1982).
Thompson, W.G., et al., "Functional bowel disorders in apparently healthy people." Gastroenterology. 79(2):283-8 (Aug. 1980).
Kumar, D., et al., "The irritable bowel syndrome: a paroxysmal motor disorder," Lancet. 2(8462):973-77 (Nov. 1985).
Grundy, D., "Mechanisms for the symptoms of irritable bowel disease—possible role of vagal afferents," In, Neurogastroenterology from the Basics to the Clinics. H-J Drammer and MV Singer, Editors, Klumer Academic Publishers, Boston, 2000, pp. 659-663.
Silverman, D..S., et al., "Regional cerebral activity in normal and pathological perception of visceral pain," Gastroenterology. 112(1):64-72 (Jan. 1997).
Whitehead, W.E., et al., "Effects of stressful life events on bowel symptoms: Subjects with irritable bowel syndrome compared with subjects without bowel dysfunction," Gut 33(6):825-30 (Jun. 1992).
Thompson, W.G., et al., "Functional bowel disorders and functional abdominal pain. Rome II: A multinational consensus document on functional gastrointestinal disorders," Gut 45 Suppl. 2:II43-47 (Sep. 1999).
Kruis, W., et al., "A diagnostic score for the irritable bowel syndrome," Gastroenterology. 87(1):1-7 (Jul. 1984).
Sullivan, S.N., "A prospective study of unexplained visible abdominal bloating," N Z Med J. 107(988):428-30 (Oct. 1994).
Koide, A., et al., "Quantitative analysis of bowel gas using plain abdominal radiograph in patients with irritable bowel syndrome," Am J Gastroenterol, 92(7):1735-41 (Jul. 2000)
Pimentel, M., et al., "Eradication of small intestinal bacterial overgrowth reduces symptoms of irritable bowel syndrome," Am J Gastroenterol. 95(12):3503-6 (Dec. 2000).
Fiedorek, S.C., et al, "Breath methane production in children with constipation and encoparesis," J Pediatr Gastroenterol. 10(4):473-77 (May 1990).
Fass., R., et al., "Evidence and consensus-based practice guidelines for the diagnosis of irritable bowel syndrome," Arch Intern Med. 161(17):2081-88 (Sep. 2001).

Veldhuyzen Van Zanten, S.J., et al., "Design of treatment trials for functional gastrointestinal disorders," Gut. 45 Suppl II:II69-77 (Sep. 1999).
Whitehead, W.E., et al., "Definition of a responder in clinical trials for functional gastrointestinal disorders: reports on a symposium," Gut. 45 Suppl 2:II78-9 (Sep. 1999).
Camilleri, M., et al., "Efficacy and safety of alosetron in women with irritable bowel syndrome: a randomised, placebo-controlled trial," Lancet. 355(9209):1035-40 (Mar. 2000).
Bond, J.H. Jr., et al., "Investigation of small bowel transit time in man utilizing pulmonary hydrogen (H2) measurements," J Lab Clin Med. 85(4):546-555 (Apr. 1975)
Joseph, F. Jr., et al, "Breath testing: diseased versus normal patients," J Pediatr Gastroenterol. 7(5):787-8 (Sep.-Oct. 1988).
Galatola, G., et al., "Diagnosis of bacterial contaminationof the small intestine using the 1g [14C] xylose breath test in various gastrointestinal diseases," Menerva Gastroenterologic Dietologica 37(3):169-75 (Jul.-Sep. 1991) (Abstract in English).
Nayak, A., et al., "Metronidazole relieves symptoms in irritable bowel syndrome: the confusion with so-called 'chronic amebiasis'," Indian J Gastroenterol 16(4):137-39 (Oct. 1997).
King, T.S., et al., "Abnormal colonic fermentation in irritable bowel syndrome," Lancet 352(9135):1187-89 (Oct. 1998).
Neal, K.R., et l., "Prevalence of gastrointestinal symptoms six months after bacterial gastroenteritis and risk facts for development of the irritable bowel syndrome: postal survey of patients," BMJ 314(7083):779-82 (Mar. 1997).
Collins, S.M., et al., "Stress, inflammation and the irritable bowe syndrome," Canadian Journal of Gastroenterology. 13 Suppl:47A-49A (Mar. 1999).
Weaver, G.A., et al., "Incidence of methanogenic bacteria in a sigmoidoscopy population: an association of methanogenic bacteria and diverticulosis," Gut. 27(6):698-704 (Jun. 1986).
Bjorneklett, A., et al., "Bacterial overgrowth in jejunal and ileal disease," Scand J Gastroenterol. 18(2):289-98 (Mar. 1983).
McKay, L.F., et al., "Methane excretion in man—a study of breath, flatus and faeces," Gut 26(1):69-74 (Jan. 1983).
Castiglione, F., et al. "Orocecal transit time and bacterial overgrowth in patients with Crohn's disease," J Clin Gastroenterol. 31(1):63-66 (Jul. 2000).
Bentley, D.W., et al., "The microflora of the human ileum and intrabdominal colon: results of direct needle aspiration at surgery and evaluation of the technique," J Lab Clin Med. 79(3):421-9 (Mar. 1972).
Gorbach, S.L., "Intestinal Microflora," Gastroenterology. 60(6):1110-29 (Jun. 1971).
Nichols, R.L., et al., "Ileal microflora in surgical patients," J Urol 105(3):351-3 (Mar. 1971).
Plaut, A.G., et al, "Studies of intestinal microflora. 3. The microbial flora of human small intestinal mucosa and fluids," Gastroenterology 53(6):868-73 (Dec. 1967).
Cann, P.A., et al., "Irritable bowel syndrome: relationship of disorders in the transit of a single solid meal to symptom patterns," Gut 24(5):405-11 (May 1983).
Read, N.W., et al., "Simultaneous measurement of gastric emptying, small bowel residence and colonic filling of a solid meal by the use of the gamma camera," Gut. 27(3):300-8 (Mar. 1986).
Hutchinson, R., et al., "Scintigraphic measurement of ieocaecal transit in irritable bowel syndrome and chronic idiopathic constipation," Gut 36(4):585-9 (Apr. 1995).
Rhodes, J.M., et al., "The lactulose hydrogen breath test as a diagnostic test for small bowel bacterial overgrowth," Scand J Gastroenterol. 14(3):333-6 (1979).
Rutgeerts, P., et al., "Ileal dysfunction and bacterial overgrowth in patients with Crohn's disease," European J Clin Invest. 11(3):199-206 (Jun. 1981).
Funayama, Y., et al., "Monitoring and antibacterial treatment for postoperative bacterial overgrowth in Crohn's disease," Dis Colon Rectum. 42(8):1072-7 (Aug. 1999).
Peled, Y., et al., "Factors affecting methane production in humans. Gastrointestinal diseases and alterations of colonic flora," Dig Dis Scr. 32(3):267-71 (Mar. 1987).

(56) References Cited

OTHER PUBLICATIONS

Melcher, E.A., et al., "Methane production and bowel function parameters in healthy subjects on low-and high fiber diets," Nutrition and Cancer. 16(2):85-92 (1991).
Levitt, M.D., et al., "Hydrogen and methane production in man," Ann NY Acad Sci. 150(1):75-81 (Feb. 1968).
Engels et al., Symptomless Colonisation By Clostridium Difficile and Risk of Diarrhoea, The Lancet, (Jun. 6, 1998), p. 1733, 351:9117, London, Great Britain.
Nguyen et al., Diarrhea Caused By Enterotoxigenic Bacteroides Fragilis In Children Less Than 5 Years Of Age In Hanoi, Vietnam, Anaerobe, (Feb. 2005), pp. 109-114, 11:1-2, London, Great Britain.
Kehrer et al. Modulation of Irinotecan-Induced Diarrhea By Cotreatment With Neomycin In Cancer Patients. Clinical Cancer Research, May 2001, 7(1), pp. 1136-1141.
Black et al., An Overview Of The Clinical Safety Profile Of Atorvastatin (Lipitor), A New HMG-CoA Reductase Inhibitor, Archives of Internal Medicine, (Mar. 23, 1998), 158(6):577-584.
Bakker-Arkema et al., Safety Profile Of Atorvastatin-Treated Patients With Low LDL-Cholesterol Levels, Atherosclerosis, (2000), 149(1): 123-129.
The Merck Index (11th Edition), (1989), Entry 5225, p. 844.
Hoeg et al., Effects Of Combination Cholestyramine-Neomycin Treatment On Plasma Lipoprotein Concentrations In Type II Hyperlipoproteinemia, American Journal of Cardiology, May 1, 1985; 55(11):1282-1286.
Hoshimo et al., Maldigestion/Malabsorption In The Various Gastrointestinal And Liver Diseases. Results Of Breath Hydrogen And Methane Analysis, Digestion & Absorption, (1998), 21(1):55-60.
Soares et al. "Metano no ar Expirado de Criancas com Constipacao Cronica Funcional," Arq. Gastroenterol., vol. 39, No. 1, Jan./Mar. 2002; pp. 66-72.
Soares et al. "Breath methane associated with slow colonic transit time in children with chronic constipation," J. Clin. Gastroenterol. Jul. 2005; vol. 39, No. 6, pp. 512-515.
Chatterjee et al. "The degree of breath methane production in IBS correlates with the severity of constipation," Am. J. Gastroenterology 2007; 102: 837-841.
Novick et al. "A randomized, double-blind, placebo-controlled trial of tegaserod in female patients suffering from irritable bowel syndrome with constipation," Aliment. Pharmacol. Ther. 2002; 16: 1877-1888.
Pimentel et al. "Methane, a gas produced by enteric bacteria, slows intestinal transit and augments small intestinal contractile activity," Am. J. Physiol. Gastrointest. Liver Physiol. 2006; 290: G1089-G1095.
Pimentel et al. "Neomycin improves constipation-predominant irritable bowel syndrome in a fashion that is dependent on the presence of methane gas: Subanalysis of a double-blind randomized controlled study," Dig. Dis. Science 2006; 51: 1297-1301.
Olesen et al. "Efficacy, safety, and tolerability of fructooligosaccharides in the treatment of irritable bowel syndrome," Am. J. Clin. Nutr. 2000; 72: 1570-1575.
Niedzielin et al. "A controlled, double-blind, randomized study on the efficacy of Lactobacillus plantarum 299V in patients with irritable bowel syndrome," Euro. J. of Gastroenterology & Hepatology: Oct. 2001, vol. 13, Issue 10, pp. 1143-1147.
Nobaek, et al. "Alteration of intestinal microflora is associated with reduction in abdominal bloating and pain in patients with irritable bowel syndrome," Am. J. Gastroenterology (2000) 95, 1231-1238.
Thompson, W. Grant. "Probiotics for irritable bowel syndrome: a light in the darkness?" Euro. J. of Gastroenterology & Hepatology: Oct. 2001, vol. 13, Issue 10, pp. 1135-1136.
Basseri et al. Intestinal Methane Production in Obese Individuals Is Associated with a Higher Body Mass Index. Gastroenterology & Hepatology 2012; 8(1): 22-28.
Kim et al. Methanobrevibacter smithii Is the Predominant Methanogen in Patients with Constipation-Predominant IBS and Methane on Breath. Digestive Diseases and Sciences 2012; 57(12): 3213-3218.
Mathur et al. Intestinal *Methanobrevibacter smithii* but Not Total Bacteria is Related to Diet-Induced Weight Gain in Rats. Obesity Journal 2013; 21(4):748-754.
Kunkel et al. Methane on Breath Testing is Associated with Constipation: A systematic review and Meta-analysis. Dig Dis Sci (2011). 56(6): 1612-1618.
Hwang et al. Evaluating Breath Methane as a Diagnostic Test for Constipation-Predominant IBS. Dig Dis Sci (2010). 55(2): 398-403.
PCT/US2015/045140 International Search Report and Written Opinion dated Nov. 19, 2015.
PCT/US03/16656 International Search Report dated Dec. 18, 2003; 2 pages.
PCT/US03/16656 International Preliminary Examination Report dated Jun. 14, 2004); 4 pages.
EP 03741819.1 Supplemental Search Report dated Apr. 5, 2007.
EP 10173966.2 Supplemental Search Report dated Sep. 30, 2010.
EP 10173966.2 European Extended Search Report dated Oct. 14, 2010.
Ghoshal et al. Irritable bowel syndrome and small intestinal bacterial overgrowth: Meaningful association or unnecessary hype. World Journal of Gastroenterology (2014). 20(10)2482-2491.
PCT/US2014/027697 International Search Report and Written Opinion dated Oct. 3, 2014; 9 pages.
PCT/US2016/025214 International Search Report and Written Opinion dated Jun. 2, 2016; 13 pages.
EP Application No. 14770590.9 Extended Search Report dated Oct. 26, 2016; 11 pages.
Kang et al. Anti-Obesity Drugs: A Review about Their Effects and Safety. Diabetes Metab J (2012). 36:13-25.
Low et al. A Combination of Rifaxamin and Neomycin Is Most Effective in Treating Irritable Bowel Syndrome Patients with Methane on Lactulose Breath Test. J Clin Gastroenterol (2010). 44:547-550.
Miller et al. Inhibition of Growth of Methane-Producing Bacteria of the Ruminant Forestomach by Hydroxymethylglutaryl-SCoA Reductase Inhibitors. J Dairy Sci (2001). 84:1445-1448.
Quigley et al. Small Intestinal Bacterial Overgrowth: Roles of Antibiotics, Prebiotics, and Probiotics. Gastroenterology (2006). 130:S78-S90.
Rooks et al. Su1940: Methanobrevibacter Smithii is Highly Prominent in the Small Bowel of Rats. Gastroenterology—Proceedings from Digestive Disease Week (2012). 142(5): Suppl 1, p. S-541. Abstract Only.
Rumessen et al. Carbohydrate Malabsorption: Quantification by Methane and Hydrogen Breath Tests. Scandinavian Journal of Gastroenterology (1994). 29:826-832.
Zhang et al. Human gut microbiota in obesity and after gastric bypass. PNAS (2008). pp. 1-6.
EP 15831885.7 Extended Search Report dated Dec. 13, 2017, 18 Pages.
Evonik Industries, Eudragit, 2015, 16 Pages, Retrieved from the internet: http://eudragit.evonik.com/sites/lists/HN/Documents/evonik-brochure-eudragit-EN.pdf on Jul. 13, 2016.

* cited by examiner

ANTI-METHANOGENIC COMPOSITIONS AND USES THEREOF

CROSS-REFERENCE TO RELATED APPLICATIONS

This application claims the benefit of U.S. Provisional Patent Application Nos. 62/036,948, filed Aug. 13, 2014; 62/043,649, filed Aug. 29, 2014; 62/043,789, filed Aug. 29, 2014; and 62/141,355, filed Apr. 1, 2015, the entire contents of which are herein incorporated by reference.

FIELD OF THE INVENTION

The present invention relates to, in part, methods and compositions for the treatment of methanogen-associated disorders such as, for example, Irritable Bowel Syndrome (IBS).

BACKGROUND

The human microbiome plays an important role in both health and disease. While the majority of microorganisms inhabiting the gastrointestinal system of humans and animals have a beneficiary role in, for example, aiding digestion of important nutrients, it is known that a minority of otherwise previously considered "commensal" organisms play a role in the pathogenesis of various diseases.

Irritable Bowel Syndrome (IBS) affects an estimated 30 million people in the United States alone. IBS is a functional gastrointestinal (GI) disorder that results in abdominal pain and/or discomfort, along with changes in bowel habits. IBS is classified into four subtypes based on a person's stool consistency: constipation-associated IBS (IBS-C); diarrhea-associated IBS (IBS-D); mixed (or alternating) IBS (IBS-M or IBS-A); and unsubtyped (or unspecified) IBS (IBS-U).

Recent studies have suggested that certain methane producing microorganisms inhabiting the gut known as methanogens may play a causative role in constipation. Specifically, studies suggest a link between intestinal methane ($CH_4$) production and constipation in IBS-C as well as chronic idiopathic constipation (CIC). Methane ($CH_4$) production in humans is due to methanogenic archaea in the intestine. These organisms serve a critical biological function by removing the by-products of bacterial fermentation of polysaccharides, notably hydrogen gas ($H_2$) and short-chain fatty acids (SCFAs). The dominant methanogen inhabiting the human gut is the archaea, *Methanobrevibacter smithii* (*M. smithii*). In vitro susceptibility testing has demonstrated that methanogens such as *M. smithii* are highly resistant to most classes of antibiotics. Further, complete eradication of intestinal methanogens via a single course of therapy is unlikely using broad spectrum antibiotics, leading to methanogen recolonization and methanogenesis returning to pathogenic levels. Continuous use of antibiotics is associated with various side effects and increased risk of developing antibiotic resistance. Further still, long-term use of antibiotics may disrupt the otherwise potentially beneficial bacterial intestinal microbiome and gastrointestinal flora.

There remains a need for safe and effective approaches for the long term suppression of enteric methanogenesis and/or excessive methane production in the treatment of diseases such as IBS.

SUMMARY OF THE INVENTION

Accordingly, the present invention provides, inter alia, improved methods and formulations for the treatment of various methanogen-associated disorders. In one aspect, the present invention relates to compositions and uses of modified-release formulations which comprise at least one anti-methanogenic agent, including, for example, statin hydroxy-acid molecules that, without wishing to be bound by theory, are typically effective inhibitors of 3-hydroxy-3-methyl-glutaryl-coenzyme A (HMG-CoA) reductase and statin lactones that, without wishing to be bound by theory, are typically ineffective HMG-CoA reductase inhibitors (collectively "antimethanogenic statins"). In various embodiments, the formulations and methods described herein eradicate or reduce methane production, which is causative of, or correlative with, various methanogen-associated disorders, including, for example, IBS (e.g. IBS-C), diabetes and obesity. In various embodiments, the formulations and methods described herein target the gastrointestinal (GI) tract and therefore provide for specific delivery to a site of methanogen colonization and/or methane production and/or accumulation while avoiding or reducing systemic exposure to antimethanogenic statins and minimizing their systemic effects. As such, the present invention provides for effective treatments that avoid side effects associated with chronic systemic statin administration (e.g. muscle pain, abnormalities in liver enzyme tests, etc.). Further, in some embodiments, the present invention surprisingly treats bowel-disorders despite reports linking statin use to, for example, constipation (see, e.g., Fernandes et al. Possible association between statin use and bowel dysmotility. *BMJ Case Reports* 2012; 10.1136/bcr.10.2011.4918 and Merck Global Medical Information. Professional Information Response UK11-010274, the contents of which are hereby incorporated by reference in their entireties). Further, in some embodiments, the present invention surprisingly treats diabetes despite reports linking statin use to this disorder (see, e.g. Naci et al., Comparative tolerability and harms of individual statins: a study-level network meta-analysis of 246 955 participants from 135 randomized, controlled trials. *Circ Cardiovasc Qual Outcomes* 6 (4): 390-9, the contents of which are hereby incorporated by reference in their entirety).

In some embodiments, the modified-release formulations release at least 60% of the anti-methanogenic agent, such as anti-methanogenic statins, after the stomach and into one or more regions of the intestinal tract. In certain embodiments, the formulation releases the antimethanogenic statin in the small intestine, including one or more of the duodenum, jejunum, and ileum. In other embodiments, the formulation releases the anti-methanogenic statin in the large intestine (e.g., one or more of the cecum, ascending, transverse, descending or sigmoid portions of the colon, and rectum).

In various embodiments, the antimethanogenic statin is selected from atorvastatin, cerivastatin, dalvastatin, eptastatin, fluindostatin, fluvastatin, lovastatin, mevastatin, pitavastatin, pravastatin, rosuvastatin, simvastatin, velostatin, and pharmaceutically acceptable salts, stereoisomers, or prodrug derivatives thereof. In some embodiments, the anti-methanogenic statin is selected from lovastatin, pravastatin, and simvastatin. In one embodiment, the statin is pravastatin and pharmaceutically acceptable salts, stereoisomers, or prodrug derivatives thereof. In another embodiment, the antimethanogenic statin is lovastatin and pharmaceutically acceptable salts, stereoisomers, or prodrug derivatives thereof. In one embodiment, the antimethanogenic statin is simvastatin and pharmaceutically acceptable salts, stereoisomers, or prodrug derivatives thereof. In some embodiments, the antimethogenic statin is in either the lactone or ß-hydroxyacid form. In some embodiments, the antimethanogenic statin is the lactone form of lovastatin.

In various embodiments, the modified-release formulation is administered orally to a subject in need thereof. In one embodiment, the formulation may be in the form of a capsule or a tablet. In an embodiment, the formulation comprises a modified-release coating that is substantially stable in gastric fluid. In another embodiment, the modified-release coating may be degraded by a microbial enzyme present in the gut flora. In a further embodiment, the modified-release coating may have a solubility and/or stability that is pH dependent. In other embodiments, the modified-release coating may have a time-dependent erosion profile.

In various embodiments, the modified-release formulation comprises a first dose of at least one anti-methanogenic statin and a second dose of at least one antimethanogenic statin (e.g. the first and second doses may be the same or different antimethanogenic statin at a given dose, or the first and second doses may be the same antimethanogenic statin at the same or different doses). In various embodiments, the first dose and the second dose are released at different times and/or at different pHs and in different regions of the gastrointestinal tract. In some embodiments, the first and/or second dose of at least one antimethanogenic statin is encapsulated in a core particle. A modified-release coating may be disposed over the core particle to form a modified-release particle. In certain embodiments, the formulation comprises a plurality of modified-release particles. In an illustrative embodiment, the formulation maybe in the form of a capsule. In another embodiment, the first and second dose of at least one antimethanogenic statin is encapsulated in a layer. A modified-release coating may be disposed over the layer to form a modified-release layer. In certain embodiments, the formulation comprises a plurality of modified-release layers. In an illustrative embodiment, the formulation maybe in the form of a multilayer tablet.

In some embodiments, the first dose and second dose of antimethanogenic statins are released at different times and or at different pHs. In illustrative embodiments, the first dose may release the antimethanogenic statin at the duodenum while the second dose may release the antimethanogenic statin at the ileum. In other embodiments, the first dose may release the antimethanogenic statin at the small intestine while the second dose may release the antimethanogenic statin at the large intestine.

The formulations of the present invention may further include a pharmaceutically acceptable excipient. In some embodiments, the formulation may further include an agent which prevents or reduces lactone ring-opening, such as an esterase inhibitor (e.g. grapefruit juice; including flavonoid components such as, for example, naringenin, kaempferol, morin, galangin, and quercetin; flavoring ester mixtures in, for example, strawberry juice (e.g. phenyl benzoate, propyl paraben, phenethyl isobutyrate, bacampicillin, talampicillin, p-tolyl benzoate, ethyl paraben, diethyl phthalate, octyl acetate, and pivampicillin) and/or a paraoxonase inhibitor (e.g. PON1 or PON3 inhibitor). In some embodiments, the formulation may further include an inhibitor of the organic anion transporting polypeptide (OATP) transporter, such as one or more of green tea extract, epicatechin gallate (ECG) and epigallocatechin gallate (EGCG). In some embodiments, the OATP inhibitor is released prior to release of the statin. The formulations of the present invention may also further include an additional therapeutic agent such as, by way of non-limiting example, a prokinetic agent.

In one aspect, the present invention provides for methods of inhibiting or reducing methanogenesis and/or methane accumulation by administering the formulations described herein to a subject in need thereof. In some embodiments, the subject suffers from IBS, such as IBS-C. In other embodiments, the subject suffers from obesity. In yet another embodiment, the subject suffers from diabetes. In various aspects, the present invention provides for methods of treating or preventing a methanogen-associated disorder optionally selected from one or more of IBS, such as IBS-C, diabetes, and obesity by administering the formulations described herein to a subject in need thereof.

In another aspect, the present invention also provides for methods of treating constipation by administering the formulations described herein to a subject in need thereof. A further aspect of the invention provides methods for treating (e.g. reducing or eliminating) enteric methane production by administering the formulations described herein to a subject in need thereof.

DESCRIPTION OF THE FIGURES

FIG. 9A shows an absolute change and FIG. 9B shows percentage change, from baseline in breath methane versus ALTOPREV dose (15, 30 or 60 mg q.d.). FIG. 9C shows an absolute change and FIG. 9D shows percentage change, from baseline in breath methane versus baseline breath methane (ppm) in patients treated with ALTOPREV (15, 30 or 60 mg q.d.).

DETAILED DESCRIPTION OF THE INVENTION

Figure 1A:
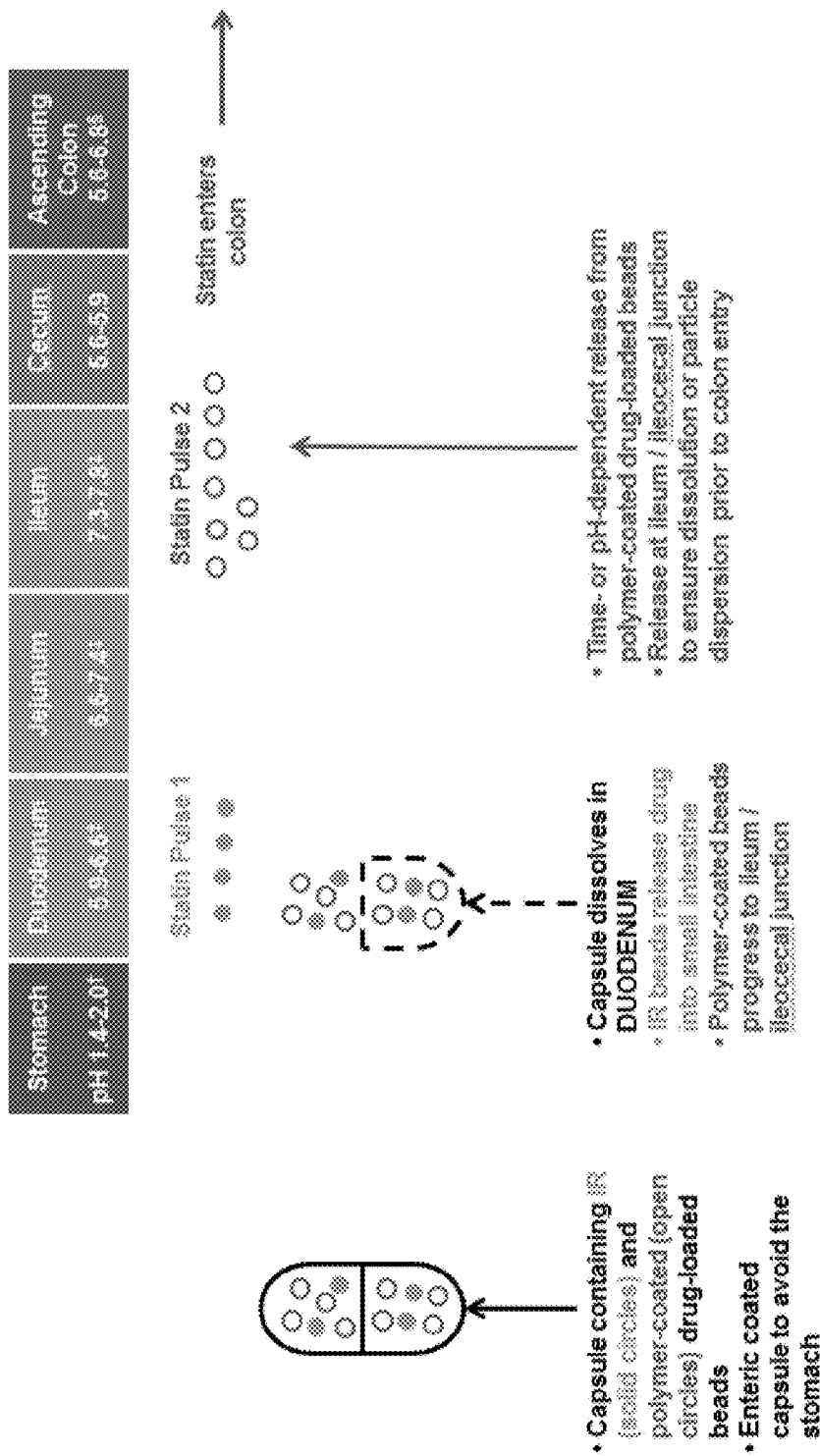
FIGS. 1A-1B depict some embodiments of a modified-release formulation in the form of encapsulated beads which releases a first statin dose at the duodenum and a second statin dose at the ileum.
Figure 1B:
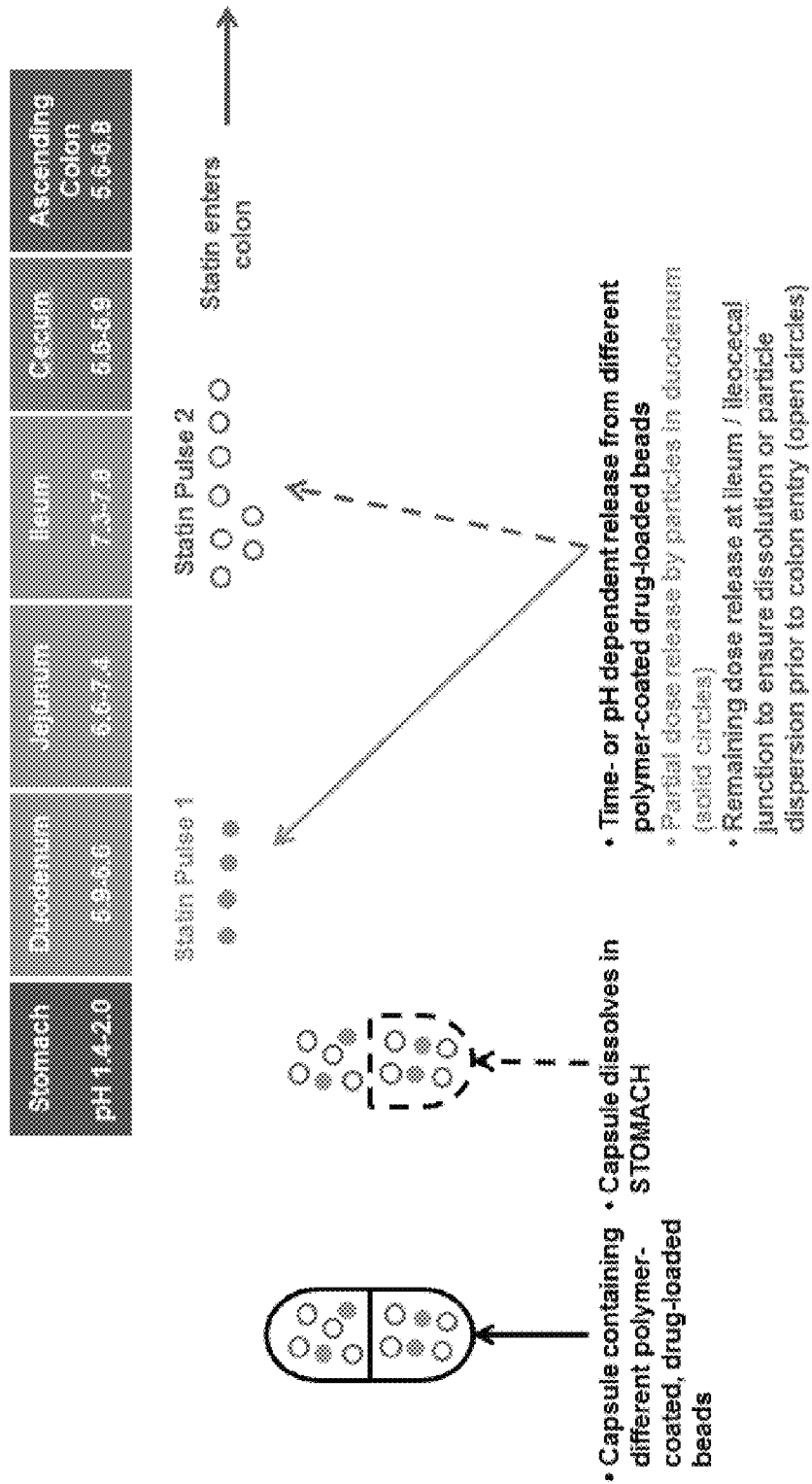
Figure 2:
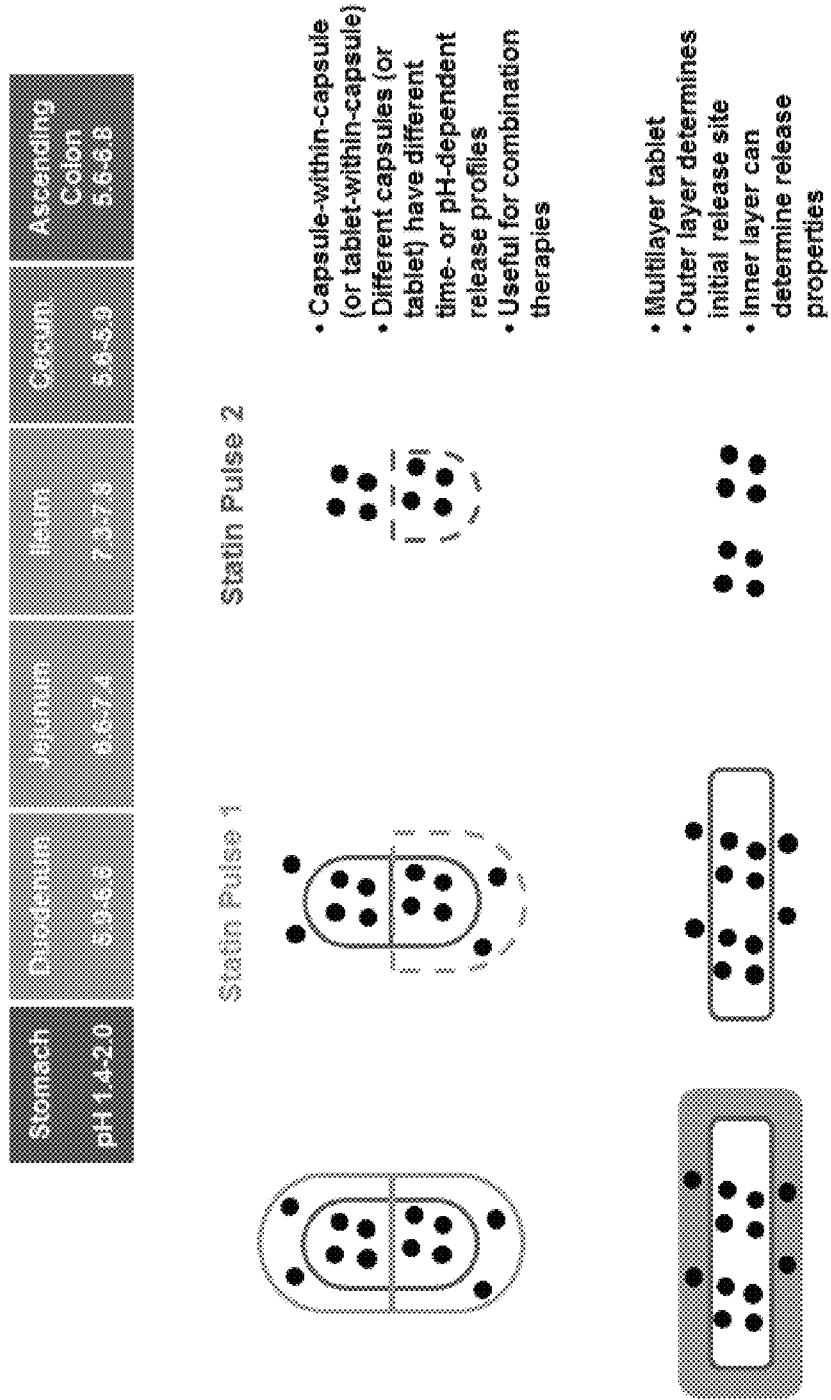
FIG. 2 depicts embodiments of modified-release formulations as multi-layer capsules or tablets for statin delivery to the intestines (an illustrative commercial material is shown, related materials are known in the art).
Figure 3A:
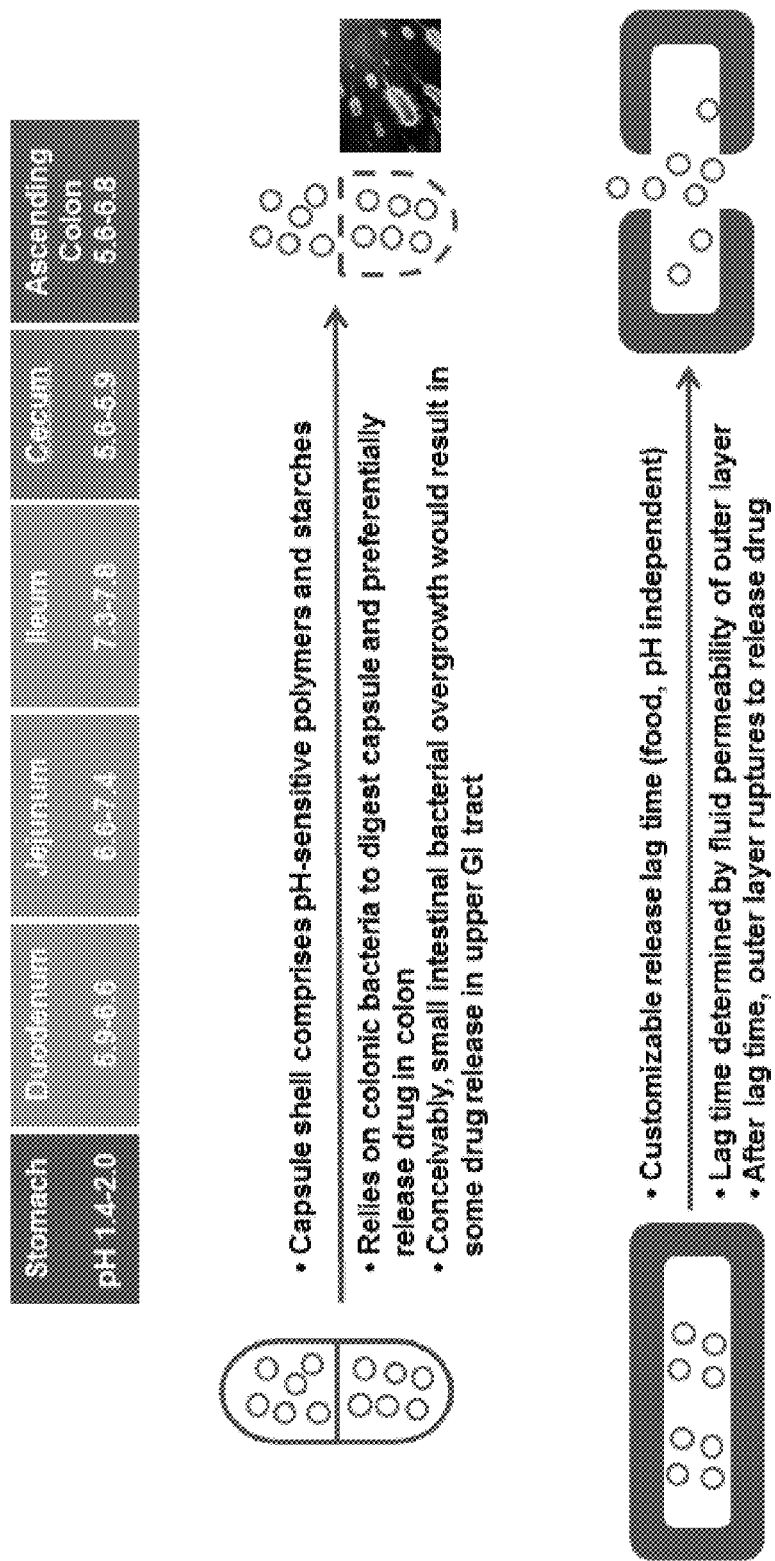
FIGS. 3A-3B depict embodiments of modified-release formulations for colonic delivery (an illustrative commercial material is shown, related materials are known in the art).
Figure 3B:
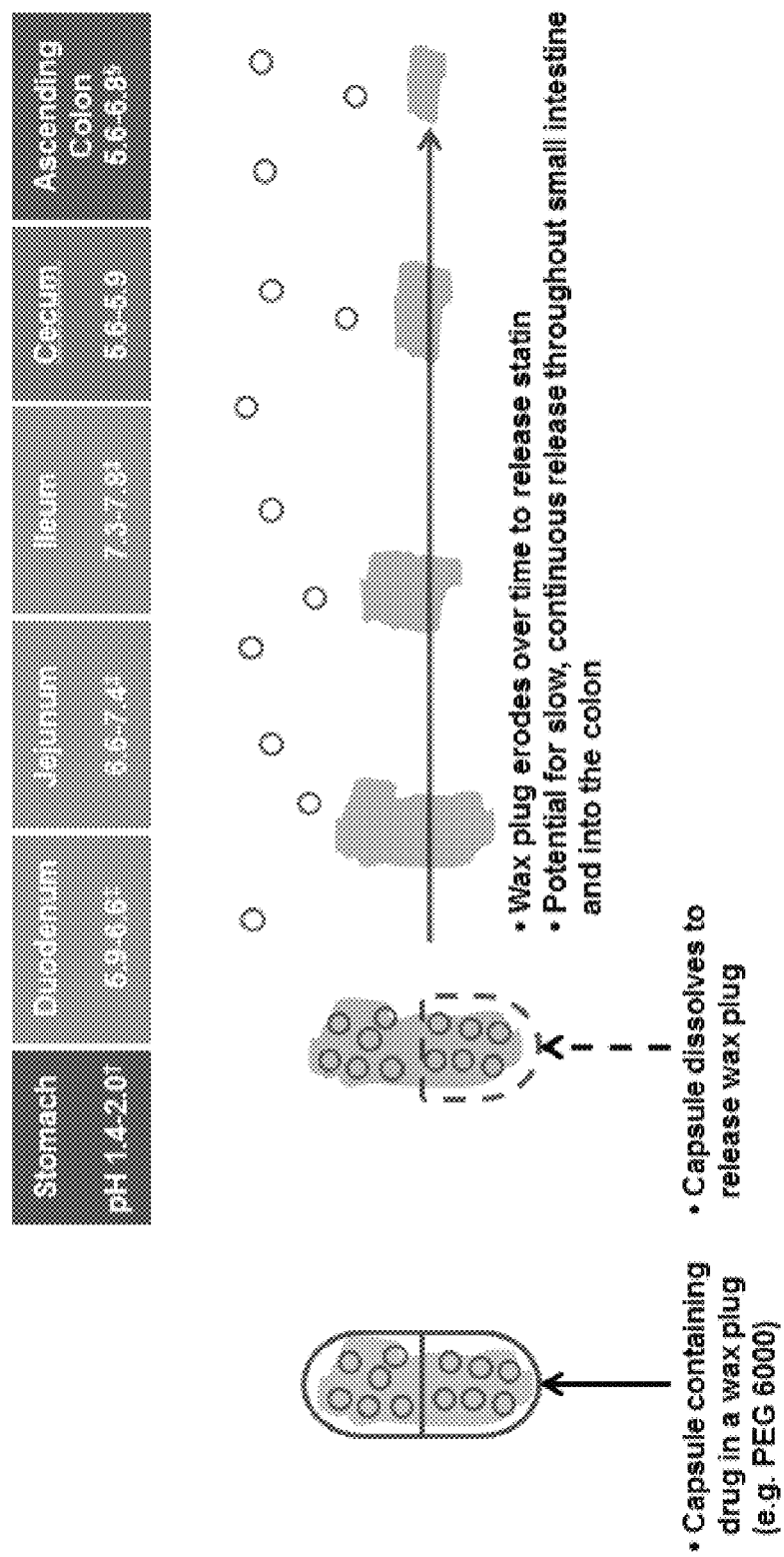
Figure 4:
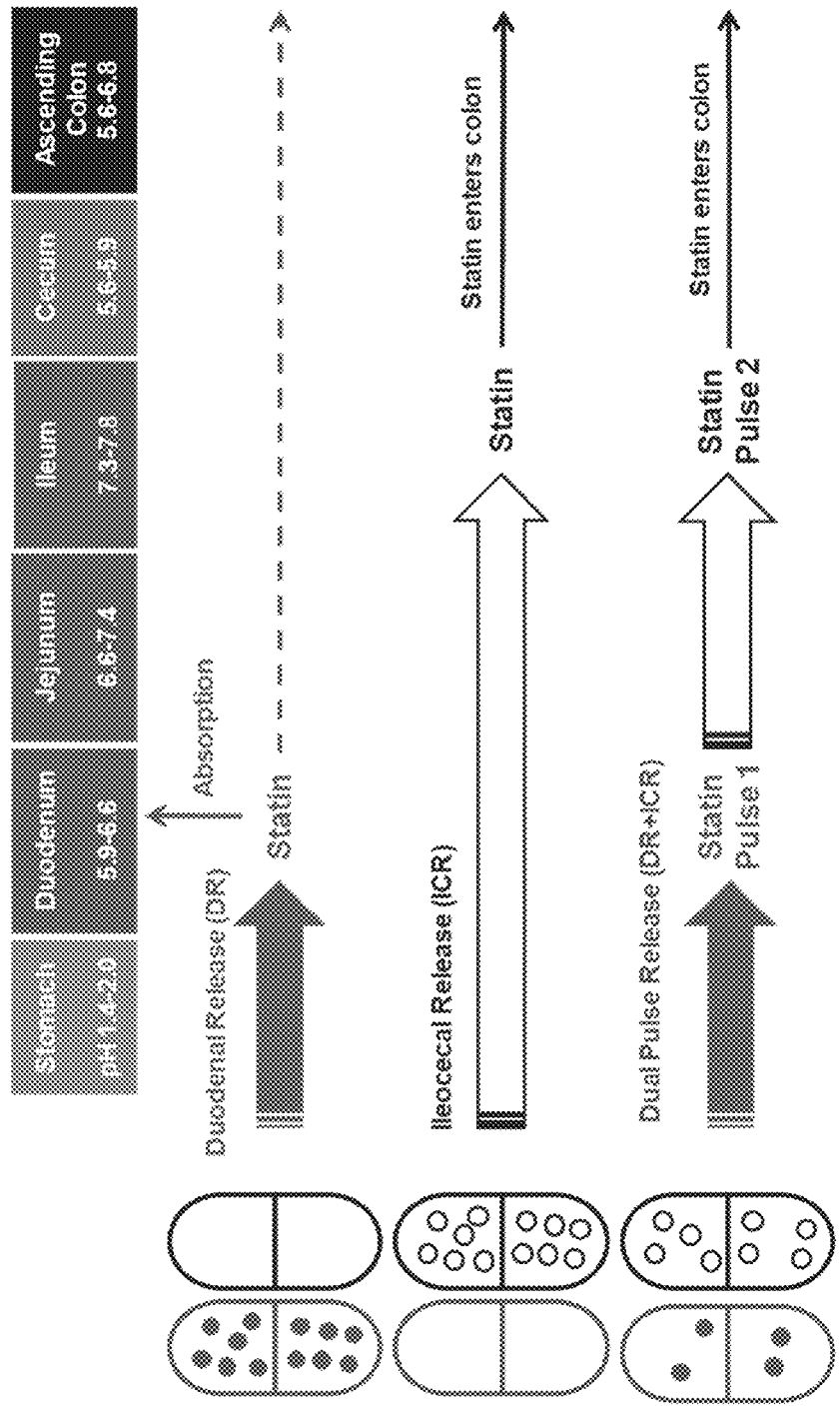
FIG. 4 depicts various embodiments of modified-release formulations in the form of capsules that delivers either one or two doses of statin to the intestines.

The present invention is based, in part, on the surprising discovery of formulations and methods that are useful in effectively treating or preventing methanogen-associated disorders while avoiding side effects. The present invention provides, inter alia, modified-release formulations comprising one or more anti-methanogenic statins which is useful in, for example, the treatment of methanogen-associated disorders such as, for example, IBS (including, for example, IBS-C).

As used herein, "antimethanogenic statin" or "statin" refers to a class of compounds that is known in the art as inhibitors of HMG-CoA reductase used as lipid lowering agents. However, the prior use of the statin compounds does not necessarily imply a mechanism of action in the treatment of methanogenesis. That is, in some embodiments, the statin may inhibit the enzyme HMG-CoA reductase while in others it may have another manner of causing an effect. For example, the statin may target a methanogenic enzyme, such as, for example, one or more of adh alcohol dehydrogenase; fdh formate dehydrogenase; fno F420-dependent NADP oxidoreductase; fir formyl-MF:H4MPT formyltransferase; fwd formyl-MF dehydrogenase; hmd methylene-H4MPT dehydrogenase; mch methenyl-H4MPT cyclohydrolase; mtd F420-dependent methylene-H4MPT dehydrogenase; mer F420-dependent methylene-H4MPT reductase; mtr methyl-H4MPT:CoM-methyltransferase; mcr methyl-CoM reductase; and the mtaB methanol:cobalamin methyltransferase (7) heterodisulfide reductase system. In some embodiments, the statin does not substantially inhibit the enzyme HMG-CoA reductase.

Systemic statin usage has been associated with adverse side effects such as elevation in hepatic enzyme levels and muscle problems (e.g., myalgias, rhabdomyolysis, and severe myopathy). Further, systemic statin usage has been linked to digestive disorders in some patients. The modified release formulations of the present invention minimize absorption of the administered antimethanogenic statin from the intestine into the systemic circulation and reduce side effects, or disease exacerbating effects, associated with the statin. Additionally, not all patients with IBS-C or CIC will require lipid lowering therapy, so statin systemic absorption from the modified release formulations of the present invention will ideally be insufficient to provide a clinically-meaningful reduction in total cholesterol (total-C), or low-density lipoprotein cholesterol (LDL-C), or apolipoprotein B (Apo B), or triglycerides (TG), or a clinically-meaningful increase in high-density lipoprotein cholesterol (HDL-C) (for example, a reduction of less than 5% in serum LDL-C levels at 6 weeks).

Modified Release Profile

In one aspect, the present invention provides modified release formulations comprising at least one anti-methanogenic agent, wherein the formulation releases at least about 60% of the anti-methanogenic agent, such as anti-methanogenic statins, after the stomach and into one or more regions of the intestinal tract.

In various embodiments, the anti-methanogenic agent is an agent that can inhibit the production of methane, inhibit methanogenesis, or inhibit the growth and/or proliferation of methanogens. In some aspects, the anti-methanogenic agent is a statin hydroxyacid molecule which typically is, without wishing to be bound by theory, an effective inhibitor of HMG-CoA reductase or a statin lactone which typically is, without wishing to be bound by theory, an ineffective HMG-CoA inhibitor. In some aspects, the anti-methanogenic agent is referred to as an "antimethanogenic statin" or "statin."

In one aspect, the present invention provides modified release formulations comprising at least one antimethanogenic statin, wherein the formulation releases at least 60% of the antimethanogenic stain after the stomach into one or more regions of the intestinal tract.

Illustrative statins useful for the invention include, but are not limited to, atorvastatin, cerivastatin, dalvastatin, eptastatin, fluindostatin, fluvastatin, lovastatin, mevastatin, pitavastatin, pravastatin, rosuvastatin, simvastatin, velostatin, and pharmaceutically acceptable esters, prodrugs, salts, solvates, enantiomers, stereoisomers, active metabolites, co-crystals, and other physiologically functional derivatives thereof. In one embodiment, the statin is pravastatin. In another embodiment, the statin is lovastatin. In yet another embodiment, the statin is simvastatin. In some embodiments, the statin is in either the lactone or hydroxyacid form. In some embodiments, the antimethanogenic statin is the lactone form of one or more of atorvastatin, cerivastatin, dalvastatin, eptastatin, fluindostatin, fluvastatin, lovastatin, mevastatin, pitavastatin, pravastatin, rosuvastatin, simvastatin, velostatin. In some embodiments, the antimethanogenic statin is the hydroxyacid form of one or more of atorvastatin, cerivastatin, dalvastatin, eptastatin, fluindostatin, fluvastatin, lovastatin, mevastatin, pitavastatin, pravastatin, rosuvastatin, simvastatin, velostatin.

In some embodiments, the antimethanogenic statin is the lactone form of one or more of lovastatin, simvastatin, and mevastatin. In some embodiments, the antimethanogenic statin is the lactone form of lovastatin.

In various embodiments, the antimethanogenic statin (e.g. lovastatin) is substantially in the lactone form at the site of delivery by the present formulations. For example, in some embodiments, the amount of GI tract-delivered antimethanogenic statin (e.g. lovastatin) which is in the lactone form is more than about 95%, or more than about 90%, or more than about 85%, or more than about 80%, or more than about 75%, or more than about 70%, or more than about 65%, or more than about 60%, or more than about 55%, or more than about 50%, or more than about 25%.

In various embodiments, the modified-release formulations of the present invention are designed for immediate release (e.g. upon ingestion). In various embodiments, the modified-release formulations may have sustained-release profiles, i.e. slow release of the active ingredient(s) in the body (e.g., GI tract) over an extended period of time. In various embodiments, the modified-release formulations may have a delayed-release profile, i.e. not immediately release the active ingredient(s) upon ingestion; rather, postponement of the release of the active ingredient(s) until the composition is lower in the gastrointestinal tract; for example, for release in the small intestine (e.g., one or more of duodenum, jejunum, ileum) or the large intestine (e.g., one or more of cecum, ascending, transverse, descending or sigmoid portions of the colon, and rectum). For example, a composition can be enteric coated to delay release of the active ingredient(s) until it reaches the small intestine or large intestine. In some embodiments, there is not a substantial amount of the active ingredient(s) of the present formulations in the stool.

In various embodiments, the modified-release formulation of the present invention releases (optionally as a first release) at least 5%, 10%, 15%, 20%, 25%, 30%, 35%, 40%, 45%, 50%, 55%, or 60% of the antimethanogenic statin after the stomach into one or more regions of the intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the intestine.

In various embodiments, the modified-release formulation releases (optionally as a first release) the antimethanogenic statin in the small intestine. In various embodiments, the modified-release formulation of the present invention releases at least 5%, 10%, 15%, 20%, 25%, 30%, 35%, 40%, 45%, 50%, 55%, or 60% of the antimethanogenic statin in the small intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the small intestine.

In one embodiment, the formulation releases (optionally as a first release) the antimethanogenic statin in the duodenum. In various embodiments, the modified-release formulation of the present invention releases at least 5%, 10%, 15%, 20%, 25%, 30%, 35%, 40%, 45%, 50%, 55%, or 60% of the antimethanogenic statin in the duodenum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the duodenum.

In another embodiment, the formulation releases (optionally as a first release) the antimethanogenic statin in the jejunum. In various embodiments, the modified-release formulation of the present invention releases at least 5%, 10%, 15%, 20%, 25%, 30%, 35%, 40%, 45%, 50%, 55%, or 60% of the antimethanogenic statin in the jejunum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the jejunum.

In a further embodiment, the formulation releases (optionally as a first release) the antimethanogenic statin in the ileum and/or the ileocecal junction. In various embodiments, the modified-release formulation of the present invention releases at least 5%, 10%, 15%, 20%, 25%, 30%, 35%, 40%, 45%, 50%, 55%, or 60% of the antimethanogenic statin in the ileum and/or the ileocecal junction. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the ileum and/or the ileocecal junction.

In other embodiments, the modified-release formulation releases (optionally as a first release) the antimethanogenic statin in the large intestine. In various embodiments, the modified-release formulation of the present invention releases at least 5%, 10%, 15%, 20%, 25%, 30%, 35%, 40%, 45%, 50%, 55%, or 60% of the antimethanogenic statin in the large intestine. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the large intestine.

In an embodiment, the modified-release formulation releases (optionally as a first release) the antimethanogenic statin in the cecum. In various embodiments, the modified-release formulation of the present invention releases at least 5%, 10%, 15%, 20%, 25%, 30%, 35%, 40%, 45%, 50%, 55%, or 60% of the antimethanogenic statin in the cecum. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the cecum.

In another embodiment, the modified-release formulation releases (optionally as a first release) the antimethanogenic statin in the ascending colon. In various embodiments, the modified-release formulation of the present invention releases at least 5%, 10%, 15%, 20%, 25%, 30%, 35%, 40%, 45%, 50%, 55%, or 60% of the antimethanogenic statin in the ascending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the ascending colon.

In yet another embodiment, the antimethanogenic statin is released (optionally as a first release) in the transverse colon. In various embodiments, the modified-release formulation of the present invention releases at least 5%, 10%, 15%, 20%, 25%, 30%, 35%, 40%, 45%, 50%, 55%, or 60% of the antimethanogenic statin in the transverse colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the transverse colon.

In a further embodiment, the antimethanogenic statin is released (optionally as a first release) in the descending colon. In various embodiments, the modified-release formulation of the present invention releases at least 5%, 10%, 15%, 20%, 25%, 30%, 35%, 40%, 45%, 50%, 55%, or 60% of the antimethanogenic statin in the descending colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the descending colon.

In another embodiment, the antimethanogenic statin is released (optionally as a first release) in the sigmoid colon. In various embodiments, the modified-release formulation of the present invention releases at least 5%, 10%, 15%, 20%, 25%, 30%, 35%, 40%, 45%, 50%, 55%, or 60% of the antimethanogenic statin in the sigmoid colon. For example, the modified-release formulation releases at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% of the antimethanogenic statin in the sigmoid colon.

In certain embodiments, the modified-release formulation does not substantially release the antimethanogenic statin in the stomach.

In some embodiments, the modified-release formulation is a HPMC capsule filled with enteric-coated mini-tablets from which lovastatin is released at different intestinal pH values. The mini-tablets are designed to pass through the stomach unchanged then release a small amount of lovastatin into the duodenum and the majority of the lovastatin dose into the ileocecal junction and colon.

In certain embodiments, the modified-release formulation releases the antimethanogenic statin at a specific pH. For example, in some embodiments, the modified-release formulation is substantially stable in an acidic environment and substantially unstable (e.g., dissolves rapidly or is physically unstable) in a near neutral to alkaline environment. In some embodiments, stability is indicative of not substantially releasing while instability is indicative of substantially releasing. For example, in some embodiments, the modified-release formulation is substantially stable at a pH of about 7.0 or less, or about 6.5 or less, or about 6.0 or less, or about 5.5 or less, or about 5.0 or less, or about 4.5 or less, or about 4.0 or less, or about 3.5 or less, or about 3.0 or less, or about 2.5 or less, or about 2.0 or less, or about 1.5 or less, or about 1.0 or less. In some embodiments, the present formulations are stable in lower pH areas and therefore do not substantially release in, for example, the stomach. In some embodiments, modified-release formulation is substantially stable at a pH of about 1 to about 4 or lower and substantially unstable at pH values that are greater. In these embodiments, the modified-release formulation is not substantially released in the stomach. In these embodiments, the modified-release formulation is substantially released in the small intestine (e.g. one or more of the duodenum, jejunum, and ileum) and/or large intestine (e.g. one or more of the cecum, ascending colon, transverse colon, descending colon, and sigmoid colon). In some embodiments, modified-release formulation is substantially stable at a pH of about 4 to about 5 or lower and consequentially is substantially unstable at pH values that are greater and therefore is not substantially released in the stomach and/or small intestine (e.g. one or more of the duodenum, jejunum, and ileum). In these embodiments, the modified-release formulation is substantially released in the large intestine (e.g. one or more of the cecum, ascending colon, transverse colon, descending colon, and sigmoid colon). In various embodiments, the pH values recited herein may be adjusted as known in the art to account for the state of the subject, e.g. whether in a fasting or postprandial state.

In some embodiments, the modified-release formulation is substantially stable in gastric fluid and substantially unstable in intestinal fluid and, accordingly, is substantially released in the small intestine (e.g. one or more of the duodenum, jejunum, and ileum) and/or large intestine (e.g. one or more of the cecum, ascending colon, transverse colon, descending colon, and sigmoid colon).

In some embodiments, the modified-release formulation is stable in gastric fluid or stable in acidic environments. These modified-release formulations release about 30% or less by weight of the antimethanogenic statin and/or additional therapeutic agent in the modified-release formulation in gastric fluid with a pH of about 4 to about 5 or less, or simulated gastric fluid with a pH of about 4 to about 5 or less, in about 15, or about 30, or about 45, or about 60, or about 90 minutes. Modified-release formulations of the of the invention may release from about 0% to about 30%, from about 0% to about 25%, from about 0% to about 20%, from about 0% to about 15%, from about 0% to about 10%, about 5% to about 30%, from about 5% to about 25%, from about 5% to about 20%, from about 5% to about 15%, from about 5% to about 10% by weight of the antimethanogenic statin and/or additional therapeutic agent in the modified-release formulation in gastric fluid with a pH of 4-5, or less or simulated gastric fluid with a pH of 4-5 or less, in about 15, or about 30, or about 45, or about 60, or about 90 minutes. Modified-release formulations of the invention may release about 1%, about 2%, about 3%, about 4%, about 5%, about 6%, about 7%, about 8%, about 9%, or about 10% by weight of the total antimethanogenic statin and/or additional therapeutic agent in the modified-release formulation in gastric fluid with a pH of 5 or less, or simulated gastric fluid with a pH of 5 or less, in about 15, or about 30, or about 45, or about 60, or about 90 minutes.

In some embodiments, the modified-release formulation is unstable in intestinal fluid. These modified-release formulations release about 70% or more by weight of the antimethanogenic statin and/or additional therapeutic agent in the modified-release formulation in intestinal fluid or simulated intestinal fluid in about 15, or about 30, or about 45, or about 60, or about 90 minutes. In some embodiments, the modified-release formulation is unstable in near neutral to alkaline environments. These modified-release formulations release about 70% or more by weight of the antimethanogenic statin and/or additional therapeutic agent in the modified-release formulation in intestinal fluid with a pH of about 4-5 or greater, or simulated intestinal fluid with a pH of about 4-5 or greater, in about 15, or about 30, or about 45, or about 60, or about 90 minutes. A modified-release formulation that is unstable in near neutral or alkaline environments may release 70% or more by weight of antimethanogenic statin and/or additional therapeutic agent in the modified-release formulation in a fluid having a pH greater than about 5 (e.g., a fluid having a pH of from about 5 to about 14, from about 6 to about 14, from about 7 to about 14, from about 8 to about 14, from about 9 to about 14, from about 10 to about 14, or from about 11 to about 14) in from about 5 minutes to about 90 minutes, or from about 10 minutes to about 90 minutes, or from about 15 minutes to about 90 minutes, or from about 20 minutes to about 90 minutes, or from about 25 minutes to about 90 minutes, or from about 30 minutes to about 90 minutes, or from about 5 minutes to about 60 minutes, or from about 10 minutes to about 60 minutes, or from about 15 minutes to about 60 minutes, or from about 20 minutes to about 60 minutes, or from about 25 minutes to about 90 minutes, or from about 30 minutes to about 60 minutes.

In one embodiment, the modified-release formulation may remain essentially intact, or may be essentially insoluble, in gastric fluid. The stability of the delayed-release coating can be pH dependent. Delayed-release coatings that are pH dependent will be substantially stable in acidic environments (pH of about 5 or less), and substantially unstable in near neutral to alkaline environments (pH greater than about 5). For example, the delayed-release coating may essentially disintegrate or dissolve in near neutral to alkaline environments such as are found in the small intestine (e.g. one or more of the duodenum, jejunum, and ileum) and/or large intestine (e.g. one or more of the cecum, ascending colon, transverse colon, descending colon, and sigmoid colon).

Examples of simulated gastric fluid and simulated intestinal fluid include, but are not limited to, those disclosed in the 2005 Pharmacopeia 23NF/28USP in Test Solutions at page 2858 and/or other simulated gastric fluids and simulated intestinal fluids known to those of skill in the art, for example, simulated gastric fluid and/or intestinal fluid prepared without enzymes.

Alternatively, the stability of the modified-release formulation can be enzyme-dependent. Delayed-release coatings that are enzyme dependent will be substantially stable in fluid that does not contain a particular enzyme and substantially unstable in fluid containing the enzyme. The delayed-release coating will essentially disintegrate or dissolve in fluid containing the appropriate enzyme. Enzyme-dependent control can be brought about, for example, by using materials which release the active ingredient only on exposure to enzymes in the intestine, such as galactomannans. Also, the stability of the modified-release formulation can be dependent on enzyme stability in the presence of a microbial enzyme present in the gut flora.

In some embodiments, a dual pulse formulation is provided. In various embodiments, the present invention provides for modified-release formulations that release multiple doses of the antimethanogenic statin, at different locations along the intestines, at different times, and/or at different pH.

In an illustrative embodiment, the modified-release formulation comprises a first dose of the antimethanogenic statin and a second dose of the antimethanogenic statin, wherein the first dose and the second dose are released at different locations along the intestines, at different times, and/or at different pH. For example, the first dose is released at the duodenum, and the second dose is released at the ileocecal junction and/or colon. In another example, the first dose is released at the jejunum, and the second dose is released at the ileum. In other embodiments, the first dose is released at a location along the small intestine (e.g., the duodenum), while the second dose is released along the large intestine (e.g., the ascending colon). In various embodiments, the modified-release formulation may release at least one dose, at least two doses, at least three doses, at least four doses, at least five doses, at least six doses, at least seven doses, or at least eight doses of the antimethanogenic statin at different locations along the intestines, at different times, and/or at different pH. Each individual dose may comprise the same statin or may comprise different statins. For example, the modified-release formulation may release multiple doses, with the first dose being released at the duodenum and the second and/or additional dose being released at the ileocecal junction and/or colon.

In some embodiments, the dual pulse formulation is an enteric-coated capsule comprising beads or mini-tablets that comprise an antimethanogenic statin and optionally an additional therapeutic agent. In some embodiments, the enteric-coated capsule dissolves in a first area of GI tract to release the beads or mini-tablets and/or a first population of beads or mini-tablets releases in a second area of the GI tract and (that is not the same as the first area of the GI tract) and a second population of beads or mini-tablets releases in a third area of the GI tract and (that is not the same as the first or second areas of the GI tract). In some embodiments, the dose/release ratio (e.g. how much agent is released in various locations) can be tuned as needed. In some embodiments, the enteric-coated capsule dissolves in the duodenum to release the beads or mini-tablets and/or a first population of beads or mini-tablets releases in the duodenum and/or a second population of beads or mini-tablets releases in the ileocecal junction (see, e.g. FIGS. 1-4).

In alternative embodiments, the dual pulse formulation is a water-soluble capsule comprising enteric-coated beads or mini-tablets that comprise an antimethanogenic statin and optionally an additional therapeutic agent. Illustrative water-soluble capsules include, but are not limited to, gelatin and hydroxypropyl methylcellulose (HPMC) capsules. In some embodiments, the water-soluble capsule dissolves in a first area of GI tract to release the beads or mini-tablets and/or a first population of beads or mini-tablets releases in a second area of the GI tract and (that is not the same as the first area of the GI tract) and a second population of beads or mini-tablets releases in a third area of the GI tract and (that is not the same as the first or second areas of the GI tract). In some embodiments, the water-soluble capsule dissolves in the stomach to release the beads or mini-tablets and/or a first population of beads or mini-tablets releases in the duodenum and/or a second population of beads or mini-tablets releases in the ileocecal junction and/or colon.

Modified Release Formulation and Dosage Forms

The modified-release formulation of the present invention may further comprise a pharmaceutically acceptable carrier or excipient. As one skilled in the art will recognize, the formulations can be in any suitable form appropriate for the desired use and route of administration. Examples of suitable dosage forms include, for example, oral and parenteral dosage forms.

Suitable dosage forms for oral use include, for example, solid dosage forms such as tablets, dispersible powders, granules, and capsules. In one embodiment, the modified-release formulation is in the form of a tablet. In another embodiment, the modified-release formulation is in the form of a capsule. In yet another embodiment, the modified-release formulation is in the form of a soft-gel capsule. In a further embodiment, the modified-release formulation is in the form of a gelatin capsule. In a further embodiment, the modified-release formulation is in the form of a hydroxypropyl methylcellulose (HPMC) capsule.

In such dosage forms, the active compound is mixed with at least one inert, pharmaceutically acceptable excipient or carrier such as sodium citrate, dicalcium phosphate, etc., and/or a) fillers, diluents, or extenders such as starches, lactose, sucrose, glucose, mannitol, silicic acid, microcrystalline cellulose (e.g., Avicel PH102), and Bakers Special Sugar, etc., b) binders such as, for example, carboxymethylcellulose, alginates, gelatin, polyvinylpyrrolidone, sucrose, acacia, polyvinyl alcohol, polyvinylpyrrolidone, methylcellulose, hydroxypropyl cellulose, hydroxymethyl cellulose, and copovidones such as Kollidon® VA64, and Kollidon® VA64 Fine, etc., c) humectants such as glycerol, etc., d) disintegrating agents such as agar-agar, calcium carbonate, potato or tapioca starch, alginic acid, certain silicates, sodium carbonate, cross-linked polymers such as crospovidone (cross-linked polyvinylpyrrolidone), croscarmellose sodium (cross-linked sodium carboxymethylcellulose), sodium starch glycolate, etc., e) solution retarding agents such as paraffin, etc., f) absorption accelerators such as quaternary ammonium compounds, etc., g) wetting agents such as, for example, cetyl alcohol and glycerol monostearate, etc., h) absorbents such as kaolin and bentonite clay, etc., i) lubricants such as talc, calcium stearate, magnesium stearate, solid polyethylene glycols, sodium lauryl sulfate, glyceryl behenate, etc., j) antioxidants such as propyl gallate, butylated hydroxyanisole (BHA), butylated hydroxytoluene (BHT), ethylenediaminetetraacetic acid (also known as Edetic Acid or EDTA) etc., k) viscosity and dispersion agents such as silicon dioxide or silica, and mixtures of such excipients. One of skill in the art will recognize that particular excipients may have two or more functions in the oral dosage form. In the case of an oral dosage form, for example, a capsule or a tablet, the dosage form may also comprise buffering agents.

The modified release formulation can additionally include a surface active agent. Surface active agents suitable for use in the present invention include, but are not limited to, any pharmaceutically acceptable, non-toxic surfactant. Classes of surfactants suitable for use in the compositions of the invention include, but are not limited to polyethoxylated fatty acids, PEG-fatty acid diesters, PEG-fatty acid mono- and di-ester mixtures, polyethylene glycol glycerol fatty acid esters, alcohol-oil transesterification products, polyglycerized fatty acids, propylene glycol fatty acid esters, mixtures of propylene glycol esters-glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-olyoxypropylene block copolymers, sorbitan fatty acid esters, lower alcohol fatty acid esters, ionic surfactants, and mixtures thereof. In some embodiments, compositions of the invention may comprise one or more surfactants including, but not limited to, sodium lauryl sulfate, polysorbate 20, polysorbate 40, polysorbate 60, polysorbate 80, and triethyl citrate.

The modified-release formulation can also contain pharmaceutically acceptable plasticizers to obtain the desired mechanical properties such as flexibility and hardness. Such plasticizers include, but are not limited to, triacetin, citric acid esters, phthalic acid esters, dibutyl sebacate, cetyl alcohol, polyethylene glycols, polysorbates or other plasticizers.

The modified-release formulation can also include one or more application solvents. Some of the more common solvents that can be used to apply, for example, a delayed-release coating composition include isopropyl alcohol, acetone, methylene chloride and the like.

The modified-release formulation can also include one or more disintegrants. Illustrative disintegrants that may be utilized include, but are not limited to crospovidones such as Kollidon® CL, Kollidon® CL-F, Kollidon® CL-SF, or Kollidon® CL-M, The modified-release formulation can also include one or more alkaline materials. Alkaline material suitable for use in compositions of the invention include, but are not limited to, sodium, potassium, calcium, magnesium and aluminum salts of acids such as phosphoric acid, carbonic acid, citric acid and other aluminum/magnesium compounds. In addition the alkaline material may be selected from antacid materials such as aluminum hydroxides, calcium hydroxides, magnesium hydroxides and magnesium oxide.

The solid oral dosage forms can be prepared by any conventional method known in the art, for example granulation (e.g., wet or dry granulation) of the active compound (e.g., statins) with one or more suitable excipients. Alternatively, the active compound can be layered onto an inert core (e.g., a nonpareil/sugar sphere or silica sphere) using conventional methods such as fluidized bed or pan coating, or extruded and spheronized using methods known in the art, into active compound-containing beads. Such beads can then be incorporated into tablets or capsules using conventional methods.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, etc., and mixtures thereof.

Besides inert diluents, the oral compositions can also include adjuvants such as sweetening, flavoring, and perfuming agents.

Suspensions, in addition to the active compounds, may contain suspending agents such as, for example, ethoxylated isostearyl alcohols, polyoxyethylene sorbitol and sorbitan esters, microcrystalline cellulose, aluminum metahydroxide, bentonite, agar-agar, tragacanth, etc., and mixtures thereof.

The formulations comprising the therapeutic agents of the present invention may conveniently be presented in unit dosage forms and may be prepared by any of the methods well known in the art of pharmacy. Such methods generally include the step of bringing the therapeutic agents into association with a carrier, which constitutes one or more accessory ingredients. Typically, the formulations are prepared by uniformly and intimately bringing the therapeutic agent into association with a liquid carrier, a finely divided solid carrier, or both, and then, if necessary, shaping the product into dosage forms of the desired formulation (e.g., wet or dry granulation, powder blends, etc., followed by tableting using conventional methods known in the art).

In various embodiments, the modified-release formulation of the present invention may utilize one or more modified-release coatings such as delayed-release coatings to provide for effective, delayed yet substantial delivery of the antimethanogenic statin to the GI tract together with, optionally, other therapeutic agents.

In one embodiment, the delayed-release coating includes an enteric agent that is substantially stable in acidic environments and substantially unstable in near neutral to alkaline environments. In an embodiment, the delayed-release coating contains an enteric agent that is substantially stable in gastric fluid. The enteric agent can be selected from, for example, solutions or dispersions of methacrylic acid copolymers, cellulose acetate phthalate, hydroxypropylmethyl cellulose phthalate, polyvinyl acetate phthalate, carboxymethylethylcellulose, and EUDRAGIT®-type polymer (poly (methacrylic acid, methylmethacrylate), hydroxypropyl methylcellulose acetate succinate, cellulose acetate trimellitate, shellac or other suitable enteric coating polymers. The EUDRAGIT®-type polymers include, for example, EUDRAGIT® FS 30D, L 30 D-55, L 100-55, L 100, L 12,5, L 12,5 P, RL 30 D, RL PO, RL 100, RL 12,5, RS 30 D, RS PO, RS 100, RS 12,5, NE 30 D, NE 40 D, NM 30 D, S 100, S 12,5, and S 12,5 P. Similar polymers include Kollicoat® MAE 30 DP and Kollicoat® MAE 100 P. In some embodiments, one or more of EUDRAGIT® FS 30D, L 30 D-55, L 100-55, L 100, L 12,5, L 12,5 P RL 30 D, RL PO, RL 100, RL 12,5, RS 30 D, RS PO, RS 100, RS 12,5, NE 30 D, NE 40 D, NM 30 D, S 100, S 12,5 S 12,5 P, Kollicoat® MAE 30 DP and Kollicoat® MAE 100 P is used. In various embodiments, the enteric agent may be a combination of the foregoing solutions or dispersions. In certain embodiments, one or more coating system additives are used with the enteric agent. For example, one or more PlasACRYL™ additives may be used as an anti-tacking agent coating additive. Illustrative PlasACRYL™ additives include, but are not limited to PlasACRYL™ HTP20 and PlasACRYL™ T20. In an embodiment, PlasACRYL™ HTP20 is formulated with EUDRAGIT® L 30 D-55 coatings. In another embodiment, PlasACRYL™ T20 is formulated with EUDRAGIT® FS 30 D coatings.

In another embodiment, the delayed-release coating may degrade as a function of time when in aqueous solution without regard to the pH and/or presence of enzymes in the solution. Such a coating may comprise a water insoluble polymer. Its solubility in aqueous solution is therefore independent of the pH. The term "pH independent" as used herein means that the water permeability of the polymer and its ability to release pharmaceutical ingredients is not a function of pH and/or is only very slightly dependent on pH. Such coatings may be used to prepare, for example, sustained release formulations. Suitable water insoluble polymers include pharmaceutically acceptable non-toxic polymers that are substantially insoluble in aqueous media, e.g., water, independent of the pH of the solution. Suitable polymers include, but are not limited to, cellulose ethers, cellulose esters, or cellulose ether-esters, i.e., a cellulose derivative in which some of the hydroxy groups on the cellulose skeleton are substituted with alkyl groups and some are modified with alkanoyl groups. Examples include ethyl cellulose, acetyl cellulose, nitrocellulose, and the like. Other examples of insoluble polymers include, but are not limited to, lacquer, and acrylic and/or methacrylic ester polymers, polymers or copolymers of acrylate or methacrylate having a low quaternary ammonium content, or mixture thereof and the like. Other examples of insoluble polymers include EUDRAGIT RS®, EUDRAGIT RL®, and EUDRAGIT NEC). Insoluble polymers useful in the present invention include polyvinyl esters, polyvinyl acetals, polyacrylic acid esters, butadiene styrene copolymers, and the like. In one embodiment, colonic delivery is achieved by use of a slowly-eroding wax plug (e.g., various PEGS, including for example, PEG6000).

In a further embodiment, the delayed-release coating may be degraded by a microbial enzyme present in the gut flora. In one embodiment, the delayed-release coating may be degraded by a bacteria present in the small intestine. In another embodiment, the delayed-release coating may be degraded by a bacteria present in the large intestine.

The present invention provides for modified-release formulations that release multiple doses of the antimethanogenic statin along the gastrointestinal tract. The overall release profile of such a formulation may be adjusted by utilizing, for example, multiple particle types or multiple layers. In one embodiment, the first dose of the antimethanogenic statin may be formulated for release in, for example, the duodenum, whereas the second dose is formulated for delayed release in, for example, the ileum. In another embodiment, the first dose of the antimethanogenic statin may be formulated for release in, for example, the small intestines, whereas the second dose is formulated for delayed release in, for example, the large intestines. Alternatively, multiple doses are released at different locations alone the intestine.

In one embodiment, one or more doses of the antimethanogenic statin may be encapsulated in a core particle, for example, in the form of a microbead or a mini-tablet. For example, the first dose of the antimethanogenic statin may be encapsulated in a core particle coated with a modified-release coating designed for release at a first location along the intestinal tract, and the second dose of the antimethanogenic statin may be encapsulated in a core particle coated with a modified-release coating designed for release at a second location along the intestinal tract. In various embodiments, the formulation may comprise a plurality of such modified-release particles. For example, the formulation may be in the form of capsules comprising multiple microbeads or multiple mini-tablets. For example, the formulation may be in the form of capsules such as, for example, gelatin and hydroxypropyl methylcellulose (HPMC) capsules comprising multiple enteric-coated microbeads or mini-tablets. In such an embodiment, a combination of microbeads or mini-tablets may be utilized in which each microbead or mini-tablet is designed to release at a specific time point or location. In an alternative embodiment, the formulation is formulated as a capsule within a capsule, with each capsule having different time- or pH-dependent release properties.

In some embodiments, the formulation may comprise multiple microbeads or multiple mini-tablets at specific ratios so as to release specified amount of the active ingredients at specific time points or locations. For example, the formulation may comprise specific ratios of mini-tablets that release at a first location (e.g., the duodenum) or a first pH (e.g., pH of about 5.5) and mini-tablets that release at a second location (e.g., the ileocecal junction or colon) or a second pH (e.g., pH of about 7.0). In some embodiments, the ratio is about 1:10 to about 10:1. For example, the formulation may comprise mini-tablets that release at a first pH (e.g. pH of about 5.5) and at a second pH (e.g., pH of about 7.0) at a ratio of 1:1, 1:2, 1:3, 1:4, 1:5, 1:6, 1:7, 1:8, 1:9, 1:10, 10:1, 9:1, 8:1, 7:1, 6:1, 5:1, 4:1, 3:1, or 2:1. In one embodiment, the formulation may comprise mini-tablets that release at a first pH (e.g. pH of about 5.5) and at a second pH (e.g., pH of about 7.0) at a ratio of 1:2. In another embodiment, the formulation may comprise mini-tablets that release at a first pH (e.g. pH of about 5.5) and at a second pH (e.g., pH of about 7.0) at a ratio of 1:5.

In another embodiment, one or more doses of the antimethanogenic statin may be encapsulated in a layer. For example, the first dose of the antimethanogenic statin may be encapsulated in a layer coated with a modified-release coating designed for release at a first location along the intestinal tract, and the second dose of the antimethanogenic statin may be encapsulated in a layer coated with a modified-release coating designed for release at a second location along the intestinal tract. The formulation may comprise a plurality of such modified-release layers. For example, the formulation is in the form of multi-layered tablet or a multi-layered capsule or capsules within capsules. Each layer may have different time- or pH-dependent release properties.

In the above embodiments, the coated particles or layers with the delayed-release coating may be further covered with an overcoat layer. The overcoat layer can be applied as described for the other coating compositions. The overcoat materials are pharmaceutically acceptable compounds such as sugar, polyethylene glycol, polyvinylpyrrolidone, polyvinyl alcohol, polyvinyl acetate, hydroxypropyl cellulose, methylcellulose, ethylcellulose, hydroxypropyl methylcellulose, carboxymethylcellulose sodium and others, used alone or in mixtures. The overcoat materials can prevent potential agglomeration of particles coated with the delayed-release coating, protect the delayed-release coating from cracking during the compaction process or enhance the tableting process.

Furthermore, in various embodiments, the agents described herein may be in the form of a pharmaceutically acceptable salt, namely those salts which are suitable for use in contact with the tissues of humans and other animals without undue toxicity, irritation, allergic response and the like, and are commensurate with a reasonable benefit/risk ratio. Pharmaceutically acceptable salts are well known in the art. The salts can be prepared in situ during the final isolation and purification of the therapeutic agents, or separately by reacting the free base function with a suitable acid or a free acid functionality with an appropriate alkaline moiety. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

In various embodiments, the formulation comprises at least one microbead or mini-tablet. In some embodiments, each microbead or mini-tablet comprises about 5-20% by weight the antimethanogenic statin (which is, in some embodiments, lovastatin, and in further embodiments, lovastatin lactone). For example, the antimethanogenic statin may be present at about 5%, about 6%, about 7%, about 8%, about 9%, about 10%, about 11%, about 12%, about 13%, about 14%, about 15%, about 16%, about 17%, about 18%, about 19%, or about 20% by weight. In some embodiments, each microbead or mini-tablet may further comprise about 50-70% by weight tablet diluent (e.g., about 50%, about 51%, about 52%, about 53%, about 54%, about 55%, about 56%, about 57%, about 58%, about 59%, about 60%, about 61%, about 62%, about 63%, about 64%, or about 65%, or about 66%, about 67%, or about 68%, or about 69%, or about 70%). In some embodiments, each microbead or mini-tablet may further comprise about 1-10% by weight tablet binder (e.g., about 1%, about 2%, about 3%, about 4%, about 5%, about 6%, about 7%, about 8%, about 9%, or about 10%). In some embodiments, each microbead or mini-tablet may further comprise about 0.1-3.0% by weight viscosity and dispersion agent (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, each microbead or mini-tablet may further comprise about 0.1-3.0% by weight lubricant, for example, to facilitate tableting (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, each microbead or mini-tablet may further comprise about 1-10% by weight tablet disintegrant (e.g., about 1%, about 2%, about 3%, about 4%, about 5%, about 6%, about 7%, about 8%, about 9%, or about 10%). In some embodiments, each microbead or mini-tablet may further comprise about 10-20% by weight an enteric polymer that dissolves at a pH of either about 5.5 or about 7.0 (e.g., about 10%, about 11%, about 12%, about 13%, about 14%, about 15%, about 16%, about 17%, about 18%, about 19%, or about 20%).

In various embodiments, the formulation comprises one or more of, or two or more of, or three or more of, or four or more of, or five or more of, or all of an antimethanogenic statin (which is, in some embodiments, lovastatin, and in further embodiments, lovastatin lactone), the antimethanogenic statin (which is, in some embodiments, lovastatin, and in further embodiments, lovastatin lactone) optionally being in two doses; microcrystalline cellulose (e.g. Avicel PH102); copovidone (e.g. Kollidon VA64 Fine); silicon dioxide (e.g. Aerosil 200); magnesium stearate; crospovidone (e.g. Kollidon CL or Kollidon CL-F); where the first dose of at least one antimethanogenic statin is encapsulated by an enteric polymer that dissolves at a pH of about 5.5 (e.g. EUDRAGIT L 30 D-55+PlasACRYL HTP20); and the second dose of at least one antimethanogenic statin is encapsulated by an enteric polymer that dissolves a at pH of about 7.0 (e.g. EUDRAGIT FS 30 D+PlasACRYL T20 and/or EUDRAGIT® S 100).

In various embodiments, the formulation comprises at least one microbead or mini-tablet. Each microbead or mini-tablet comprises about 5-20% by weight of the antimethanogenic statin (which is, in some embodiments, lovastatin, and in further embodiments, lovastatin lactone). For example, the antimethanogenic statin may be present at about 5%, about 6%, about 7%, about 8%, about 9%, about 10%, about 11%, about 12%, about 13%, about 14%, about 15%, about 16%, about 17%, about 18%, about 19%, or about 20% by weight. In some embodiments, each microbead or mini-tablet may further comprise about 50-70% by weight microcrystalline cellulose (e.g. Avicel PH102). For example, the microcrystalline cellulose may be present at about 50%, about 51%, about 52%, about 53%, about 54%, about 55%, about 56%, about 57%, about 58%, about 59%, about 60%, about 61%, about 62%, about 63%, about 64%, or about 65%, or about 66%, about 67%, or about 68%, or about 69%, or about 70% by weight. In some embodiments, each microbead or mini-tablet may further comprise about 1-10% by weight copovidone (e.g. Kollidon VA64 Fine). For example, the copovidone may be present at about 1%, about 2%, about 3%, about 4%, about 5%, about 6%, about 7%, about 8%, about 9%, or about 10% by weight. In some embodiments, each microbead or mini-tablet may further comprise about 0.1-3.0% by weight silicon dioxide (e.g. Aerosil 200). For example, the silicon dioxide may be present at about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0% by weight. In some embodiments, each microbead or mini-tablet may further comprise about 0.1-3.0% by weight magnesium stearate (for example, about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, each microbead or mini-tablet may further comprise about 1-10% by weight crospovidone (e.g. Kollidon CL or Kollidon CL-F). For example, the crospovidone may be present at about 1%, about 2%, about 3%, about 4%, about 5%, about 6%, about 7%, about 8%, about 9%, or about 10% by weight. In some embodiments, each microbead or mini-tablet may further comprise about 10-20% by weight an enteric polymer that dissolves at a pH of about 5.5 (e.g. EUDRAGIT L 30 D-55+PlasACRYL HTP20) or about 7.0 (e.g. EUDRAGIT FS 30 D+PlasACRYL T20 and/or EUDRAGIT® S 100). For example, the enteric polymer may be about 10%, about 11%, about 12%, about 13%, about 14%, about 15%, about 16%, about 17%, about 18%, about 19%, or about 20% by weight.

In some embodiments, the formulation comprises at least one microbead or mini-tablet with each microbead or mini-tablet comprising about 12% by weight the antimethanogenic statin (which is, in some embodiments, lovastatin, and in further embodiments, lovastatin lactone); about 60% by weight microcrystalline cellulose (e.g. Avicel PH102); about 6% by weight copovidone (e.g. Kollidon VA64 Fine); about 2% by weight silicon dioxide (e.g. Aerosil 200); about 1% by weight magnesium stearate; about 5% by weight crospovidone (e.g. Kollidon CL or Kollidon CL-F); and about 15% by weight an enteric polymer that dissolves at a pH of about 5.5 (e.g. EUDRAGIT L 30 D-55+PlasACRYL HTP20) or about 7.0 (e.g. EUDRAGIT FS 30 D+PlasACRYL T20 and/or EUDRAGIT® S 100).

In some embodiments, the formulation comprises at least one microbead or mini-tablet with each microbead or mini-tablet comprising about 12.2% by weight lovastatin lactone; about 60.9% by weight microcrystalline cellulose (Avicel PH102); about 6.1% by weight copovidone (Kollidon VA64 Fine); about 1.7% by weight silicon dioxide (Aerosil 200); about 0.9% by weight magnesium stearate; about 5.2% by weight crospovidone (Kollidon CL-F); and either about 13.0% by weight of EUDRAGIT L 30 D-55+PlasACRYL HTP20 coating (which dissolves at a pH of about 5.5) or 13% by weight of EUDRAGIT FS 30 D+PlasACRYL T20 coating (which dissolves at a pH of about 7.0).

In various embodiments, the present formulation comprise a mini-tablet enteric coating thickness, e.g. EUDRAGIT, e.g. EUDRAGIT L 30 D-55 or EUDRAGIT FS 30 D, of greater than about 10%, about 13%, about 15%, or about 17%, or about 20%, or about 25%.

In various embodiments, the formulation of the present invention may comprise at least one mini-tablet that releases at a first pH (e.g. pH of about 5.5) and at least one mini-tablet that releases at a second pH (e.g., pH of about 7.0) at a ratio of 1:2. In such embodiments, the formulation may comprise about 5-20% by weight the antimethanogenic statin (which is, in some embodiments, lovastatin, and in further embodiments, lovastatin lactone). For example, the antimethanogenic statin may be present at about 5%, about 6%, about 7%, about 8%, about 9%, about 10%, about 11%, about 12%, about 13%, about 14%, about 15%, about 16%, about 17%, about 18%, about 19%, or about 20% by weight of the entire formulation. In some embodiments, the formulation may further comprise about 30-60% by weight tablet diluent (e.g., about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%). In some embodiments, the formulation may further comprise about 1-10% by weight tablet binder (e.g., about 1%, about 2%, about 3%, about 4%, about 5%, about 6%, about 7%, about 8%, about 9%, or about 10%). In some embodiments, the formulation may further comprise about 0.1-3.0% by weight viscosity and dispersion agent (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, the formulation may further comprise about 0.1-3.0% by weight lubricant, for example, to facilitate tableting (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, the formulation may further comprise about 1-10% by weight tablet disintegrant (e.g., about 1%, about 2%, about 3%, about 4%, about 5%, about 6%, about 7%, about 8%, about 9%, or about 10%). In some embodiments, the formulation may further comprise about 0.5-10% by weight an enteric polymer that dissolves at a pH of about 5.5 (e.g. EUDRAGIT L 30 D-55+PlasACRYL HTP20). For example, the enteric polymer that dissolves at a pH of about 5.5 may be present in the formulation at about 0.5%, about 0.6%, about 0.7%, about 0.8%, about 0.9%, about 1%, about 2%, about 3%, about 4%, about 5%, about 6%, about 7%, about 8%, about 9%, or about 10% by weight. In some embodiments, the formulation may further comprise about 1-15% by weight an enteric polymer that dissolves at a pH of about 7.0. (e.g. EUDRAGIT FS 30 D+PlasACRYL T20 and/or EUDRAGIT® S 100). For example, the enteric polymer that dissolves at a pH of about 7.0 may be present in the formulation at about 1%, about 2%, about 3%, about 4%, about 5%, about 6%, about 7%, about 8%, about 9%, about 10%, about 11%, about 12%, about 13%, about 14%, or about 15% by weight. In such embodiments, the antimethanogenic statin (which is, in some embodiments, lovastatin, and in further embodiments, lovastatin lactone) may be released in two doses. The first dose of antimethanogenic statin is encapsulated by the enteric polymer that dissolves at a pH of about 5.5; and the second dose of antimethanogenic statin is encapsulated by the enteric polymer that dissolves a at pH of about 7.0.

For example, the formulation may comprise at least one mini-tablet that releases at a first pH (e.g. pH of about 5.5) and at least one mini-tablet that releases at a second pH (e.g., pH of about 7.0) at a ratio of 1:2. The formulation may comprise about 9% by weight the antimethanogenic statin (which is, in some embodiments, lovastatin, and in further embodiments, lovastatin lactone); about 42% by weight microcrystalline cellulose (e.g. Avicel PH102); about 4% by weight copovidone (e.g. Kollidon VA64 Fine); about 1% by weight silicon dioxide (e.g. Aerosil 200); about 0.5% by weight magnesium stearate; about 4% by weight crospovidone (e.g. Kollidon CL or Kollidon CL-F); about 3% by weight an enteric polymer that dissolves at a pH of about 5.5 (e.g. EUDRAGIT L 30 D-55+PlasACRYL HTP20); and about 6% by weight an enteric polymer that dissolves at a pH of about 7.0 (e.g. EUDRAGIT FS 30 D+PlasACRYL T20 and/or EUDRAGIT® S 100).

In another example, the formulation may comprise at least one mini-tablet that releases at a first pH (e.g. pH of about 5.5) and at least one mini-tablet that releases at a second pH (e.g., pH of about 7.0) at a ratio of 1:2. The formulation may comprise about 8.5% by weight the antimethanogenic statin (which is, in some embodiments, lovastatin, and in further embodiments, lovastatin lactone); about 42.4% by weight microcrystalline cellulose (e.g. Avicel PH102); about 4.2% by weight copovidone (e.g. Kollidon VA64 Fine); about 1.2% by weight silicon dioxide (e.g. Aerosil 200); about 0.6% by weight magnesium stearate; about 3.6% by weight crospovidone (e.g. Kollidon CL or Kollidon CL-F); about 3% by weight an enteric polymer that dissolves at a pH of about 5.5 (e.g. EUDRAGIT L 30 D-55+PlasACRYL HTP20); and about 6.1% by weight an enteric polymer that dissolves at a pH of about 7.0 (e.g. EUDRAGIT FS 30 D+PlasACRYL T20 and/or EUDRAGIT® S 100).

In another embodiment, the formulation of the present invention may at least one mini-tablet that releases at a first pH (e.g. pH of about 5.5) and at least one mini-tablet that releases at a second pH (e.g., pH of about 7.0) at a ratio of 1:5. In such embodiments, the formulation may comprise about 5-20% by weight the antimethanogenic statin (which is, in some embodiments, lovastatin, and in further embodiments, lovastatin lactone). For example, the antimethanogenic statin may be present at about 5%, about 6%, about 7%, about 8%, about 9%, about 10%, about 11%, about 12%, about 13%, about 14%, about 15%, about 16%, about 17%, about 18%, about 19%, or about 20% by weight of the entire formulation. In some embodiments, the formulation may further comprise about 30-60% by weight tablet diluent (e.g., about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, about 50%, about 51%, about 52%, about 53%, about 54%, about 55%, about 56%, about 57%, about 58%, about 59%, or about 60%). In some embodiments, the formulation may further comprise about 1-10% by weight tablet binder (e.g., about 1%, about 2%, about 3%, about 4%, about 5%, about 6%, about 7%, about 8%, about 9%, or about 10%). In some embodiments, the formulation may further comprise about 0.1-3.0% by weight viscosity and dispersion agent (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, the formulation may further comprise about 0.1-3.0% by weight lubricant, for example, to facilitate tableting (e.g., about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, or about 3.0%). In some embodiments, the formulation may further comprise about 1-10% by weight tablet disintegrant (e.g., about 1%, about 2%, about 3%, about 4%, about 5%, about 6%, about 7%, about 8%, about 9%, or about 10%). In some embodiments, the formulation may further comprise about 0.5-10% by weight an enteric polymer that dissolves at a pH of about 5.5 (e.g. EUDRAGIT L 30 D-55+PlasACRYL HTP20. For example, the enteric polymer that dissolves at a pH of about 5.5 may be present in the formulation at about 0.5%, about 0.6%, about 0.7%, about 0.8%, about 0.9%, about 1%, about 2%, about 3%, about 4%, about 5%, about 6%, about 7%, about 8%, about 9%, or about 10% by weight. In some embodiments, the formulation may further comprise about 1-15% by weight an enteric polymer that dissolves at a pH of about 7.0 (e.g. EUDRAGIT FS 30 D+PlasACRYL T20 and/or EUDRAGIT® S 100. For example, the enteric polymer that dissolves at a pH of about 7.0 may be present in the formulation at about 1%, about 2%, about 3%, about 4%, about 5%, about 6%, about 7%, about 8%, about 9%, about 10%, about 11%, about 12%, about 13%, about 14%, or about 15% by weight. In such embodiments, the antimethanogenic statin (which is, in some embodiments, lovastatin, and in further embodiments, lovastatin lactone) may be released in two doses. The first dose of antimethanogenic statin is encapsulated by the enteric polymer that dissolves at a pH of about 5.5; and the second dose of antimethanogenic statin is encapsulated by the enteric polymer that dissolves a at pH of about 7.0.

For example, the formulation may comprise at least one mini-tablet that releases at a first pH (e.g. pH of about 5.5) and at least one mini-tablets that release at a second pH (e.g., pH of about 7.0) at a ratio of 1:5. The formulation may comprise about 10% by weight the antimethanogenic statin (which is, in some embodiments, lovastatin, and in further embodiments, lovastatin lactone); about 50% by weight microcrystalline cellulose (e.g. Avicel PH102); about 5% by weight copovidone (e.g. Kollidon VA64 Fine); about 1% by weight silicon dioxide (e.g. Aerosil 200); about 0.5% by weight magnesium stearate; about 4% by weight crospovidone (e.g. Kollidon CL or Kollidon CL-F); about 2% by weight an enteric polymer that dissolves at a pH of about 5.5 (e.g. EUDRAGIT L 30 D-55+PlasACRYL HTP20); and about 9% by weight an enteric polymer that dissolves at a pH of about 7.0. (e.g. EUDRAGIT FS 30 D+PlasACRYL T20 and/or EUDRAGIT® S 100).

In another example, the formulation may comprise at least one mini-tablet that releases at a first pH (e.g. pH of about 5.5) and at least one mini-tablet that releases at a second pH (e.g., pH of about 7.0) at a ratio of 1:5. The formulation may comprise about 10% by weight the antimethanogenic statin (which is, in some embodiments, lovastatin, and in further embodiments, lovastatin lactone); about 50% by weight microcrystalline cellulose (e.g. Avicel PH102); about 5% by weight copovidone (e.g. Kollidon VA64 Fine); about 1.4% by weight silicon dioxide (e.g. Aerosil 200); about 0.7% by weight magnesium stearate; about 4.3% by weight crospovidone (e.g. Kollidon CL or Kollidon CL-F); about 1.8% by weight an enteric polymer that dissolves at a pH of about 5.5 (e.g. EUDRAGIT L 30 D-55+PlasACRYL HTP20); and about 8.9% by weight an enteric polymer that dissolves at a pH of about 7.0. (e.g. EUDRAGIT FS 30 D+PlasACRYL T20 and/or EUDRAGIT® S 100).

The therapeutic agents or their pharmaceutically acceptable salts which are used in accordance with the present invention may exhibit stereoisomerism by virtue of the presence of one or more asymmetric or chiral centers in the compounds. The present invention contemplates the various stereoisomers and mixtures thereof. Desired enantiomers can be obtained by chiral synthesis from commercially available chiral starting materials by methods well known in the art, or may be obtained from mixtures of the enantiomers by resolution using known techniques.

Solvate as used herein refers to a pharmaceutically acceptable solvate form of a specified therapeutic agent that retains the biological effectiveness of such agent. Examples of solvates include therapeutic agents of the invention in combination with, for example, water, isopropanol, ethanol, methanol, DMSO, ethyl acetate, acetic acid, or ethanolamine.

Prodrug, as used herein refers to a therapeutic agent that is converted under physiological conditions or by solvolysis or metabolically (e.g., in vivo) to a specified agent that is pharmaceutically active.

Active metabolite, as used herein refers to a pharmacologically active product produced through metabolism in the body of a specified therapeutic agent.

Co-crystal as used herein refers to a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates.

Administration and Dosage

It will be appreciated that the actual dose of the antimethanogenic statin to be administered according to the present invention will vary according to the particular compound, the particular dosage form, and the mode of administration. Many factors that may modify the action of the antimethanogenic statin (e.g., body weight, gender, diet, time of administration, route of administration, rate of excretion, condition of the subject, drug combinations, genetic disposition and reaction sensitivities) can be taken into account by those skilled in the art. Administration can be carried out continuously or in one or more discrete doses within the maximum tolerated dose. Optimal administration rates for a given set of conditions can be ascertained by those skilled in the art using conventional dosage administration tests.

Individual doses of the antimethanogenic statin can be administered in unit dosage forms (e.g., tablets or capsules) containing, for example, from about 0.01 mg to about 100 mg, from about 0.1 mg to about 100 mg, from about 0.1 mg to about 90 mg, from about 0.1 mg to about 80 mg, from about 0.1 mg to about 70 mg, from about 0.1 mg to about 60 mg, from about 0.1 mg to about 50 mg, from about 0.1 mg to about 40 mg active ingredient, from about 0.1 mg to about 30 mg, from about 0.1 mg to about 20 mg, from about 0.1 mg to about 10 mg, from about 0.1 mg to about 5 mg, from about 0.1 mg to about 3 mg, from about 0.1 mg to about 1 mg per unit dosage form, or from about 5 mg to about 80 mg per unit dosage form. For example, a unit dosage form can be about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, or about 100 mg, inclusive of all values and ranges therebetween. In an embodiment, individual dose of the antimethanogenic statin is administered in an unit dosage form containing 21 mg of the active ingredient. In another embodiment, individual dose of the antimethanogenic statin is administered in an unit dosage form containing 42 mg of the active ingredient.

In one embodiment, the antimethanogenic statin is administered at an amount of from about 0.01 mg to about 100 mg daily, an amount of from about 0.1 mg to about 100 mg daily, from about 0.1 mg to about 95 mg daily, from about 0.1 mg to about 90 mg daily, from about 0.1 mg to about 85 mg daily, from about 0.1 mg to about 80 mg daily, from about 0.1 mg to about 75 mg daily, from about 0.1 mg to about 70 mg daily, from about 0.1 mg to about 65 mg daily, from about 0.1 mg to about 60 mg daily, from about 0.1 mg to about 55 mg daily, from about 0.1 mg to about 50 mg daily, from about 0.1 mg to about 45 mg daily, from about 0.1 mg to about 40 mg daily, from about 0.1 mg to about 35 mg daily, from about 0.1 mg to about 30 mg daily, from about 0.1 mg to about 25 mg daily, from about 0.1 mg to about 20 mg daily, from about 0.1 mg to about 15 mg daily, from about 0.1 mg to about 10 mg daily, from about 0.1 mg to about 5 mg daily, from about 0.1 mg to about 3 mg daily, from about 0.1 mg to about 1 mg daily, or from about 5 mg to about 80 mg daily. In various embodiments, the antimethanogenic statin is administered at a daily dose of about 0.01 mg, about 0.02 mg, about 0.03 mg, about 0.04 mg, about 0.05 mg, about 0.06 mg, about 0.07 mg, about 0.08 mg, about 0.09 mg, about 0.1 mg, about 0.2 mg, about 0.3 mg, about 0.4 mg, about 0.5 mg, about 0.6 mg, about 0.7 mg, about 0.8 mg, about 0.9 mg, about 1 mg, about 2 mg, about 3 mg, about 4 mg, about 5 mg, about 6 mg, about 7 mg, about 8 mg, about 9 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, about 50 mg, about 51 mg, about 52 mg, about 53 mg, about 54 mg, about 55 mg, about 56 mg, about 57 mg, about 58 mg, about 59 mg, about 60 mg, about 61 mg, about 62 mg, about 63 mg, about 64 mg, about 65 mg, about 66 mg, about 67 mg, about 68 mg, about 69 mg, about 70 mg, about 71 mg, about 72 mg, about 73 mg, about 74 mg, about 75 mg, about 76 mg, about 77 mg, about 78 mg, about 79 mg, about 80 mg, about 81 mg, about 82 mg, about 83 mg, about 84 mg, about 85 mg, about 86 mg, about 87 mg, about 88 mg, about 89 mg, about 90 mg, about 91 mg, about 92 mg, about 93 mg, about 94 mg, about 95 mg, about 96 mg, about 97 mg, about 98 mg, about 99 mg, or about 100 mg, inclusive of all values and ranges therebetween. In an embodiment, the antimethanogenic statin is administered at an amount of 21 mg daily. In another embodiment, the antimethanogenic statin is administered at an amount of 42 mg daily.

In some embodiments, a suitable dosage of the antimethanogenic statin (e.g., a statin) is in a range of about 0.01 mg/kg to about 10 mg/kg of body weight of the subject, for example, about 0.01 mg/kg, about 0.02 mg/kg, about 0.03 mg/kg, about 0.04 mg/kg, about 0.05 mg/kg, about 0.06 mg/kg, about 0.07 mg/kg, about 0.08 mg/kg, about 0.09 mg/kg, about 0.1 mg/kg, about 0.2 mg/kg, about 0.3 mg/kg, about 0.4 mg/kg, about 0.5 mg/kg, about 0.6 mg/kg, about 0.7 mg/kg, about 0.8 mg/kg, about 0.9 mg/kg, about 1 mg/kg, about 1.1 mg/kg, about 1.2 mg/kg, about 1.3 mg/kg, about 1.4 mg/kg, about 1.5 mg/kg, about 1.6 mg/kg, about 1.7 mg/kg, about 1.8 mg/kg, 1.9 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg body weight, inclusive of all values and ranges therebetween. In other embodiments, a suitable dosage of the antimethanogenic statin is in a range of about 0.01 mg/kg to about 10 mg/kg of body weight, in a range of about 0.01 mg/kg to about 9 mg/kg of body weight, in a range of about 0.01 mg/kg to about 8 mg/kg of body weight, in a range of about 0.01 mg/kg to about 7 mg/kg of body weight, in a range of 0.01 mg/kg to about 6 mg/kg of body weight, in a range of about 0.05 mg/kg to about 5 mg/kg of body weight, in a range of about 0.05 mg/kg to about 4 mg/kg of body weight, in a range of about 0.05 mg/kg to about 3 mg/kg of body weight, in a range of about 0.05 mg/kg to about 2 mg/kg of body weight, in a range of about 0.05 mg/kg to about 1.5 mg/kg of body weight, or in a range of about 0.05 mg/kg to about 1 mg/kg of body weight.

In accordance with certain embodiments of the invention, the antimethanogenic statin may be administered, for example, more than once daily, about once per day, about every other day, about every third day, about once a week, about once every two weeks, about once every month, about once every two months, about once every three months, about once every six months, or about once every year.

In various embodiments, the antimethanogenic statin may be administered in a patient that is fasting. In various embodiments, the antimethanogenic statin may be administered in a patient with a meal. In various embodiments, the antimethanogenic statin may be administered in a patient that is postprandial. In various embodiments, patient is on an elemental diet. A comestible total enteral nutrition (TEN) formulation, which is also called an "elemental diet" are commercially available, for example, VIVONEX T.E.N. (Nestle) and its variants, or the like. A useful total enteral nutrition formulation satisfies all the subject's nutritional requirements, containing free amino acids, carbohydrates, lipids, and all essential vitamins and minerals, but is in a form that is readily absorbable in the upper gastrointestinal tract, thus depriving or "starving" the methanogen syntrophic microorganism of nutrients of at least some of the nutrients they use for proliferating. Thus, methanogen syntrophic microorganism growth is inhibited.

Additional Agents and Combination Therapy or Co-Formulation/Patient Selection

Administration of the present formulations may be combined with additional therapeutic agents. Co-administration of the additional therapeutic agent and the present formulations may be simultaneous or sequential. Further the present formulations may comprise an additional therapeutic agent (e.g. via co-formulation).

In some embodiments, the modified-release formulations of the present invention are administered in combination with an additional therapeutic agent. In an embodiment, the additional therapeutic agent and the antimethanogenic statin are combined into a single modified-release formulation. In some embodiments, the methods of treatment and/or prevention comprise administering the modified-release formulations of the present invention to a subject that is undergoing treatment with an additional therapeutic agent.

In one embodiment, the additional agent and the antimethanogenic statin are administered to a subject simultaneously. The term "simultaneously" as used herein, means that the additional agent and the antimethanogenic statin are administered with a time separation of no more than about 60 minutes, such as no more than about 30 minutes, no more than about 20 minutes, no more than about 10 minutes, no more than about 5 minutes, or no more than about 1 minute. Administration of the additional agent and the antimethanogenic statin can be by simultaneous administration of a single formulation (e.g., a formulation comprising the additional agent and the antimethanogenic statin) or of separate formulations (e.g., a first formulation including the additional agent and a second formulation including the antimethanogenic statin).

Co-administration does not require the additional therapeutic agents to be administered simultaneously, if the timing of their administration is such that the pharmacological activities of the additional agent and the antimethanogenic statin overlap in time, thereby exerting a combined therapeutic effect. For example, the additional agent and the antimethanogenic statin can be administered sequentially. The term "sequentially" as used herein means that the additional agent and the antimethanogenic statin are administered with a time separation of more than about 60 minutes. For example, the time between the sequential administration of the additional agent and the antimethanogenic statin can be more than about 60 minutes, more than about 2 hours, more than about 5 hours, more than about 10 hours, more than about 1 day, more than about 2 days, more than about 3 days, or more than about 1 week apart. The optimal administration times will depend on the rates of metabolism, excretion, and/or the pharmacodynamic activity of the additional agent and the antimethanogenic statin being administered. Either the additional agent or the antimethanogenic statin may be administered first.

In a further embodiment, the additional therapeutic agent and the antimethanogenic statin are administered to a subject simultaneously but the release of additional therapeutic agent and the antimethanogenic statin from their respective dosage forms (or single unit dosage form if co-formulated) in the GI tract occurs sequentially.

Co-administration also does not require the additional therapeutic agents to be administered to the subject by the same route of administration. Rather, each therapeutic agent can be administered by any appropriate route, for example, parenterally or non-parenterally.

The formulations of the present invention may comprise a pharmaceutically acceptable excipient. In some embodiments, the formulation may further include agent which prevents or reduces lactone ring-opening, such as an esterase inhibitor (e.g. grapefruit juice or components naringenin, kaempferol) and/or a paraoxonase inhibitor (e.g. PON1 or PON3 inhibitor). In some embodiments, the esterase inhibitor and/or a paraoxonase inhibitor is one or more of amiodarone, anastrozole, azithromyzcin, cannabinoids, cimetidine, clarithromycin, clotrimazolem, cyclosporine, danazol, delavirdine, dexamethasone, diethyldithiocarbamate, diltiazem, dirithyromycin, disulfiram, entacapone, erythromycin, ethinyl estradiol, fluconazole, fluoxetine, fluvoaxamine, gestodene, grapefruit juice, indinavir, isoniazid, ketoconazole, metronidazole, mibefradil, miconazole, nefazodone, nelfinavir, nevirapine, norfloxacin, norfluoxetine, omeprazole, oxiconazole, paroxetine, propoxyphene, quinidine, quinine, quinupristine and dalfopristin, ranitidine, ritonavir, saquinavir, sertindole, sertraline, troglitazone, troleandomycin, valproic acid and/or a lactam agent selected from oxindole, isatin, δ-valerolactam, ε-caprolactam, 2-hydroxyquinoline, and 3,4-dihydro-2(1H)-quinoline and N-bromo-ε-caprolactam.

In various embodiments, the modified-release formulation of the present invention is administered in combination with an inhibitor of the organic anion transporting polypeptide (OATP) transporter. In an embodiment, the OATP inhibitor and the antimethanogenic statin are combined into a single modified-release formulation. Without wishing to be bound by theory, it is believed that inclusion of the OATP inhibitor minimizes absorption of the antimethanogenic statin from the intestine and/or reduces the enterohepatic recirculation of the antimethanogenic statin, thereby maximizing retention of the antimethanogenic statin in the intestine and minimizing any potential systemic side effects of the antimethanogenic statin. Illustrative OATP inhibitors include, but are not limited to, grapefruit juice or grapefruit juice constituents such as naringin and hesperidin, orange juice and orange juice constituents, apple juice and apple juice constituents, and green tea and green tea extracts such as epicatechin gallate (ECG), epigallocatechin gallate (EGCG). In an embodiment, the OATP inhibitor is released in the intestine prior to release of the antimethanogenic statin.

In one embodiment, the additional therapeutic agent is a prokinetic agent that facilitates movement of a mass through the intestinal tract. Illustrative prokinetic agents include, but are not limited to, prucalopride (e.g. RESOLOR) or a macrolide antibiotic such as erythromycin. In another embodiment, the additional therapeutic agent is a natural product such as peppermint oil, which alleviates abdominal pain.

The present invention also contemplates the use of additional therapeutic agent that are useful for treating constipation such as, for example, laxatives, guanylate cyclase C agonist (e.g., linaclotide), a serotonin agonist (e.g., prucalorpride, tegaserod), a chloride channel agonist (e.g., lubiprostone), and combinations thereof.

In some embodiments, the additional therapeutic agent is an agent useful for treating IBS (including IBS-C). In some embodiments, the additional therapeutic agent is a selective chloride channel activator, including, for example, molecules derived from prostaglandins such as lubiprostone (e.g. AMITIZA) and those compounds described in U.S. Pat. Nos. 5,284,858, 6,414,016 and 6,583,174, the contents of which are hereby incorporated by reference in their entireties. In some embodiments, the additional therapeutic agent is an agent, including a peptide agent, that increases the secretion of chloride and/or water in the intestines and/or soften stools and/or stimulate bowel movements, such as, for example, linaclotide (e.g. LINZESS) and those compounds described in U.S. Pat. No. 7,304,036, the contents of which are hereby incorporated by reference in their entirety. In some embodiments, the additional therapeutic agent is an agent that relaxes the colon and/or slows the movement of waste through the lower bowel. In some embodiments the additional therapeutic agent is a 5-$HT_3$ antagonist, including, but not limited to, alosetron (e.g. LOTRONEX).

In some embodiments, the additional therapeutic agent is a small molecule that acts as a peripherally selective κ-opioid agonist, such as, for example, EMD-61753 ((N-methyl-N-[(1S)-1-phenyl-2-((3S)-3-hydroxypyrrolidin-1-yl)-ethyl]-2,2-diphenyl-acetamide hydrochloride, ASMADOLINE) and those compounds described in U.S. Pat. No. 6,344,566, the contents of which are hereby incorporated by reference in their entirety. In some embodiments, the additional therapeutic agent is a cholecystokinin antagonist, e.g. one selective for the $CCK_A$ subtype and/or inhibits gastrointestinal motility and reduces gastric secretions, such as, for example, Dexloxiglumide ((4R)-4-[(3,4-dichlorobenzoyl)amino]-5-(3-methoxypropylpentylamino)-5-oxopentanoic acid) and those compounds described in U.S. Pat. No. 5,602,179, the contents of which are hereby incorporated by reference in their entirety. In some embodiments, the additional therapeutic agent is tapentadol (1R,2R)-3-(3-dimethylamino-1-ethyl-2-methyl-propyl)-phenol), as described in US Patent Publication No. 2013/0116334, the contents of which are hereby incorporated by reference in their entirety In some embodiments, the additional therapeutic agent is a laxative, including but not limited to osmotic laxatives (such as, for example, magnesium carbonate, magnesium hydroxide (e.g. Milk of Magnesia), magnesium oxide, magnesium peroxide, magnesium sulfate, lactulose, lactitol, sodium sulfate, pentaerythritol, macrogol, mannitol, sodium phosphate, sorbitol, magnesium citrate, sodium tartrate, laminarid, and polyethylene glycol (e.g., macrogol-containing products, such as MOVICOL and polyethylene glycol 3350, or SOFTLAX, MIRALAX, DULCOLAX BAL- ANCE, CLEARLAX, OSMOLAX OR GLYCOLAX, GOLYTELY, GAVILYTE C, NULYTELY, GLYCOLAX, FORTRANS, TRILYTE, COLYTE, HALFLYTELY, SOFTLAX, LAX-A-DAY, CLEARLAX AND MOVIPREP). In some embodiments, the additional therapeutic agent is a laxative, including but not limited to stimulant laxatives (such as, for example, SENOKOT). Also provided are contact laxatives (e.g. oxyphenisatine, bisacodyl, dantron, phenolphthalein, castor oil, senna glycosides, cascara, sodium picosulfate, and bisoxatin) and bulk-forming laxatives (e.g. ispaghula, ethulose, sterculia, linseed, methylcellulose, triticum, and polycarbophil calcium). In some embodiments, the additional therapeutic agent is an enema, such as, for example, sodium laurilsulfate, sodium phosphate, bisacodyl, dantron, glycerol, oil, and sorbitol. Peripheral opioid antagonists such as, for example, alvimopan and methylnaltrexone, as well as prostaglandins such as, for example, lubiprostone are also additional therapeutic agents in some embodiments. Also, linaclotide, prucalopride, and tegaserod may be additional therapeutics.

In some embodiments, the additional therapeutic agent is an agent used for long-term pain and cramping, including but not limited to anticholinergics (antispasmodics), such as, for example, dicyclomine (BENTYL) and or antidepressants, including, for example, desipramine (such as, for example, NORPRAMIN), imipramine (TOFRANIL) or nortriptyline (PAMELOR), which are optionally administered at low doses. In low doses, they can help with pain caused by IBS.

In some embodiments, the additional therapeutic agent is fiber supplement, such as, for example, psyllium (METAMUCIL) or methylcellulose (CITRUCEL).

In some embodiments, the additional therapeutic agent is an agent useful for treating obesity. Illustrative agents include, but are not limited to, orlistat, loracaserin, phentermine-topiramate, sibutramine, rimonabant, exenatide, pramlintide, phentermine, benzphetamine, diethylpropion, phendimetrazine, bupropion, and metformin. In various embodiments, the additional agent is an agent that that interfere with the body's ability to absorb specific nutrients in food, such as orlistat, glucomannan, and guar gum. Agents that suppress appetite are also among the additional agents, e.g. catecholamines and their derivatives (such as phentermine and other amphetamine-based drugs), various anti-depressants and mood stabilizers (e.g. bupropion and topiramate), anorectics (e.g. dexedrine, digoxin). Agents that increase the body's metabolism are also among the additional agents. In some embodiments, additional agents may be selected from among appetite suppressants, neurotransmitter reuptake inhibitors, dopaminergic agonists, serotonergic agonists, modulators of GABAergic signaling, anticonvulsants, antidepressants, monoamine oxidase inhibitors, substance P (NK1) receptor antagonists, melanocortin receptor agonists and antagonists, lipase inhibitors, inhibitors of fat absorption, regulators of energy intake or metabolism, cannabinoid receptor modulators, agents for treating addiction, agents for treating metabolic syndrome, peroxisome proliferator-activated receptor (PPAR) modulators; and dipeptidyl peptidase 4 (DPP-4) antagonists. In some embodiments, additional agents may be selected from among amphetamines, benzodiazepines, sulfonyl ureas, meglitinides, thiazolidinediones, biguanides, beta-blockers, ACE inhibitors, diuretics, nitrates, calcium channel blockers, phenlermine, sibutramine, lorcaserin, cetilistat, rimonabant, taranabant, topiramate, gabapentin, valproate, vigabatrin, bupropion, tiagabine, sertraline, fluoxetine, trazodone, zonisamide, methylphenidate, varenicline, naltrexone, diethylpropion, phendimetrazine, repaglinide, nateglinide, glimepiride, pioglitazone, rosiglilazone, and sitagliptin.

In an embodiment, the additional therapeutic agent is an agent for treating prediabetes, diabetes, type II diabetes, insulin resistance, glucose intolerance, or hyperglycemia. Examples of drugs include, but are not limited to, alpha-glucosidase inhibitors, amylin analogs, dipeptidyl peptidase-4 inhibitors, GLP1 agonists, meglitinides, sulfonylureas, biguanides, thiazolidinediones (TZD), and insulin. Additional examples of such agents include bromocriptine and Welchol. Examples of alpha-glucosidase inhibitors include but are not limited to acarbose and miglitol. An example of an amylin analog is pramlintide. Examples of dipeptidyl peptidase-4 inhibitors include but are not limited to saxagliptin, sitagliptin, vildagliptin, linagliptin, and alogliptin. Examples of GLP1 agonist include but are not limited to liraglutide, exenatide, exenatide extended release. Examples of meglitinides include but are not limited to nateglinide, and repaglinide. Examples of sulfonylureas include but are not limited to chlorpropamide, glimepiride, glipizide, glyburide, tolazamide, and tolbutamide. Examples of biguanides include but are not limited to metformin, Riomet, Glucophage, Glucophage XR, Glumetza. Examples of thiazolidinedione include but are not limited to rosiglitazone and pioglitazone. Examples of insulin include but are not limited to Aspart, Detemir, Glargine, Glulisine, and Lispro. Examples of combination drugs include but are not limited to glipizide/metformin, glyburide/metformin, pioglitazone/glimepiride, pioglitazone/metformin, repaglinide/metformin, rosiglitazone/glimepiride, rosiglitazone/metformin, saxagliptin/metformin, sitagliptin/simvastatin, sitagliptin/metformin, linagliptin/metformin, alogliptin/metformin, and alogliptin/pioglitazone.

In another embodiment, the additional therapeutic agent is a probiotic. In some embodiments, enteric dietary formulations containing low residual material, such as pre-digested or basic amino acid formulations and other methods and products as described in U.S. Pat. No. 8,110,177 (the contents of which are incorporated herein by reference) may be employed. In a further embodiment, such low residual enteric dietary formulations may be formulated in low carbohydrate and low fat forms either with or without immediate or sustained release statins or red yeast rice which may be particularly useful for weight loss and diabetes. In various embodiments, the probiotic may comprise the following illustrative cells: *E. coli* Nissle 1917, a *lactobacillus* (e.g. *acidophilus, Lactobacillus brevis, L. bulgaricus, L. plantarum, L. rhamnosus, Rhamnosus L. fermentum, L. caucasicus, L. helveticus, L. lactis, L. reuteri* and *L. casei*) or a bifidobacteria (*Bifidobacterium bifidum, B. infantis*) *Streptococcus thermophiles*, and *Enterococcus faecium*. Other suitable probiotics and prebiotics are disclosed for example in R. Spiller, *Aliment Pharmacol Ther* 28, 385-396, the contents of which are hereby incorporated by reference in their entirety.

In some embodiments, a probiotic agent that optionally inhibits the growth of methanogens, for example, *Bifidobacterium* spp. or *Lactobacillus* species or strains, e.g., *L. acidophilus, L. rhamnosus, L. plantarum, L. reuteri, L. paracasei* subsp. *paracasei*, or *L. casei Shirota*, or probiotic *Saccharomyces* species, e.g., *S. cerevisiae*, is selected and/or administered. The probiotic agent that inhibits methanogenesis may be administered in a pharmaceutically acceptable ingestible formulation, such as in a capsule, or for some subjects, consuming a food supplemented with the inoculum is effective, for example a milk, yogurt, cheese, meat or other fermentable food preparation. Probiotic agents can inhibit the growth of methanogens, for example, by competing against methanogens for growth and thus reduce or inhibit the growth of methanogens.

Methods of Treatment

In one aspect, the present invention provides methods of treating or preventing a methanogen-associated disorder by administering a modified-release formulation comprising at least one anti-methanogenic agent, such as an antimethanogenic statin as described herein to the intestine (i.e., small and/or large intestine) in a subject in need thereof.

In some embodiments, the methanogen-associated disorder is a disease or disorder or condition caused by, resulted from, or related to one or more of the abnormal presence or absence of methanogens, abnormal levels of methanogens, overgrowth of methanogens, elevated levels of methanogenesis, elevated enteric methane levels, excessive hydrogen scavenging by hydrogen-consuming methanogens or colonization of methanogens in an abnormal location (e.g., in the small bowel rather than large bowel), either alone or in combination with non-methanogen syntrophic organisms.

Illustrative methanogen-associated disorders include, but are not limited to, enteric methanogen colonization, IBS, IBS-C, IBS-M, constipation, diabetes, type 2 diabetes, metabolic syndrome, insulin resistance, metabolic syndrome, obesity, constipation, chronic constipation, chronic intestinal pseudo-obstruction, systemic sclerosis, systemic lupus, erythematosus, dermatomysitis/polymyositis, periartiytis nodosa, mixed connective tissue disorder, rheumatoid arthritis, spinal cord injury, Parkinson's disease, hypothyroidism/hypoparathyroidism, Hirschsprung's disease, Chagas' disease, intestinal hypoganglionosis, and Ehlers-Danlos Syndrome.

In one aspect, the present invention provides methods of reducing or eliminating the production and/or accumulation of methane in the GI tract by administering a modified-release formulation comprising at least one anti-methanogenic agent, such as an antimethanogenic statin as described herein to the intestine (e.g. the small and/or large intestine) of a subject in need thereof. In another aspect, the present invention provides methods of reducing or eliminating methane, for example as produced by a methanogen in the GI tract by administering a modified-release formulation comprising at least one anti-methanogenic agent, such as an antimethanogenic statin as described herein to the intestine (i.e., small and/or large intestine) of a subject in need thereof.

In various embodiments, the methanogen is a microorganism that produces methane as a metabolic byproduct. Methanogens are classified as archaea. Examples of methanogens include but are not limited to *Methanobacterium bryantii, Methanobacterium formicum, Methanobrevibacter arboriphilicus, Methanobrevibacter gottschalkii, Methanobrevibacter ruminantium, Methanobrevibacter smithii, Methanocalculus chunghsingensis, Methanococcoides burtonii, Methanococcus aeolicus, Methanococcus deltae, Methanococcus jannaschii, Methanococcus maripaludis, Methanococcus vannielii, Methanocorpusculum labreanum, Methanoculleus bourgensis (Methanogenium olentangyi, Methanogenium bourgense), Methanoculleus marisnigri, Methanofollis liminatans, Methanogenium cariaci, Methanogenium frigidum, Methanogenium organophilum, Methanogenium wolfei, Methanomicrobium mobile, Methanopyrus kandleri, Methanoregula boonei, Methanosaeta concilii, Methanosaeta thermophile, Methanosarcina acetivorans, Methanosarcina barkeri, Methanosarcina mazei, Methanosphaera stadtmanae, Methanospirillium hungatei, Methanothermobacter defluvii (Methanobacterium defluvii),* *Methanothermobacter thermautotrophicus (Methanobacterium thermoautotrophicum), Methanothermobacter thermoflexus (Methanobacterium thermoflexum), Methanothermobacter wolfei (Methanobacterium wolfei),* and *Methanothrix sochngenii.*

In one aspect, the present invention provides methods of reducing or eliminating methane produced by *Methanobrevibacter smithii* in the GI tract. In another aspect, the present invention provides methods of reducing or eliminating methane produced by *Methanobrevibacter smithii,* in the GI tract by administering a modified-release formulation comprising at least one anti-methanogenic agent, such as an antimethanogenic statin as described herein to the intestine (i.e., small and/or large intestine) in a subject in need thereof. In some embodiments, administration of the modified-release formulation comprising at least one anti-methanogenic agent reduces or eliminates methane produced by *Methanobrevibacter smithii* in the small intestines (e.g., one or more of duodenum, jejunum, ileum). In an embodiment, administration of the modified-release formulation comprising at least one anti-methanogenic agent reduces or eliminates methane produced by *Methanobrevibacter smithii* in the ileum. In some embodiments, administration of the modified-release formulation comprising at least one anti-methanogenic agent reduces or eliminates methane produced by *Methanobrevibacter smithii* in the large intestine (e.g., one or more of cecum, ascending, transverse, descending or sigmoid portions of the colon, and rectum).

In one aspect, the present invention provides methods of reducing or eliminating the methane derived from *Methanobrevibacter smithii* in the GI tract. In another aspect, the present invention provides methods of reducing or eliminating methane, for example as produced by *Methanobrevibacter smithii,* in the GI tract by administering a modified-release formulation comprising at least one anti-methanogenic agent, such as an antimethanogenic statin as described herein to the intestine (i.e., small and/or large intestine) in a subject in need thereof.

In various embodiments, the present invention relates to the substantial reduction of methane gas in a subjects GI tract (e.g. eradication of intestinal methane). In some embodiments the present formulations and methods prevent the increase in levels of methane gas in a subject's GI tract. In some embodiments, the patient's GI methane levels (as assessed by methods described herein and methods known in the art) are reduced to about 1 ppm, or about 2 ppm, or about 3 ppm, or about 4 ppm, or about 5 ppm, or about 10 ppm, or about 15 ppm, or about 20 ppm, or about 25 ppm, or about 30 ppm, or about 35 ppm, or about 40 ppm, or about 45 ppm, or about 50 ppm, or about 55 ppm, or about 60 ppm, or about 65 ppm, or about 70 ppm, or about 75 ppm, or about 80 ppm, or about 85 ppm, or about 90 ppm, or about 100 ppm. In various embodiments, the present formulations and methods reduce the patient's GI methane levels to less than about 250 ppm, or less than about 225 ppm, or less than about 200 ppm, or less than about 175 ppm, or less than about 150 ppm, or less than about 125 ppm, or less than about 100 ppm, or less than about 50 ppm. In various embodiments, substantial reduction of methane gas is not accompanied by a substantial reduction in hydrogen gas.

In various embodiments, the present invention relates to the treatment of IBS, including IBS-C as described by ICD-10 (International Statistical Classification of Diseases and Related Health Problems, WHO edition). In various embodiments, the present invention relates to the treatment of irritable colon, as classified in ICD-10 as [K58]. IBS may include irritable bowel syndrome without diarrhea, as classified in ICD-10 as [K58.9]. Irritable bowel syndrome without diarrhea may also include irritable bowel syndrome not otherwise specified (NOS). Further, the diseases as classified in ICD-10 as K59 are also included (e.g. constipation; K59.1 Functional diarrhea; K59.2 Neurogenic bowel, not elsewhere classified; K59.3 Megacolon, not elsewhere classified (including dialatation of colon, toxic megacolon, megacolon in Chagas disease (B57.3), congenital (aganglionic) (Q43.1), and Hirschsprung disease (Q43.1)); K59.4 Anal spasm (including Proctalgia fugax); K59.8 Other specified functional intestinal disorders (including atony of colon) and K59.9 Functional intestinal disorder, unspecified).

In various embodiments, the present invention relates to the treatment of spastic colon, nervous colitis, mucous colitis, functional colitis or colonic neurosis. In various embodiments, the present invention relates to the treatment of diseases that have been described as sigma elongatum mobile, cecum mobile, chronic colitis, splanchnoptosia and the like. Typological classification of the disease generally include convulsive large bowel, diarrhea nervosa and colica mucosa, and the disease may also be classified in convulsive constipation type, atonic constipation type, intestinal gas syndrome, or chronic celiopathy.

Furthermore, IBS may also include cholangiodyskinesia, gastric emptying hypofunction, hysteric globus, non-specific esophagus functional abnormalities, nervous vomiting, recurrent abdominal pain, simple constipation, chronic idiopathic constipation and the like. As diagnostic criteria of IBS those of NIH, Manning, Cook et al. and the like are suitable (see Asakura, *Clinical Digestive Internal Medicine*, 8 (8): 1373-1381 (1993), the contents of which are hereby incorporated by reference in their entirety).

In various embodiments, the present invention relates to the treatment of IBS, including IBS-C of varying stages or severity. In one embodiment, stages or severity of the IBS may be evaluated with a health-related quality of life (HRQoL) evaluation. In some embodiments, the stage or severity of the disease in the patient to be treated is assessed by an evaluation of one or more of patient pain, distension, bowel dysfunction and quality of life/global well-being.

In some embodiments, the stage or severity of the disease in the patient to be treated is assessed by the Rome Scale (for the last 3 months with symptom onset at least 6 months prior to diagnosis: recurrent abdominal pain or discomfort (e.g. uncomfortable sensation not described as pain.) at least 3 days/month in the last 3 months associated with two or more of improvement with defecation, onset associated with a change in frequency of stool, and onset associated with a change in the form (appearance) of stool. In various embodiments, the present compositions and methods provide patient improve as assessed by the Rome Scale.

In some embodiments, the stage or severity of the disease in the patient to be treated is assessed by abdominal pain intensity score of 0-10. In various embodiments, values ≥3 are considered to be suffering from pain requiring treatment. In various embodiments, the patient has an abdominal pain intensity score of great than about 9, or about 8, or about 7, or about 6, or about 5, or about 4, or about 3. In various embodiments, the present compositions and methods reduce the abdominal pain intensity score by about 1, or about 2, or about 3, or about 4, or about 5, or about 6, or about 7, or about 8, or about 9, or about 10.

In some embodiments, the stage or severity of the disease in the patient to be treated is assessed by the Kruis scale (*Gastroenterology* 87: 1-7, the contents of which are hereby incorporated by reference). This scale incorporates both the "cardinal" symptoms (pain, bloating, altered bowel function) and "red flag" signs of potential underlying organic disease that would thus exclude an IBS diagnosis. IBS is diagnosed if the sum of scores >44.

TABLE 1

Kruis Scoring System. IBS is diagnosed if the sum of scores > 44.

| Parameter | Score |
|---|---|
| Signs | |
| Pain, flatulence, or bowel irregularity | 34 |
| Duration of symptoms > 2 yr | 16 |
| Description of abdominal pain (Scale from burning to "not so bad") | 23 |
| Alternating diarrhea and constipation | 14 |
| Red Flags | |
| Abnormal physical findings or history pathognomonic of other disease | −47 |
| ESR > 10 mm/h | −13 |
| WBC > ×10$^9$ | −50 |
| Anemia | −98 |
| History of blood in stool | −98 |

In some embodiments, the patient is evaluated with the assessment described in Francis, et at *Aliment Pharmacol Ther* 1997; 11: 395-402, the contents of which are hereby incorporated by reference in their entirety. For instance, a scoring system based on patient ranking of pain, distension, bowel dysfunction and quality of life/global well-being on a scale of up to 500 is used. Mild, moderate and severe cases were indicated by scores of 75 to 175, 175 to 300 and >300. In some embodiments, the patient of the present invention has a score of 75 to 175. In some embodiments, the patient of the present invention has a score of 175 to 300. In some embodiments, the patient of the present invention has a score of >300. In some embodiments the scales described in Wong and Drossman (*Expert Rev. Gastroenterol. Hepatol.* 4(3), (2010), the contents of which are hereby incorporated by reference in their entirety). For example, in some embodiments, the patients of the present invention are evaluated for the parameters of dysphoria, activity interference, body image, health worry, food avoidance, social reaction, and sexual relationships and optionally scored on a 0-100 as described on the Patrick scale; and/or the patients of the present invention are evaluated for the parameters of daily activities, emotional impact, family relations, food, sleep and fatigue, social impact, sexual relations symptoms and optionally scored on a 0-216 as described on the Groll scale; the patients of the present invention are evaluated for the parameters of activities, anxiety, diet, sleep, discomfort, health perception, disease coping and stress and optionally scored on a 0-100 as described on the Chassany scale; the patients of the present invention are evaluated for the parameters of emotional health, mental health, sleep, energy, physical functioning, diet, social role, physical role, and sexual relations and optionally scored on a 0-100 as described on the Hahn scale; and/or the patients of the present invention are evaluated for the parameters of bowel symptoms, fatigue, activity impairment, emotional dysfunction and optionally scored as domain average scores (calculated by dividing the domain sum score by the number of items: range 1-7) as described on the Wong scale.

In some embodiments, patients may be stratified based on one or more of methane detection (e.g. via breath test) and methanogen detection (e.g. via PCR, e.g. qPCR). In some embodiments, the patient is considered methane breath test positive if the subject presents with greater than about 3 ppm methane. In some embodiments, the patient of the present invention has greater than about $10^4$, or about $10^5$, or about $10^6$ copies of *M. smithii* per grams of wet stool. In some embodiments, the patient of the present invention is defined by a measurement of the fractional methanogen contribution to the total microbial content of the feces. In some embodiments, the patient has greater than about 0.5%, or about 0.6%, or about 0.7%, or about 0.8%, or about 0.9%, or about 1.0%, or about 1.1%, or about 1.2%, or about 1.3%, or about 1.4%, or about 1.5%, or about 2.5% M *smithii* fraction of the total microbial content of the feces.

In various embodiments, the present invention provides methods for inhibiting or reducing methanogenesis, including in subjects afflicted with one or more of IBS-C, obesity and diabetes, in which a subject is evaluated as a responder or a non-responder and treated accordingly. For example, in some embodiments, a subject may be evaluated for a baseline level of intestinal methane. Such a measurement may use any of the techniques described herein, including without limitation methane breath testing. Subsequently the subject is administered one or more of the formulations described herein for an initial treatment period of less than about 1 week (e.g. about 1 day, or about 2 days, or about 3 days, or about 4 days, or about 5 days, or about 6 days, or about 7 days) and then re-evaluated for a post-initial treatment level of intestinal methane. Such a measurement may use any of the techniques described herein, including without limitation methane breath testing. This second evaluation allows classification of subjects as responders or non-responders; for example responders show a reduction in post-initial treatment level of intestinal methane while non-responders do not. Accordingly, in some embodiments, responders are administered a full treatment period of a one or more of the formulations described herein (e.g. administration for weeks, months, years and even life of the patient, inclusive of chronic administration). Further, in some embodiments, non-responders are not administered a full treatment period of a one or more of the formulations described herein and instead are treated with an alternative therapy.

In various embodiments, the present invention provides methods of treating constipation in a subject. In various embodiments, the subject is evaluated as a responder or a non-responder and treated accordingly. For example, in some embodiments, a subject may be evaluated for a baseline level of intestinal methane. Such a measurement may use any of the techniques described herein, including without limitation methane breath testing. Subsequently, the subject is administered one or more of the formulations described herein for an initial treatment period of less than about 1 week (e.g. about 1 day, or about 2 days, or about 3 days, or about 4 days, or about 5 days, or about 6 days, or about 7 days) and then re-evaluated for a post-initial treatment level of intestinal methane. Such a measurement may use any of the techniques described herein, including without limitation methane breath testing. This second evaluation allows for classification of subjects as responders or non-responders; for example responders show a reduction in post-initial treatment level of intestinal methane while non-responders do not. Accordingly, in some embodiments, responders are administered a full treatment period of a one or more of the formulations described herein (e.g. administration for weeks, months, years and even life of the patient, inclusive of chronic administration). Further, in some embodiments, non-responders are not administered a full treatment period of a one or more of the formulations described herein and instead are treated with an alternative therapy.

In various embodiments, the present invention provides methods of treating various methanogen-associated disorders, including by way of non-limiting example IBS-C, in which a subject is evaluated as a responder or a non-responder and treated accordingly. For example, in some embodiments, a subject may be evaluated for a baseline level of intestinal methane. Such a measurement may use any of the techniques described herein, including without limitation methane breath testing. Subsequently, the subject is administered one or more of the formulations described herein for an initial treatment period of less than about 1 week (e.g. about 1 day, or about 2 days, or about 3 days, or about 4 days, or about 5 days, or about 6 days, or about 7 days) and then re-evaluated for a post-initial treatment level of intestinal methane. Such a measurement may use any of the techniques described herein, including without limitation methane breath testing. This second evaluation allows of classification of subjects as responders or non-responders; for example responders show a reduction in post-initial treatment level of intestinal methane while non-responders do not. Accordingly, in some embodiments, responders are administered a full treatment period of a one or more of the formulations described herein (e.g. administration for weeks, months, years and even life of the patient, inclusive of chronic administration). Further, in some embodiments, non-responders are not administered a full treatment period of a one or more of the formulations described herein and instead are treated with an alternative therapy.

In various embodiments, the present invention provides methods for identifying a patient that is likely to respond to long term (including chronic) treatment one or more of the formulations described herein for the treatment of one or more of inhibiting or reducing methanogenesis, including in subjects afflicted with one or more of IBS-C, obesity and diabetes; treating constipation; and treating various methanogen-associated disorders, including by way of non-limiting example IBS-C. In various embodiments, the methods include the steps of evaluating a subject for a baseline level of intestinal methane (e.g. using any of the techniques described herein, including without limitation methane breath testing); administering one or more of the formulations described herein for an initial treatment period of less than about 1 week (e.g. about 1 day, or about 2 days, or about 3 days, or about 4 days, or about 5 days, or about 6 days, or about 7 days); and re-evaluating the subject for a post-initial treatment level of intestinal methane (e.g. using any of the techniques described herein, including without limitation methane breath testing). This re-evaluation allows of classification of subjects as responders or non-responders; for example responders show a reduction in post-initial treatment level of intestinal methane while non-responders do not. Responders are those patients that are likely to respond to long term (including chronic) treatment one or more of the formulations described herein for the treatment of one or more of inhibiting or reducing methanogenesis, including in subjects afflicted with one or more of C-IBS, obesity and diabetes; treating constipation; and treating various methanogen-associated disorders, including by way of non-limiting example C-IBS.

In some embodiments, methods of the present invention treat or prevent constipation. Constipation may be associated with, for example, chemotherapy, vinca alkaloids, oxaliplatins, taxanes, thalidomide, opioids, sedatives, anticholinergics, gastrointestinal antispasmodics, antiparkinsonism agents, antidepressants, phenothiazines, calcium- and aluminum-based antacids, diuretics, tranquilizers, sleeping medications, general anesthesia, pudendal blocks, inadequate fluid intake, excessive use of laxatives and/or enemas, prolonged immobility, inadequate exercise. spinal cord injury or compression, fractures, fatigue, weakness, inactivity, bedrest, cardiac problems, diverticulitis, neurological lesions, cerebral tumors, spinal cord injury, spinal cord compression, paraplegia, cerebrovascular accident with paresis, weak abdominal muscles, hypothyroidism, lead poisoning, uremia, dehydration, hypercalcemia, hypokalemia, hyponatremia, anorexia, immobility, antidepressants, inability to increase intra-abdominal pressure, emphysema, neuromuscular impairment of the diaphragm, neuromuscular impairment of abdominal muscles, abdominal hernias, malnutrition, cachexia, anemia, carcinoma, and senility. In some embodiments, methods of the invention increase the number of bowel movements in a subject suffering from constipation. For example, methods of the invention may increase the number of bowel movements in the subject by at least 1, 2, 3, 4, or 5 movements per week. In some embodiments, methods of the invention increase the stool wet weight in a subject suffering from constipation. For example, the methods of the invention may increase the stool wet weight by at least 5%, 10%, 15%, 20%, 25%, 30%, 35%, 40%, 45%, 50%, 55%, 60%, 65%, 70%, 75%, 80%, 85%, 90%, 95%, or 100%.

In various embodiments, the constipation is associated with IBS, but the present invention, in some embodiments, can also relate to chronic functional constipation.

In various embodiments, the present invention relates to the treatment of increased visceral hypersensitivity. In various embodiments, the present invention relates to the treatment of one or more of stomachaches, pain, nausea, straining, and bloating and/or gas. The present formulations and methods also treat one or more of as hard stools, infrequent stools, difficulty or straining at stools, feeling of being unable to completely empty during a bowel movement, and the sensation of wanting to go but not being able to.

In various embodiments, the present invention relates to the treatment for diabetes (type 1 or type 2) and/or glucose intolerance. In some embodiments, the present invention relates to a method for treating patient at risk of diabetes, one or more of insulin resistance, prediabetes, impaired fasting glucose (IFG), impaired glucose tolerance (IGT), and acanthosis nigricans.

In some embodiments, methods for inducing weight loss or preventing weight gain (or treating or preventing obesity or inducing weight loss or preventing weight gain in a patient that does not substantially change caloric intake), comprising administering the present formulations are provided. Patients may have undertaken or will undertake a surgery of the digestive system; be greater than about 80-100 pounds overweight; have a BMI of greater than about 35 kg/m$^2$; or have a health problem related to obesity In some embodiments, administration of the modified-release formulation of the present invention does not confer cholesterol-lowering cardiovascular effects associated with systemic administration of statins. For example, the present formulations and methods may avoid or reduce a subject's systemic exposure to a statin. For example, the present formulations and methods may provide an average reduction of less than about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, or about 2% in serum LDL-C levels after treatment.

In some embodiments, the patient is one who does not require statins for their cardiovascular therapeutic uses. In some embodiments, the patient is one who does not require statins for their cardiovascular therapeutic uses and is methane-positive (e.g. as assessed by the methods described herein such as the methane breath test and qPCR).

By maximizing retention of the antimethanogenic statins to the intestines, the methods of the invention also minimize the side effects associated with systemic release of the statin. For example, the present method prevents and/or minimizes various adverse effects associated with statin usage including, muscle-associated adverse effects, such as myositis, myalgia, rhabdomyolysis, drug-drug-interactions, cognitive effects, increased cancer risk, increases in liver enzymes, hemorrhagic stroke, increase in blood glucose levels, sleep disorders, peripheral neuropathy, sexual dysfunction, thyroid dysfunction, renal toxicity, irritability, shortness of breath, hyperkalemia, weight gain, neurodegenerative disease, pancreatitis, liver pathology, mitochondrial syndromes, dermatologic conditions, dry mouth, cataracts, olfaction, hematalogic and bone marrow adverse effects, hypotension, gastrointestinal adverse effects, including, ulcerative colitis and gastric ulceration, fatigue and headache. In some embodiments, the methods of the invention also minimizes the following side effects associated with systemic release of a statin: muscle pain, tenderness, or weakness, lack of energy, weakness, fever, dark colored urine, jaundice, pain in the stomach, including the upper right part of the stomach, nausea, unusual bleeding or bruising, loss of appetite, flu-like symptoms, rash, hives, itching, difficulty breathing or swallowing, and swelling of the face, throat, tongue, lips, eyes, hands, feet, ankles, or lower legs, hoarseness.

Accordingly, the modified-release formulation of the present invention may be used to target subjects where systemic statin levels are undesirable. In one embodiment, the subject may be women and children who are otherwise healthy and have no need for a cardiovascular medicine (as characterized, for example, as having low or zero myocardial event risk factors as per the ATP III Guideline). In another embodiment, the subject may be a child with IBS-C who has no need for a cholesterol-lowering agent. In such embodiments, administration of the modified-release formulation of the present invention results in an average reduction of less than about 20%, about 19%, about 18%, about 17%, about 16%, about 15%, about 14%, about 13%, about 12%, about 11%, about 10%, about 9%, about 8%, about 7%, about 6%, about 5%, about 4%, about 3%, or about 2% in serum LDL-C levels after treatment.

The modified-release formulation of the present invention may also be utilized as part of a treatment regimen wherein a subject is provided with an initial anti-methanogenic therapy followed by a chronic anti-methanogenic or methane-reducing and/or eliminating maintenance therapy.

The initial anti-methanogenic therapy may employ agents other than statins such as, for example, antibiotics which eradicate the methanogens. For example nitroimidazoles such as metronidazole, metronidazole esters and/or isomers or hydrophobic imidazole derivatives or rifaximin or neomycin sufficient to eradicate, substantially reduce, or reduce the enteric methanogen colonization may be used. Such initial therapy may be for 1, 2, 3, 4, 5, 6, 7, 8, 9, 10, 14, 28, 42, 56, 60, 90, 120 or 180 days or more. Examples of antibiotics include but are not limited to aminoglycosides (e.g., amikacin, gentamicin, kanamycin, neomycin, netilmicin, streptomycin, tobramycin, paromomycin), ansamycins (e.g., geldanamycin, herbimycin), carbacephems (e.g., loracarbef), carbapenems (e.g., ertapenem, doripenem, imipenem, cilastatin, meropenem), cephalosporins (e.g., first generation: cefadroxil, cefazolin, cefalotin or cefalothin, cefalexin; second generation: cefaclor, cefamandole, cefoxitin, cefprozil, cefuroxime; third generation: cefixime, cefdinir, cefditoren, cefoperazone, cefotaxime, cefpodoxime, ceftazidime, ceftibuten, ceftizoxime, ceftriaxone; fourth generation: cefepime; fifth generation: ceftobiprole), glycopeptides (e.g., teicoplanin, vancomycin), macrolides (e.g., azithromycin, clarithromycin, dirithromycin, erythromycin, roxithromycin, troleandomycin, telithromycin, spectinomycin), monobactams (e.g., aztreonam), penicillins (e.g., amoxicillin, ampicillin, azlocillin, carbenicillin, cloxacillin, dicloxacillin, flucloxacillin, mezlocillin, meticillin, nafcillin, oxacillin, penicillin, piperacillin, ticarcillin), antibiotic polypeptides (e.g., bacitracin, colistin, polymyxin b), quinolones (e.g., ciprofloxacin, enoxacin, gatifloxacin, levofloxacin, lomefloxacin, moxifloxacin, norfloxacin, ofloxacin, trovafloxacin), rifamycins (e.g., rifampicin or rifampin, rifabutin, rifapentine, rifaximin), sulfonamides (e.g., mafenide, prontosil, sulfacetamide, sulfamethizole, sulfanilamide, sulfasalazine, sulfisoxazole, trimethoprim, trimethoprim-sulfamethoxazole (co-trimoxazole, "tmp-smx"), and tetracyclines (e.g., demeclocycline, doxycycline, minocycline, oxytetracycline, tetracycline) as well as arsphenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin combination, and tinidazole.

Following the initial therapy, a subject may be placed on maintenance therapy in order to maintain reduced methanogen and/or methane levels. In some embodiments, the maintenance therapy utilizes a modified-release formulation of the present invention. In an embodiment, the initial therapy includes an antibiotic followed by a chronic maintenance regimen of low dose statin formulations. In various embodiments, the maintenance regimen may be administered for at least 1 week, at least 2 weeks, at least 3 weeks, at least 4 weeks, at least one month, at least two months, at least three months, at least four months, at least five months, at least six months, at least seven months, at least eight months, at least nine months, at least ten months, at least eleven months, at least 1 year, at least 2 years, at least 3 years, at least 4 years, at least 5 years, at least 10 years, or indefinitely.

The modified-release formulation of the present invention may be utilized solely for chronic maintenance therapy. In various embodiments, the present invention provides a method of treating previously methane positive patients who do not have one or more of cardiovascular disease, an LDL level of 190 mg/dL or higher, Type 2 diabetes who are between 40 and 75 years of age, an estimated 10-year risk of cardiovascular disease of 7.5 percent or higher who are between 40 and 75 years of age with a modified-release formulation herein in order to maintain their methane negative status. Accordingly, in some embodiments, the modified-release formulation of the present invention finds use as a prevention measure in a high risk patient.

In various embodiments, methods of the invention are useful in treatment a human subject. In some embodiments, the human is a pediatric human. In other embodiments, the human is an adult human. In other embodiments, the human is a geriatric human. In other embodiments, the human may be referred to as a patient. In some embodiments, the human is a female. In some embodiments, the human is a male.

In certain embodiments, the human has an age in a range of from about 1 to about 18 months old, from about 18 to about 36 months old, from about 1 to about 5 years old, from about 5 to about 10 years old, from about 10 to about 15 years old, from about 15 to about 20 years old, from about 20 to about 25 years old, from about 25 to about 30 years old, from about 30 to about 35 years old, from about 35 to about 40 years old, from about 40 to about 45 years old, from about 45 to about 50 years old, from about 50 to about 55 years old, from about 55 to about 60 years old, from about 60 to about 65 years old, from about 65 to about 70 years old, from about 70 to about 75 years old, from about 75 to about 80 years old, from about 80 to about 85 years old, from about 85 to about 90 years old, from about 90 to about 95 years old or from about 95 to about 100 years old. In one embodiment, the human is a child. In one embodiment, the human is a female.

Methods to Determine Methanogen Levels/Diagnostic and Patient Selections

Intestinal methanogen and/or methane levels can be determined by breath tests that measure breath methane levels. Breath testing may be utilized to identify subjects who are "methane-positive" and who can potentially benefit from methods of the present invention. Further, breath testing can also be used to monitor the efficacy of treatment. Breath testing analysis methods and equipment are known in the art (see, for example, PCT/US14/27697, the entire contents of which are incorporated by reference herein). Examples of such equipment include, for example, the QuinTron BreathTracker gas chromatographic (GC) analyzer or the QuinTron BreathTracker device (QuinTron Instrument Company, Inc., Milwaukee, Wis.).

Further, abnormal lactulose breath test results are common in subjects with IBS and therefore the present invention provides for the use of lactulose breath tests in evaluating patients. In some embodiments, a patient is evaluated with a lactulose breath test before and/or after administration with the present formulations.

In general, individuals having a breath methane level of at least about 3 ppm are generally associated with methanogen-associated disorders and are likely to benefit from methods of the present invention. Alternatively, methods of the invention may be practiced on subjects having a breath methane level of at least 1 ppm, at least 1.5 ppm, at least 2 ppm, at least 2.5 ppm, at least 3 ppm, at least 3.5 ppm, at least 4 ppm, at least 5 ppm, at least 6 ppm, at least 7 ppm, at least 8 ppm, at least 9 ppm, at least 10 ppm.

One method for measuring methanogen levels involves calculation of a subject's breath methane area under the curve (BM-AUC). This method involves obtaining multiple breath samples averaging about 15 minutes apart for a period of about 90 minutes, or about 120 minutes, or for up to 4 hours or more at potentially less frequent intervals. The time period results are used to calculate a person's BM-AUC. For example, a subject may undergo a such as lactulose, xylose, lactose, or glucose breath test after a 12 hour fast. The breath test may comprise a baseline breath measurement after which the subject ingests about 10 g of such as lactulose, xylose, lactose, or glucose. Following lactulose ingestion, the subject is then asked to provide a breath sample about every 15 minutes for about 90 to about 120 minutes to determine methane production. BM-AUC may be utilized for more precisely determining and monitoring, for example, the efficacy of the anti-methanogenic therapy. BM-AUC measurements could also be utilized to segregate "methane positive" from "methane negative" subjects for improved clinical decision making BM-AUC may be compared to or utilized with measurement of methanogen levels in stool samples via PCR, e.g. qPCR. Alternatively, measurement of methanogen levels in stool samples via PCR, e.g. qPCR may supplant the use of a breath test. More precise techniques may also involve measurement of breath methane taking into account and subtracting ambient methane levels.

Spot breath methane analysis via commercially available equipment such as BreathTracker may be used in discriminating "methane-positive" from "methane-negative" individuals, and monitoring the success, failure, dose titration, dosing schedule (daily or non-daily, for example) of the modified-release formulations, such as various antimethanogenic statins. For example, the lowest minimum effective dose may be identified as such. Additional instruments and techniques for measuring methane levels include, but are not limited to, cavity enhanced absorption techniques such as a LGR-FMR methane measurement instrument having a range as low as 0.01 ppm (Los Gatos Research, Inc., Mountain View, Calif.), wavelength-scanned cavity down-ring spectroscopy, carbon isotope analysis (G2132-i13C, Picarro, Inc, Santa Clara, Calif.), gas chromatography, mass spectroscopy, membrane extracted carbon isotope analysis (Pollock, 2012 GSA Annual Meeting, "Membrane Extracted Carbon Isotope Analysis Of Dissolved Methane"), headspace gas chromatography with FID detector and GC combustion with IRMS instruments, for example. Other instruments having the ability to measure low concentration breath methane levels at higher precision than the clinical validated instrument marketed as the QuinTron BreathTracker include high precision breath methane analysis (HPBMA). Use of HPBMA may be used to test spot breath methane levels or in BM-AUC form.

In some embodiments, detection of hydrogen quantity and methane quantity is by gas chromatography with mass spectrometry and/or radiation detection to measure breath emissions of isotope-labeled carbon dioxide, methane, or hydrogen, after administering an isotope-labeled substrate that is metabolizable by gastrointestinal bacteria but poorly digestible by the human host, such as lactulose, xylose, mannitol, or urea (e.g., G. R. Swart and J. W. van den Berg, $^{13}$C breath test in gastrointestinal practice, *Scand. J. Gastroenterol.* [*Suppl.*] 225:13-18 [1998]; S. F. Dellert et al., The $^{13}$C-xylose breath test for the diagnosis of small bowel bacterial overgrowth in children, J. *Pediatr. Gastroenterol. Nutr.* 25(2):153-58 [1997]; C. E. King and P. P. Toskes, Breath tests in the diagnosis of small intestinal bacterial overgrowth, *Crit. Rev. Lab. Sci.* 21(3):269-81 [1984]). A poorly digestible substrate is one for which there is a relative or absolute lack of capacity in a human for absorption thereof or for enzymatic degradation or catabolism thereof.

Suitable isotopic labels include $^{13}$C or $^{14}$C. For measuring methane suitable isotopic labels can also include $^{2}$H and $^{3}$H or $^{17}$O and $^{18}$O, as long as the substrate is synthesized with the isotopic label placed in a metabolically suitable location in the structure of the substrate, i.e., a location where enzymatic biodegradation by intestinal microflora results in the isotopic label being sequestered in the gaseous product. If the isotopic label selected is a radioisotope, such as $^{14}$C, $^{3}$H, or $^{15}$O, breath samples can be analyzed by gas chromatography with suitable radiation detection means (e.g., C. S. Chang et al., Increased accuracy of the carbon-14 D-xylose breath test in detecting small-intestinal bacterial overgrowth by correction with the gastric emptying rate, *Eur. J. Nucl. Med.* 22(10):1118-22 [1995]; C. E. King and P. P. Toskes, Comparison of the 1-gram [$^{14}$C]xylose, 10-gram lactulose-$H_2$, and 80-gram glucose-$H_2$ breath tests in patients with small intestine bacterial overgrowth, *Gastroenterol.* 91(6):1447-51 [1986]; A. Schneider et al., Value of the $^{14}$C-D-xylose breath test in patients with intestinal bacterial overgrowth, *Digestion* 32(2):86-91 [1985]).

In various embodiments, treatments using the modified-release formulation of the invention result in a reduction of breath methane level of at least about 1 ppm, at least about 2 ppm, at least about 3 ppm, at least about 4 ppm, at least about 5 ppm, at least about 6 ppm, at least about 7 ppm, at least about 8 ppm, at least about 9 ppm, at least about 10 ppm, at least about 20 ppm, at least about 30 ppm, at least about 40 ppm, at least about 50 ppm, at least about 60 ppm, at least about 70 ppm, at least about 80 ppm, at least about 90 ppm, at least about 100 ppm, at least about 110 ppm, at least about 120 ppm, at least about 130 ppm, at least about 140 ppm, at least about 150 ppm, at least about 160 ppm, at least about 170 ppm, at least about 180 ppm, at least about 190 ppm, at least about 200 ppm, at least about 210 ppm, at least about 220 ppm, at least about 230 ppm, at least about 240 ppm, and at least about 250 ppm.

The samples used for the present invention include a patient's breath. In various embodiments, measurement of methanogen levels in stool samples via PCR, e.g. qPCR or other molecular biology approaches, for example, is also provided. Further, aspirates of the fluid in the GI tract may be analyzed for methanogen and/or methane levels. Also mucosal biopsies from a site in the gastrointestinal tract may be analyzed for methanogen and/or methane levels.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. Detailed protocols for quantitative PCR are provided in, for example, Innis, et al. (1990) PCR Protocols, *A Guide to Methods and Applications*, Academic Press, Inc. N.Y.). Measurement of DNA copy number at microsatellite loci using quantitative PCR analysis is described in, for example, Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR may also be used in the methods of the invention. In fluorogenic quantitative PCR, quantitation is based on amount of fluorescence signals, e.g., TaqMan and Sybr green.

Other suitable amplification methods include, but are not limited to, ligase chain reaction (LCR) (see, for example, Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

In still other embodiments of the methods provided herein, sequencing of individual nucleic molecules (or their amplification products) is performed. In one embodiment, a high throughput parallel sequencing technique that isolates single nucleic acid molecules of a population of nucleic acid molecules prior to sequencing may be used. Such strategies may use so-called "next generation sequencing systems" including, without limitation, sequencing machines and/or strategies well known in the art, such as those developed by Illumina/Solexa (the Genome Analyzer; Bennett et al. (2005) Pharmacogenomics, 6:373-20 382), by Applied Biosystems, Inc. (the SOLiD Sequencer; solid.appliedbiosystems.com), by Roche (e.g., the 454 GS FLX sequencer; Margulies et al. (2005) Nature, 437:376-380; U.S. Pat. Nos. 6,274,320; 6,258,568; 6,210,891) and others. Other sequencing strategies such as stochastic sequencing (e.g., as developed by Oxford Nanopore) may also be used, e.g., as described in International Patent Publication No. WO/2010/004273.

In still other embodiments of the methods provided herein, deep sequencing can be used to identify and quantify the methanogen or methanogen syntrophic microorganism. These techniques are known in the art.

Kits

The present invention is also directed to a kit for the treatment of a methanogen-associated disorder. The kit is an assemblage of materials or components, including at least one of the modified-release formulations described herein. The kit may further include materials and components for the quantification of methanogens. The exact nature of the components configured in the kit depends on its intended purpose. In one embodiment, the kit is configured for the purpose of treating human subjects.

Instructions for use may be included in the kit. Instructions for use typically include a tangible expression describing the technique to be employed in using the components of the kit to affect a desired outcome, such as to treat a disorder associated with methanogens. Optionally, the kit also contains other useful components, such as, diluents, buffers, pharmaceutically acceptable carriers, syringes, catheters, applicators, pipetting or measuring tools, bandaging materials or other useful paraphernalia as will be readily recognized by those of skill in the art.

The materials and components assembled in the kit can be provided to the practitioner store in any convenience and suitable ways that preserve their operability and utility. For example, the components can be provided at room, refrigerated or frozen temperatures. The components are typically contained in suitable packaging materials. In various embodiments, the packaging material is constructed by well-known methods, preferably to provide a sterile, contaminant-free environment. The packaging material may have an external label which indicates the contents and/or purpose of the kit and/or its components.

In various embodiments, a kit comprises a pill bottle containing a desiccant to maintain formulation stability.

The invention is further described by reference to the following non-limiting examples.

EXAMPLES

Example 1: Dual Pulse Formulation

A clinical study was undertaken with a human patient. The patient was administered ALTOPREV (i.e. extended release lovastatin) and the breath methane reading was about 70 ppm. When switched to MEVACOR (i.e. immediate release lovastatin), the breath methane increased to 168 ppm. Surprisingly, when administering the combination of ALTOPREV and MEVACOR, the breath methane was reduced to 0 ppm.

Without wishing to be bound by theory, an immediate release product substantially releases higher in the GI tract than an extended release product, which releases low in the GI tract. Accordingly, a polymer coated bead released from an enteric-coated capsule as described in FIGS. 1-3 and various other dual pulse formulations are made.

Example 2: Development of Dual Pulse Formulations

Figure 5:
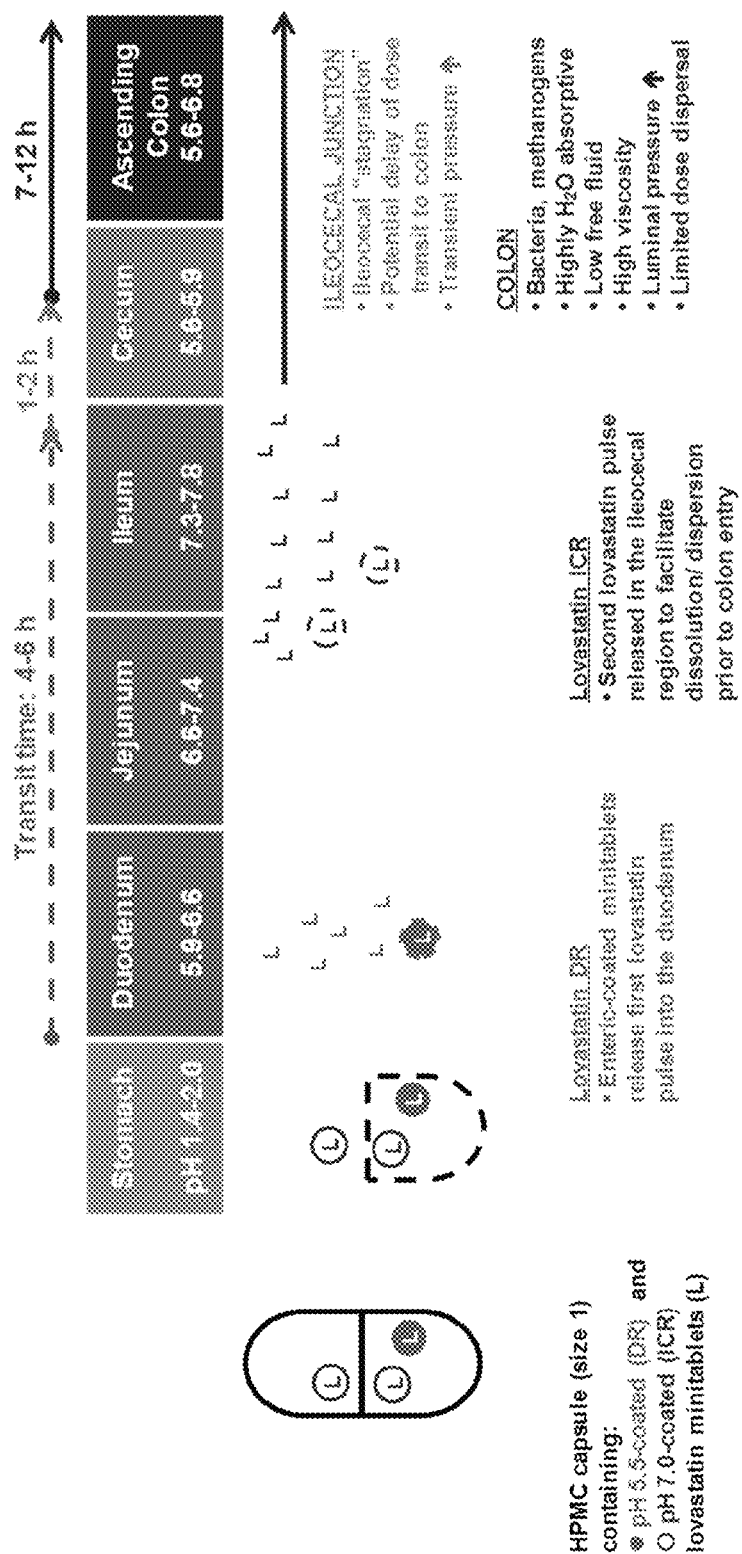
FIG. 5 depicts the release profile of lovastatin from the SYN-010 (21 mg) formulation.

A SYN-010 drug product was produced which was a HPMC capsule filled with enteric-coated mini-tablets from which lovastatin was released at different intestinal pH values. The mini-tablets were designed to pass through the stomach unchanged then release a small amount of lovastatin into the duodenum and the majority of the lovastatin dose into the ileocecal junction and colon (FIG. 5). The relative amounts of lovastatin released into the small and large intestine reflected the levels of methane-producing archaea in each location.

Each mini-tablet in the SYN-010 dosage form contains lovastatin combined with USP excipients and coated with a EUDRAGIT® enteric polymer that dissolves at either pH 5.5 (duodenal release; DR) or pH 7.0 (ileocecal release; ICR). Specifically, the SYN-010 (21 mg) formulation comprises an opaque, white, size 1 HPMC capsule containing 1×pH 5.5-coated mini-tablet (DR) and 2×pH 7.0-coated mini-tablets (ICR). The SYN-010 (42 mg) formulation comprises an opaque, white, size 1 HPMC capsule containing 1×pH 5.5-coated mini-tablet (DR) and 5×pH 7.0-coated (ICR).

The SYN-010 capsules are ingested orally, once daily, with 200 mL water. The SYN-010 capsules are swallowed whole and not chewed. The SYN-010 capsules do not require dilution.

Lovastatin was produced, analyzed and released using methodology known in the art. The properties of lovastatin is summarized below in Table 2:

TABLE 2

| Property | Description |
| --- | --- |
| Name | Lovastatin |
| CAS | 75330-75-5 |
| Formula | $C_{24}H_{36}O_5$ |
| MW | 404.54 g/mol |
| Appearance | White to off-white crystalline powder |
| Melting Point | 174.5° C. (under $N_2$); 170.6-170.8° C. (crude product) |
| Density | 1.12 g/100 cm$^3$ |
| Solubility (room temp) | Water 0.0004 mg/mL; ethanol 16 mg/mL; methanol 28 mg/mL |
| Specific Rotation | (+)328.9° |
| UV $\lambda_{max}$ | 238 nm |

Various excipients were utilized in the SYN-010 drug product and their functions are listed in Table 3 below. The excipients and coatings were chosen to enable formulation of lovastatin in appropriate enteric-coated mini-tablets and provide the desired lovastatin dual-pulse release profile detailed herein.

TABLE 3

| Name | Common Name | Function |
| --- | --- | --- |
| Lovastatin | Lovastatin lactone | Active pharmaceutical ingredient; reduces methane production by intestinal archaea |
| Avicel PH102 | Cellulose, microcrystalline | Tablet diluent |
| Kollidon VA64 Fine | Copovidone | Tablet binder |

TABLE 3-continued

| Name | Common Name | Function |
|---|---|---|
| Aerosil 200 | Silicon dioxide (silica) | Viscosity and dispersion agent |
| Magnesium stearate | Magnesium stearate | Lubricant used to facilitate tableting |
| Kollidon CL | Crospovidone | Tablet disintegrant |
| EUDRAGIT L 30 D-55 + PlasACRYL HTP20 | Enteric polymer, pH 5.5 Poly(methacrylic acid-co-ethyl acrylate) 1:1 | Enteric coating that dissolves at pH 5.5, enabling the mini-tablets to pass through the stomach unchanged and release drug into the duodenum (DR). PlasAcryl is an anti-tacking agent coating additive that results in shorter preparation and spraying times |
| EUDRAGIT FS 30 D + PlasACRYL T20 | Poly(methyl acrylate-co-methyl methacrylate-co-methacrylic acid) 7:3:1 | Enteric coating that dissolves at pH 7.0, enabling, the mini-tablets to pass through the stomach and upper small intestine unchanged and release drug into the ileocecal junction and colon (ICR). PlasAcryl is an anti-tacking agent coating additive that results in shorter preparation and spraying times |
| FD&C Blue No.2 | FD&C Blue No.2 | Pigment used to differentiate the two enteric-coated mini-tablets to facilitate encapsulation and ensure quality control |
| Vcaps | HPMC, size 1, opaque white capsule | Capsule shell |

The compatibility of lovastatin drug substance with formulation excipients was evaluated in binary stress testing studies where 1:1 mixtures of lovastatin and each excipient were stored for 7 days under different conditions of temperature and relative humidity (RH). Samples were analyzed by HPLC (based on USP methods) at day 0 and day 7. Data from binary stress testing studies with the present excipients are presented in Table 4 below:

TABLE 4

| Lovastatin 1:1 mixture with indicated excipient | Lovastatin degradant peak (% of lovastatin) after storage for 7 days at the indicated condition[a,b] | | | | |
|---|---|---|---|---|---|
| | Day 0 | 5° C. | 25° C./60% RH | 40° C./75% RH | 50° C. |
| Alone (no excipient) | 0.03 | 0.00 | 0.00 | 0.00 | 0.02 |
| Kollidon VA64 Fine | 0.04 | 0.05 | 0.04 | 0.05 | 0.04 |
| Aerosil 200 | 0.07 | 0.09 | 0.09 | 0.23 | 0.10 |
| Kollidon CL-F | 0.05 | 0.05 | 0.05 | 0.06 | 0.05 |
| Citric acid | 0.38 | 0.63 | 0.69 | 0.23 | 0.64 |
| EUDRAGIT L 30 D-55 + PlasACRYL HTP20[c] | 0.11 | 0.19 | 0.19 | 0.27 | 0.23 |
| EUDRAGIT FS 30 D + PlasACRYL T20[c] | 0.11 | 0.18 | 0.19 | 0.33 | 0.26 |

[a]HPLC relative retention time 0.46 min = lovastatin β-hydroxyacid.
[b]USP monograph requires individual impurities to be no more than 0.2%.
[c]High moisture content.

Binary stress testing identified that lovastatin lactone alone was stable over a range of conditions; however, formulated lovastatin underwent a small amount of hydrolytic degradation to the ß-hydroxyacid. This was exacerbated in the presence of acidic materials such as citric acid. Subsequent stress testing of enteric-coated lovastatin mini-tablets affirmed lovastatin moisture sensitivity and demonstrated that the small amount of lovastatin degradation observed in the dosage form may be prevented by storage in a sealed container or by storage with a desiccant (see Table 5 below). Moisture barrier sub-coats, including SEPI-FILM™ LP014 and LP030 (SEPPIC), Opadry® amb II (Colorcon), and Aquarius® MG (Ashland Aqualon Functional Ingredients) were evaluated during formulation development. The Acryl-EZE® (Colorcon) pH 5.5 enteric coating was also evaluated in initial coat integrity testing in 0.1 M HCl. The EUDRAGIT polymers were chosen for use in the SYN-010 formulations.

TABLE 5

| | Composition of coated lovastatin-containing mini-tablets (%)[a] | | | | |
|---|---|---|---|---|---|
| FORMULATION | ANH-056 | ANH-069 | ANH-073 | ANH-069 | ANH-069 |
| Lovastatin lactone | 14.0% | 12.3% | 12.9% | 12.3% | 12.3% |
| Avicel PH102 | 70.0% | 61.7% | 64.4% | 61.7% | 61.7% |
| Kollidon VA64 Fine | 7.0% | 6.2% | 6.4% | 6.2% | 6.2% |
| Aerosil 200 | 2.0% | 1.8% | 1.8% | 1.8% | 1.8% |
| Magnesium stearate | 1.0% | 0.9% | 0.9% | 0.9% | 0.9% |
| Kollidon CL-F | 6.0% | 5.3% | 5.5% | 5.3% | 5.3% |
| Aquarius MG[b] | — | 4.3% | — | 4.3% | 4.3% |
| EUDRAGIT FS 30 D + PlasACRYL T20 | — | 7.6% | 7.9% | 7.6% | 7.6% |
| TOTAL | 100.0% | 100.0% | 100/.0% | 100.0% | 100.0% |
| STRESS TESTING | Lovastatin degradant peak (% of lovastatin) after storage at 40° C./75% RH in different containers (n = 2)[c] | | | | |
| Container | Open Dish | Open Bottle[d] | Closed Bottle[d] | Closed Bottle[d] | Closed Bottle[d] |
| Desiccant | — | — | — | — | Silica gel |
| Day 0 | not tested | 0.12, 0.13 | 0.15, 0.14 | 0.12, 0.13 | 0.12, 0.13 |
| Day 7 | 0.64 | 0.46, 0.47 | 0.32, 0.34 | 0.23, 0.23 | 0.09, 0.09 |

[a]All mini-tablets contained the same core (ANH-056) prior to coating.
[b]Moisture barrier sub-coat.
[c]HPLC RRT 0.46 min = lovastatin β-hydroxyacid; USP monograph limit no more than 0.2%.
[d]High-density polyethylene (HDPE) bottle.

The compositions of the lovastatin-containing, enteric-coated mini-tablets and placebo enteric-coated mini-tablets are detailed in Table 6. The mini-tablets are round (5.5 mm diameter×2.5 mm high) with normal concavity.

TABLE 6

| | | | DR mini-tablets | | ICR mini-tablets | | Placebo | |
|---|---|---|---|---|---|---|---|---|
| Component | Common Name | Compendia | mg | % | mg | % | mg | % |
| Lovastatin | Lovastatin lactone | USP/NF | 7.0 | 12.2 | 7.0 | 12.2 | — | 0.0 |
| Avicel ® PH102 | Cellulose, microcrystalline | USP/NF | 35.0 | 60.9 | 35.0 | 60.9 | 42.0 | 73.0 |
| Kollidon ® VA64 Fine | Copovidone | USP/NF | 3.5 | 6.1 | 3.5 | 6.1 | 3.5 | 6.1 |
| Aerosil ® 200 | Silicon dioxide (silica) | USP/NF | 1.0 | 1.7 | 1.0 | 1.7 | 1.0 | 1.7 |
| Magnesium stearate | Magnesium stearate | USP/NF | 0.5 | 0.9 | 0.5 | 0.9 | 0.5 | 0.9 |
| Kollidon ® CL-F | Crospovidone | USP/NF | 3.0 | 5.2 | 3.0 | 5.2 | 3.0 | 5.2 |
| EUDRAGIT ® L 30 D-55 + PlasACRYL ™ HTP20[a] | Enteric polymer, pH 5.5 Poly(methacrylic acid-co-ethyl acrylate) 1:1 | USP/NF USP/NF | 7.5 | 13.0 | — | — | — | — |
| EUDRAGIT ® FS 30 D + PlasACRYL ™ T20 | Poly(methyl acrylate-co-methyl methacrylate-co-methacrylic acid) 7:3:1 | Non compendial | — | — | 7.5 | 13.0 | 7.5 | 13.0 |
| Coated Mini-tablet Total | | | 57.5 | 100.0 | 57.5 | 100.0 | 57.5 | 100.0 |

[a]FD&C Blue No. 2 Aluminum Lake 12-14% (0.0065% of the EUDRAGIT L30 D-55 coated mini-tablet weight) included to allow visual differentiation of the DR mini-tablets The compositions of SYN-010 21 mg and 42 mg capsule dosage forms and placebos are further detailed in Table 7 below:

TABLE 7

| | PARAMETER | | |
|---|---|---|---|
| | 21 mg | 42 mg | Placebo |
| | MINI-TABLETS per CAPSULE | | |
| | No. | No. | No. |
| DR (pH 5.5 coated) | 1 | 1 | — |
| ICR (pH 7.0 coated) | 2 | 5 | 6 |
| Total | 3 | 6 | 6 |

| | COMPONENTS per CAPSULE | | | | | |
|---|---|---|---|---|---|---|
| | mg | % | mg | % | mg | % |
| Lovastatin lactone | 21.0 | 8.5 | 42.0 | 10.0 | — | — |
| Avicel PH102 | 105.0 | 42.4 | 210.0 | 50.0 | 252.0 | 60.0 |
| Kollidon VA64 Fine | 10.5 | 4.2 | 21.0 | 5.0 | 21.0 | 5.0 |
| Aerosil 200 | 3.0 | 1.2 | 6.0 | 1.4 | 6.0 | 1.4 |
| Magnesium stearate | 1.5 | 0.6 | 3.0 | 0.7 | 3.0 | 0.7 |
| Kollidon CL-F | 9.0 | 3.6 | 18.0 | 4.3 | 18.0 | 4.3 |
| EUDRAGIT L 30 D-55 + PlasACRYL HTP20[a] | 7.5 | 3.0 | 7.5 | 1.8 | — | — |
| EUDRAGIT FS 30 D + PlasACRYL T20 | 15.0 | 6.1 | 37.5 | 8.9 | 45.0 | 10.7 |
| Vcaps ® HPMC capsule; white, opaque size 1[a] | 75.0 | 30.3 | 75.0 | 17.9 | 75.0 | 17.9 |
| SYN-010 Total | 247.5 | 100.0 | 420.0 | 100.0 | 420.0 | 100.0 |

[a]FD&C Blue No. 2 Aluminum Lake 12-14% (0.0065% of the EUDRAGIT L30 D-55 coated mini-tablet weight) included to allow visual differentiation of the DR mini-tablets The SYN-010 formulation takes advantage of (i) intestinal regional differences in lovastatin hydrolysis and absorption, and (ii) intrinsic absorption differences between lovastatin lactone and ß-hydroxyacid to increase the amount of lovastatin lactone in the intestinal lumen and minimize the reabsorption of lovastatin species into the systemic circulation. Specifically enteric protection avoids gastric absorption and prevents conversion of the more poorly absorbed lovastatin lactone (the active antimethanogenic agent) to the more readily absorbed ß-hydroxyacid (not antimethanogenic). In addition, the bulk of lovastatin released from SYN-010, 21 mg and 42 mg occurs after the primary absorption lovastatin windows in the small intestine, thereby increasing delivery of lovastatin lactone to the colon.

Figure 6:
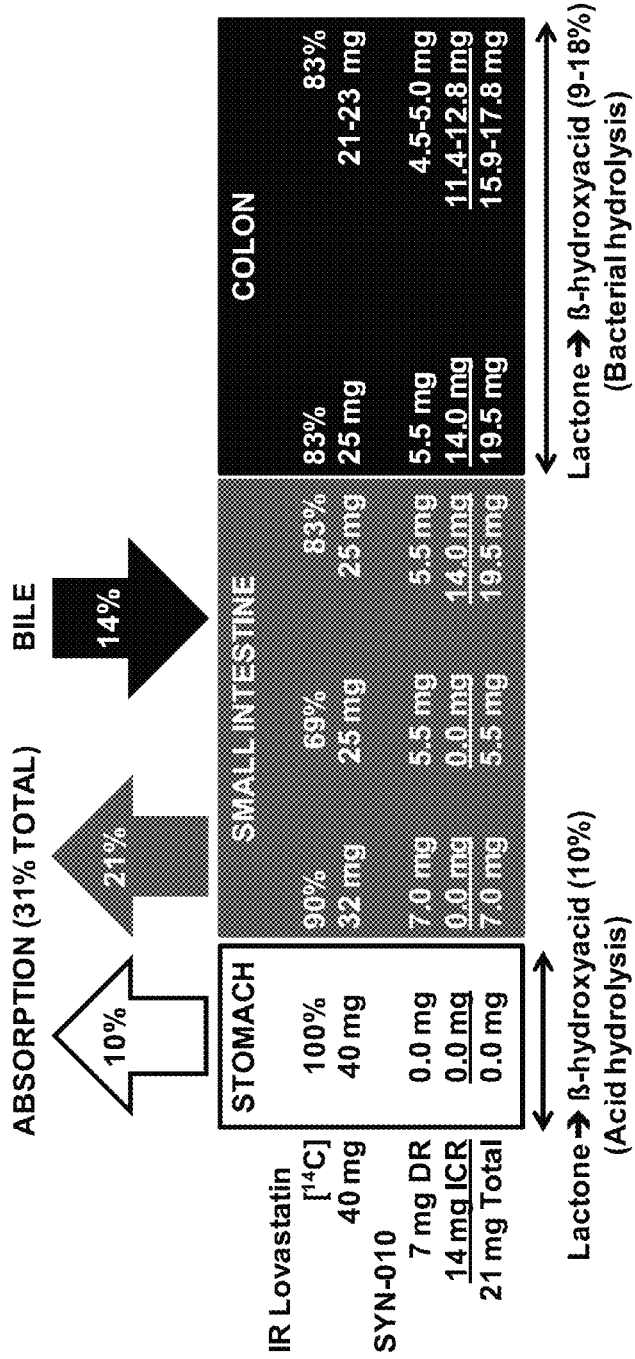
FIG. 6 shows the estimated lovastatin lactone levels in the gastrointestinal tract after oral administration.

The primary absorption window for both lovastatin lactone and ß-hydroxyacid is the small intestine; however, there appears to be a meaningful gastric component to lovastatin oral absorption. For example, ~30% of an intragastric dose of either lovastatin lactone or ß-hydroxyacid exited the gastric juice of pylorus-ligated rats within 30 min. There appears to be relatively little pre-portal hydrolysis of lovastatin lactone in vivo after oral administration (~10%), with the bulk of the lactone to ß-hydroxyacid conversion occurring in the liver and the plasma. Studies also suggest that colonic bacteria may contribute to intestinal lovastatin hydrolysis, and incubation of lovastatin lactone with human and rat fecal bacterial enzyme fractions resulted in 8-19% loss of lovastatin lactone over a 12 h period. FIG. 6 shows the estimated lovastatin lactone levels in the gastrointestinal tract after oral dosing.

Figure 7:
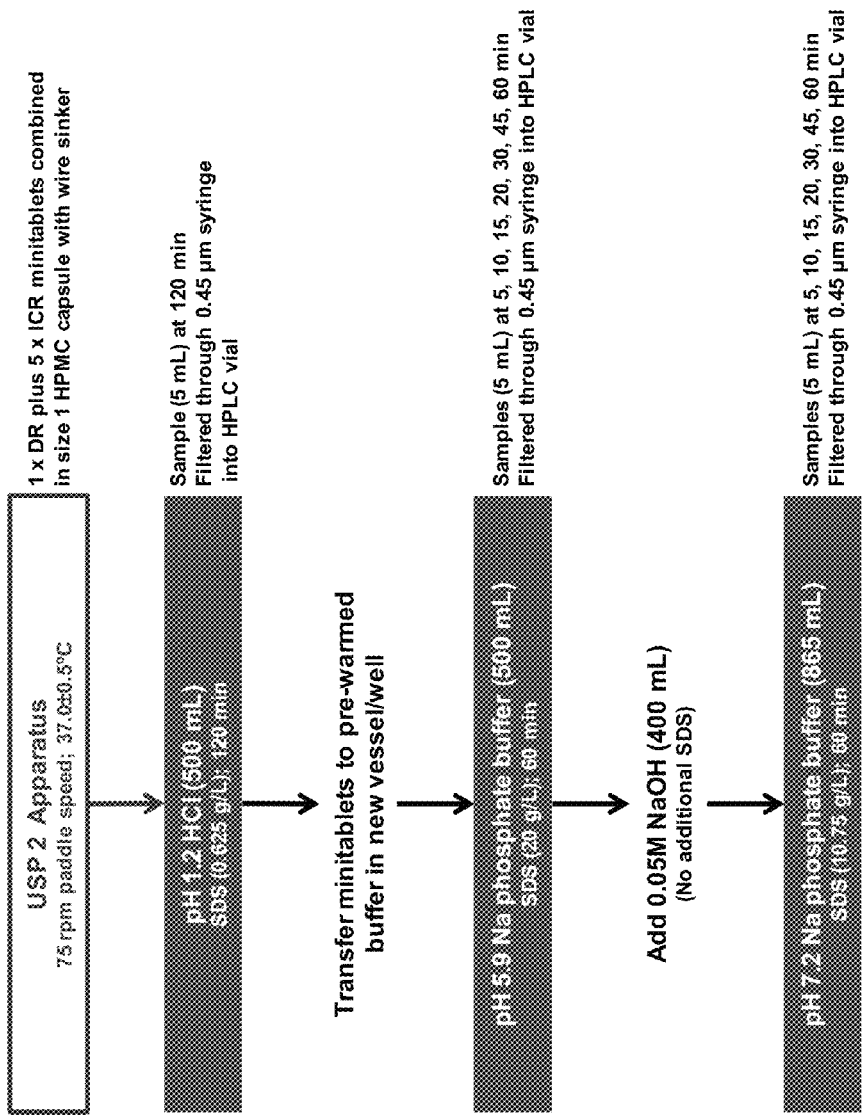
FIG. 7 depicts the dissolution methodology utilized to evaluate lovastatin release from enteric-coated mini-tablets at different pH values.

Lovastatin is a white to off-white crystalline powder that was co-milled and blended with excipients during processing but was not otherwise processed to reduce particle size or convert to an amorphous state. In the present indication (IBS-C), systemic lovastatin bioavailability may not be required and solubility may not a primary determinant of potential efficacy. Rather, lovastatin needs to disperse in the intestinal lumen, and dissolution studies have demonstrated appropriate lovastatin release from the SYN-010 dosage form Development of a product with the appropriate lovastatin release profile required detailed dissolution testing in media of varying pH values that represented different regions of the intestinal tract. The dissolution strategy employed during SYN-010 development is represented in FIG. 7. Dissolution studies utilized a Type 2 apparatus (as proscribed in the lovastatin USP monograph; Lovastatin USP 37) and evaluated a number of variables, including paddle speed and the concentration of sodium dodecyl sulfate (SDS) included in the dissolution medium. During development, it was determined that an elevated paddle speed (100 rpm) was unsuitable for the integrity of the enteric coating while a lower paddle speed (50 rpm) did not provide sufficient agitation of the dosage forms to ensure lovastatin dissolution. The SDS concentrations in the dissolution medium at pH 5.9 (20 g/L) and pH 7.0 (10.75 g/L) were sufficient to enable appropriate dissolution of lovastatin; however SDS concentrations of 5-20 g/L in the acid medium (0.1 M HCl) adversely impacted the pH 5.5 enteric coating. This issue was resolved by application of a thicker coating of enteric polymer (15% weight increase over the mini-tablet core) that was used in the SYN-010 clinical formulation. A lower concentration of SDS (0.625 g/L) was employed in the 0.1 M HCl dissolution medium without adversely impacting lovastatin dissolution.

Figure 8:
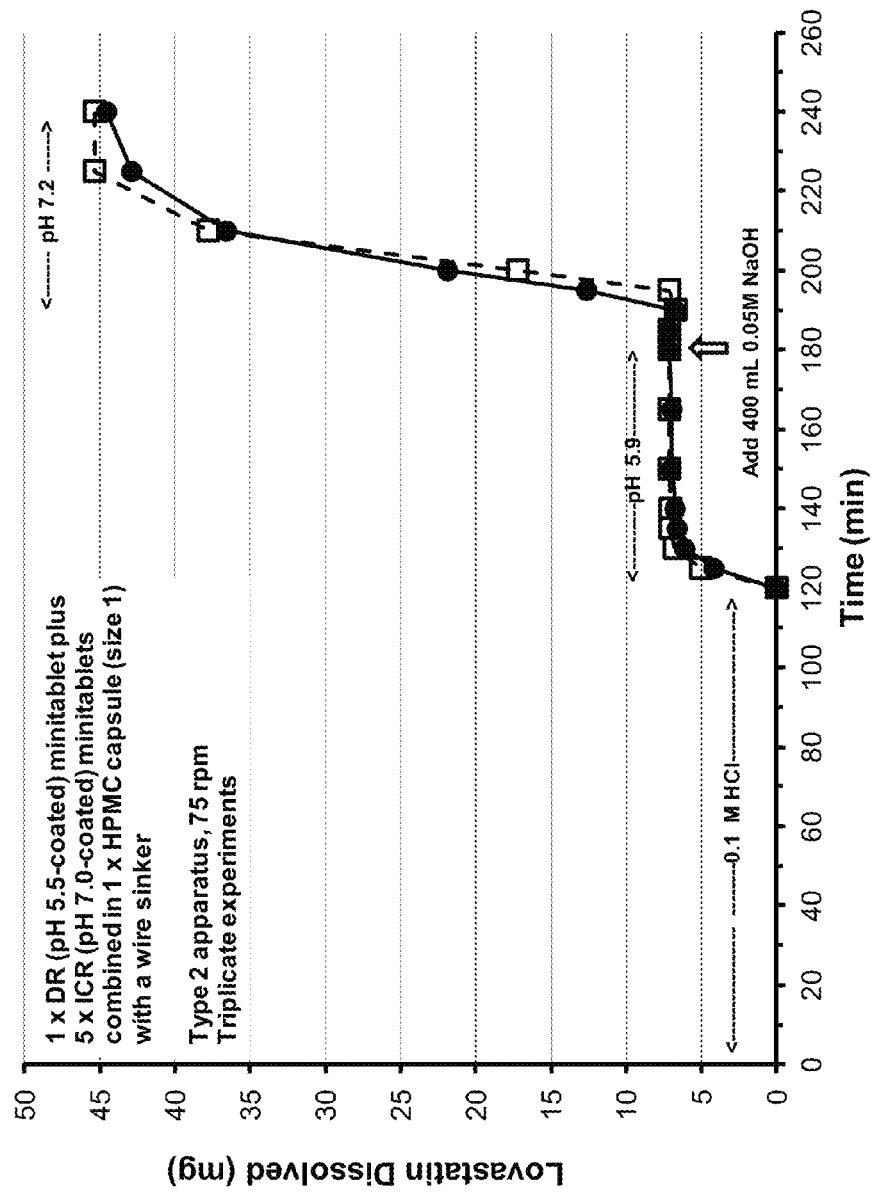
FIG. 8 depicts the dissolution profile of the SYN-010 (42 mg) capsule in a Type 2 apparatus at different pH values.

Data from the dissolution studies of SYN-010, 42 mg capsules are presented in FIG. 8. Each mini-tablet contained the ANH-056 core. The 1×DR mini-tablet was coated with EUDRAGIT L 30 D-55+PlasACRYL HTP20 (15.55% weight increase over the mini-tablet core). The 5×ICR mini-tablets was coated with EUDRAGIT FS 30 D+PlasACRYL T20 (15.87% weight increase). The HPMC capsule shell dissolved within 10 minutes in 0.1 M HCl (representing the stomach) to expose the lovastatin mini-tablets. All mini-tablets were stable in 0.1 M HCl for 2 hours, and no lovastatin or lovastatin degradation products were observed in the acid medium. After 2 hours in 0.1 M HCl, the mini-tablets were transferred to a new well containing pH 5.9 phosphate buffer (representing the duodenum) and the 1×DR mini-tablet disintegrated and lovastatin dissolved completely within 10 minutes. After 60 minutes at pH 5.9, the pH was raised to pH 7.2 (representing the ileum) by addition of NaOH, After a 30 min lag period, complete disintegration of the 5×ICR tablets and dissolution of lovastatin was observed at pH 7.2.

The dissolution studies on SYN-010, 42 mg capsules demonstrate that a dosage form comprising HPMC capsules containing a combination of enteric-coated lovastatin mini-tablets has the appropriate release profile to deliver lovastatin to the duodenum and the ileocecal junction/colon.

Dissolution studies have also determined that the thickness of the mini-tablet enteric coating—particularly the EUDRAGIT L 30 D-55—was important for ensuring mini-tablet integrity in stomach acid and thus the appropriate lovastatin release profile. As illustrated in Table 8, when combinations of mini-tablets with different coating thicknesses were stirred in 0.1 M HCl, EUDRAGIT L 30 D-55 coating thicknesses of less than 15% failed. Specifically, Table 8 shows the effect of different enteric coating thicknesses and on coat integrity of mini-tablets stirred in 0.1 M HCl (pH 1.2) for 120 min in a USP type 2 dissolution apparatus at 75 rpm. SDS added to the dissolution medium to help solubilize lovastatin also adversely impacted the pH 5.5 enteric coating, and reduced levels of SDS were used in dissolution studies of the final SYN-010, 21 mg and 42 mg clinical dosage forms.

TABLE 8

| Coating pH | Thickness wt. gain | Tablet integrity over 120 min period at indicated SDS conc. (g/L)[a] (B = blister, R = rupture, S = swell.) | | | | | |
|---|---|---|---|---|---|---|---|
| | | 0 | 0.625 | 1.25 | 2.5 | 5 | 20 |
| 5.5[b] | 9.56% | B, S, R | — | — | — | B, S, R | B, R |
| 7.0[c] | 9.03% | No change | — | — | — | No change | No change |
| 7.0[c] | 11.4% | S[d] | — | — | — | S[e] | — |
| 5.5[b] | 15.55% | No change | No change | B, S, R | B, S, R | B, S, R | — |
| 7.0[c] | 15.89% | No change | No change | No change | No change | No change | — |

[a]Identical ANH-056 tablet cores
[b]EUDRAGIT® L 30 D-55 + PlasACRYL™ HTP20.
[c]EUDRAGIT® FS 30 D + PlasACRYL™ T20.
[d]One of 6 tablets.
[e]4 of 6 tablets.

Stress-testing of enteric-coated lovastatin mini-tablets has illustrated that SYN-010, 21 mg and 42 mg can be effectively stored in closed HDPE containers containing a desiccant. SYN-010 (21 mg) and SYN-010 (42 mg) clinical trial materials were packaged in separate 60 mL high-density polyethylene (HDPE) wide-mouth round bottles with a 33 mm polypropylene child-resistant closure and an induction foil inner seal. Each bottle contained 33 SYN-010 capsules with a CAN SORB-IT® desiccant canister containing 1.0 g of silica gel desiccant. The capsules are stored at 20-25° C.

Example 3: Clinical Evaluation of Different Release Profiles

Duodenal and ileocecal release profiles are compared separately and in combination to evaluate any benefit of one over the other or synergy in the combination. Further an evaluation of the pharmacokinetics and breath methane effects of different doses and dosing profiles in methane positive subjects may be undertaken.

Example 3: Clinical Selection of Responder Patients

In this study, a retrospective chart review from the last 18 months of clinical practice was undertaken for the use of statins in treating patients with methane-positive bacterial overgrowth and the constipation-predominant form of IBS (C-IBS). While constipation and bloating severity were in general proportional to the reduction in methane, this was not a prospective study, and symptoms were subjective. The chart review therefore focused on the reduction of methane production. As data for methane were not normally distributed, data were represented as medians and a non-parametric test Mann-Whitney test was used to compare groups. Most of the methane positive IBS patients with constipation evaluated were first treated with a course of rifaximin and neomycin. Subjects placed on statin therapy were those that were resistant or refractory to this conventional antibiotic approach. This could also imply, without wishing to be bound by theory, that they are more refractory to treatment in general.

Generally, the majority of the best responses were seen in patients receiving ALTOPREV alone or in combination with immediate-release lovastatin (e.g. MEVACOR).

Figure 9A:
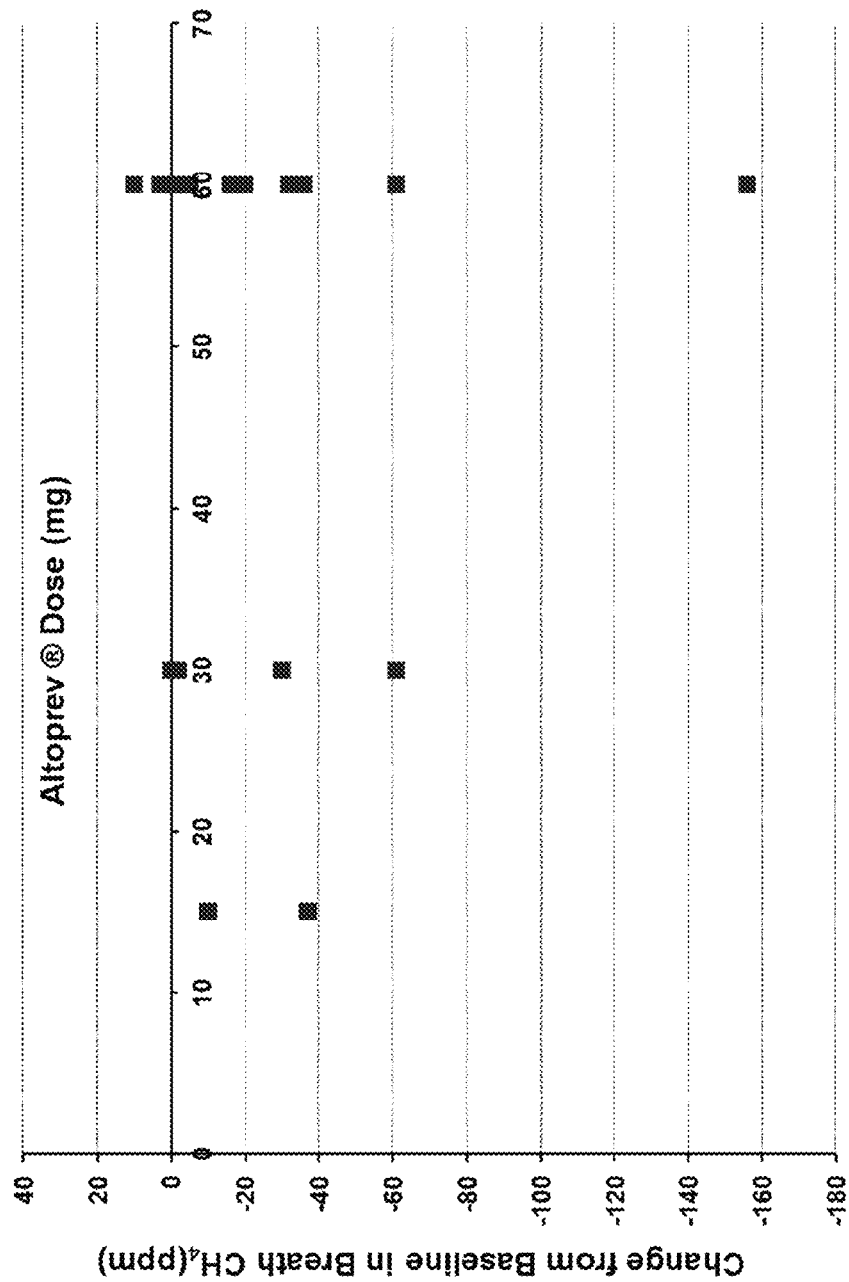
FIGS. 9A-9D show the results of a clinical chart review.
Figure 9B:
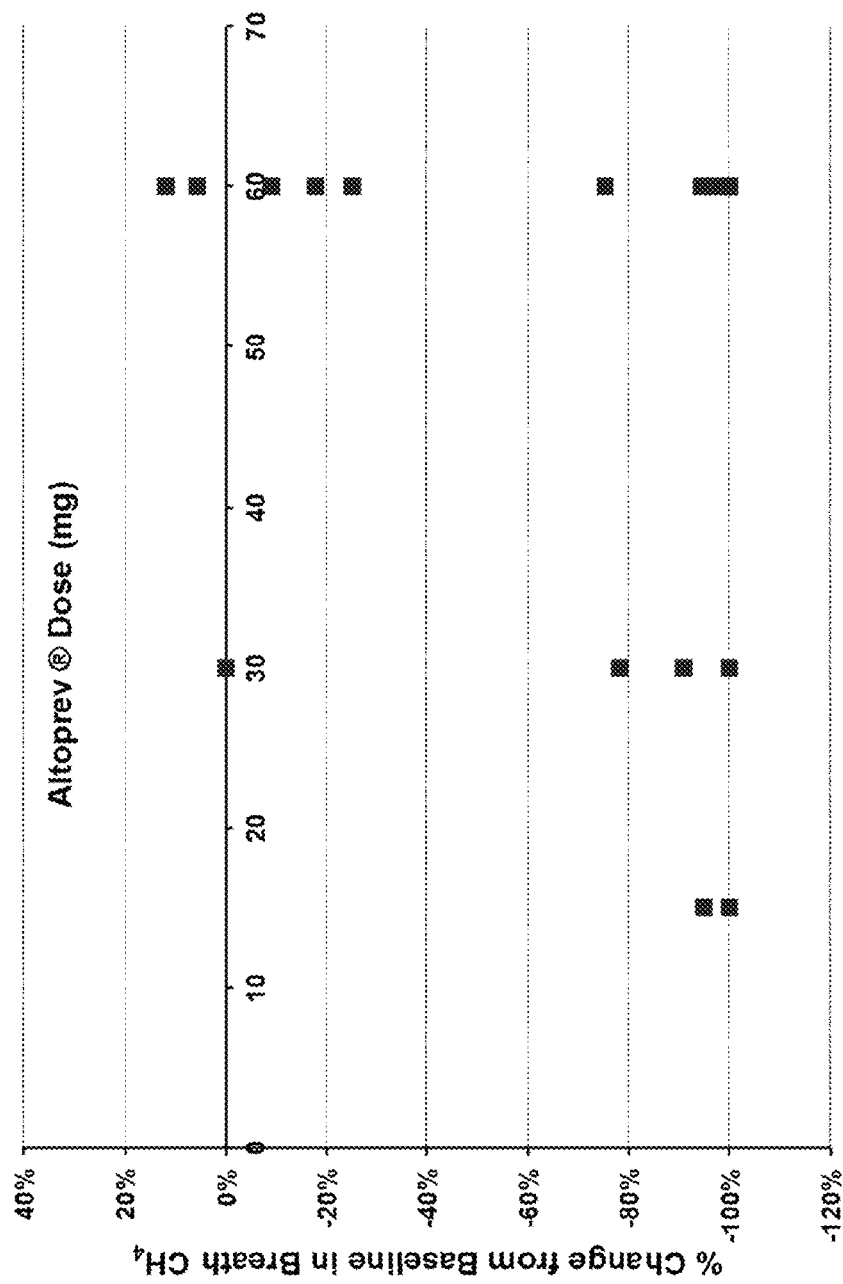

Further, evaluation of the absolute change in breath methane levels from baseline showed a trend towards a greater breath methane-lowering effect at higher ALTOPREV doses; however, there were a number of apparent non-responders (FIG. 9A). This is perhaps seen more clearly when comparing percentage change from baseline, where there was a division between ALTOPREV responders and apparent non-responders with no obvious dose response amongst the responders (FIG. 9B)

Figure 9C:
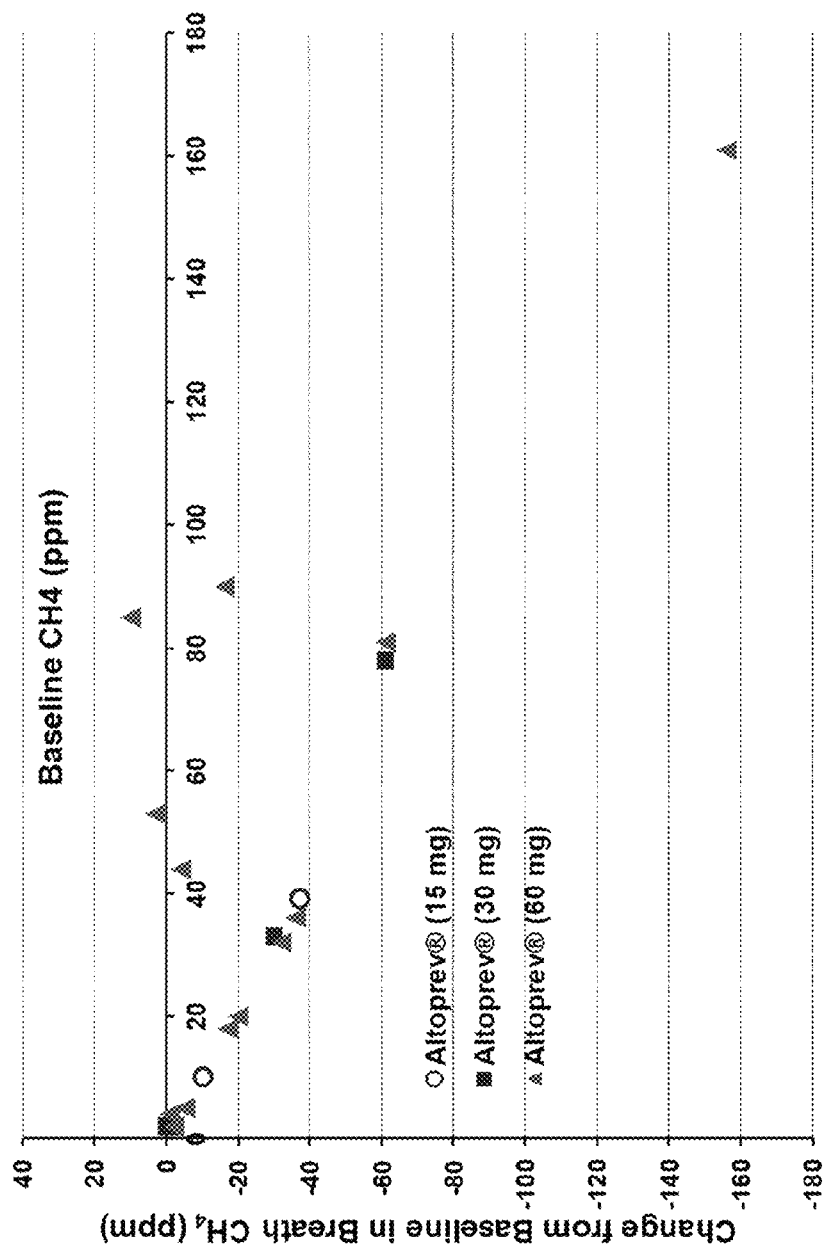
Figure 9D:
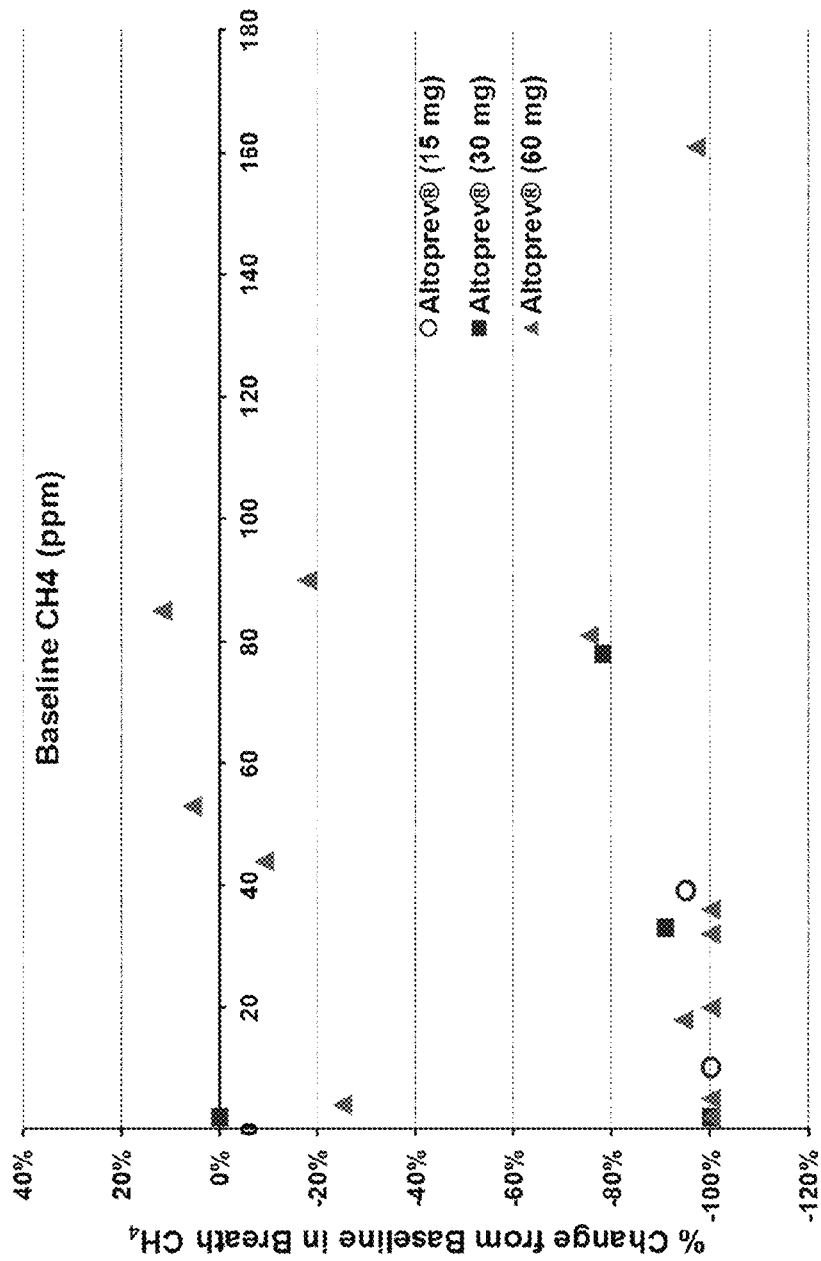

When reviewing the absolute change in breath methane levels, there appears to be an almost linear trend, with the patients having highest baseline breath methane levels showing the greatest absolute reductions in breath methane regardless of the ALTOPREV dose (FIG. 9C). In this analysis, there was a group of apparent non-responders with varying baseline methane levels. Comparison of the percentage change in breath methane vs. baseline breath methane (FIG. 9D) showed a separation between ALTOPREV responders and apparent non-responders, again, with no obvious dose response amongst the responders.

Example 4: In Vivo Effects of Lovastatin on *M. smithii* Colonized Rats with Constipation 30 adult, male Sprague-Dawley rats were placed on a high-fat diet (60.3% kcal from fat, Teklad high-fat diet TD.06414, Harlan Laboratories Inc, Madison, Wis.) for 7 weeks. The rats were assessed for increased *M. smithii* by qPCR before and after the diet, and then divided into 3 groups. Group 1 was given lovastatin in its lactone form, Group 2 was given lovastatin hydroxy acid (each 1.5 mg/rat), and Group 3 was gavaged with a placebo. Each group was gavaged daily for 10 days. Three day stool collections were performed to assess average stool wet weight and daily variability prior to commencing the high fat diet, after 7 weeks of high-fat diet, and the final days of the lovastatin gavage (still on high-fat diet). On day 10 of the gavage, rats were euthanized and DNA was extracted from contents of ligated bowel segments (duodenum, jejunum, ileum, cecum and left colon). qPCR was performed using primers for total luminal bacteria and *M. smithii*.

Figure 10A:
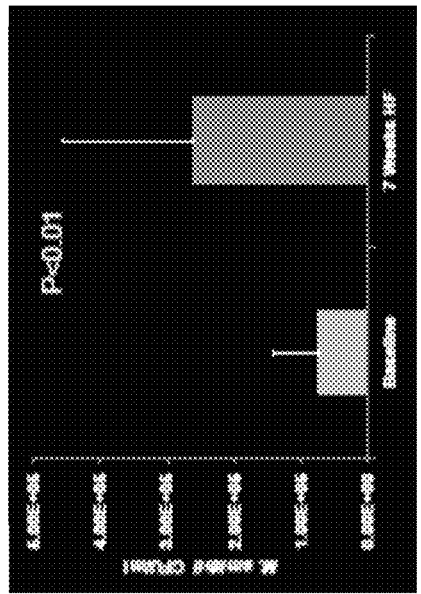
FIG. 10A shows that 7 weeks of high fat diet augmented stool *M. smithii* colonization in rats.
Figure 10B:
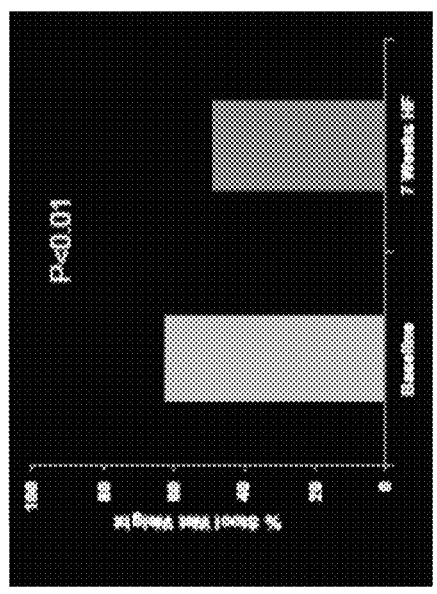
FIG. 10B shows that the high fat diet also reduced stool wet weight in the rats.
Figure 11:
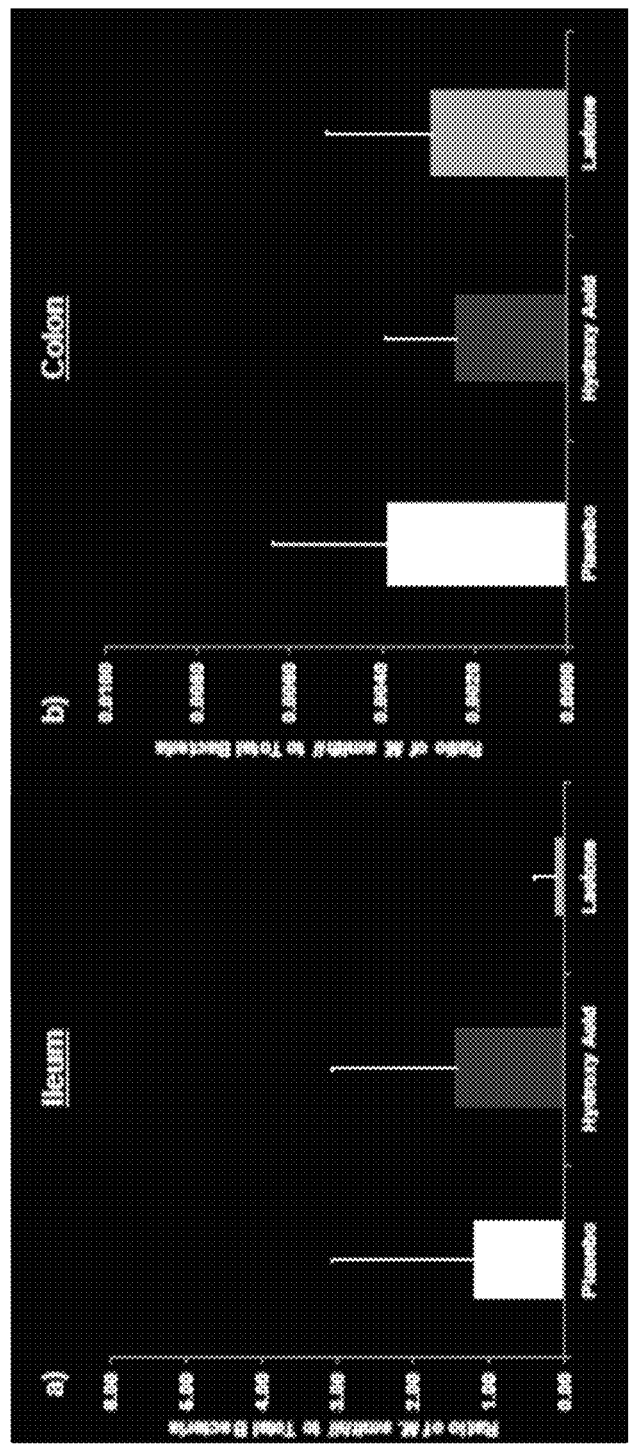
FIG. 11 shows that after lovastatin administration, ileal ratio of *M. smithii* to total bacteria was reduced.

Results indicate that high-fat diet augmented stool *M. smithii* colonization in Sprague-Dawley rats ($7.58 \times 10^4 \pm 6.62 \times 10^4$ cfu/mL at baseline to $2.60 \times 10^5 \pm 1.95 \times 10^5$ after 7 weeks of high-fat) ($P<0.01$) (FIG. 10A). This was coupled with a reduction in the stool wet-weights (62.4% at baseline to 48.6% after 7 weeks) (P<0.01) (FIG. 10B). At this point rats were divided into 3 groups. With respect to the total bacteria by qPCR, levels were not different between placebo and either lovastatin group. For *M. smithii*, the ratio of *M. smithii* to total bacteria was reduced in the ileum of rats given the lovastatin lactone but not hydroxy acid. *M. smithii* levels in the colon were unaffected (FIG. 11).

Example 5: Pharmacokinetics of SYN-010 in Dogs

The SYN-010 formulation comprises capsules containing a combination of different enteric-coated mini-tablets designed to pass through the stomach unchanged and release lovastatin in different areas of the intestinal tract. The present study evaluated the plasma pharmacokinetics of lovastatin lactone and ß-hydroxyacid after administration of the different SYN-010 lovastatin enteric-coated mini-tablets—alone and in combination—to beagle dogs, Animals were also administered commercially available immediate release and extended release formulations of lovastatin. Dogs have previously been shown to be appropriate for studying lovastatin disposition and have a gastrointestinal tract with many similarities to humans. Five dogs (6.4-8.0 kg body weight) were randomized to receive each of the following doses using a Latin square dose design, i.e., each dog received each dose during the study, separated by a one week washout period: Dose A 6×pH 5.5-coated lovastatin (7 mg) mini-tablets (duodenal release; DR); total dose 42 mg; Dose B: 6×pH 7.0-coated lovastatin (7 mg) mini-tablets (ileocecal release; ICR); total dose 42 mg; Dose C: 1×DR+5×ICR lovastatin (7 mg) mini-tablets; total dose 42 mg; Dose D: 1×MEVACOR immediate release lovastatin tablet; total dose 40 mg; Dose E: 1×ALTOPREV extended release lovastatin tablet; total dose 40 mg.

All doses were administered in a single Torpac size 000 gelatin capsule. Dogs were fasted overnight prior to dosing and food was restored 2.0-2.5 h post-dose. Blood samples were taken from each dog over a 36 h time-period and plasma was analyzed for lovastatin lactone and lovastatin ß-hydroxyacid using a qualified LC-MS/MS method. Pharmacokinetic parameters were calculated using non-compartmental methods.

Figure 12A:
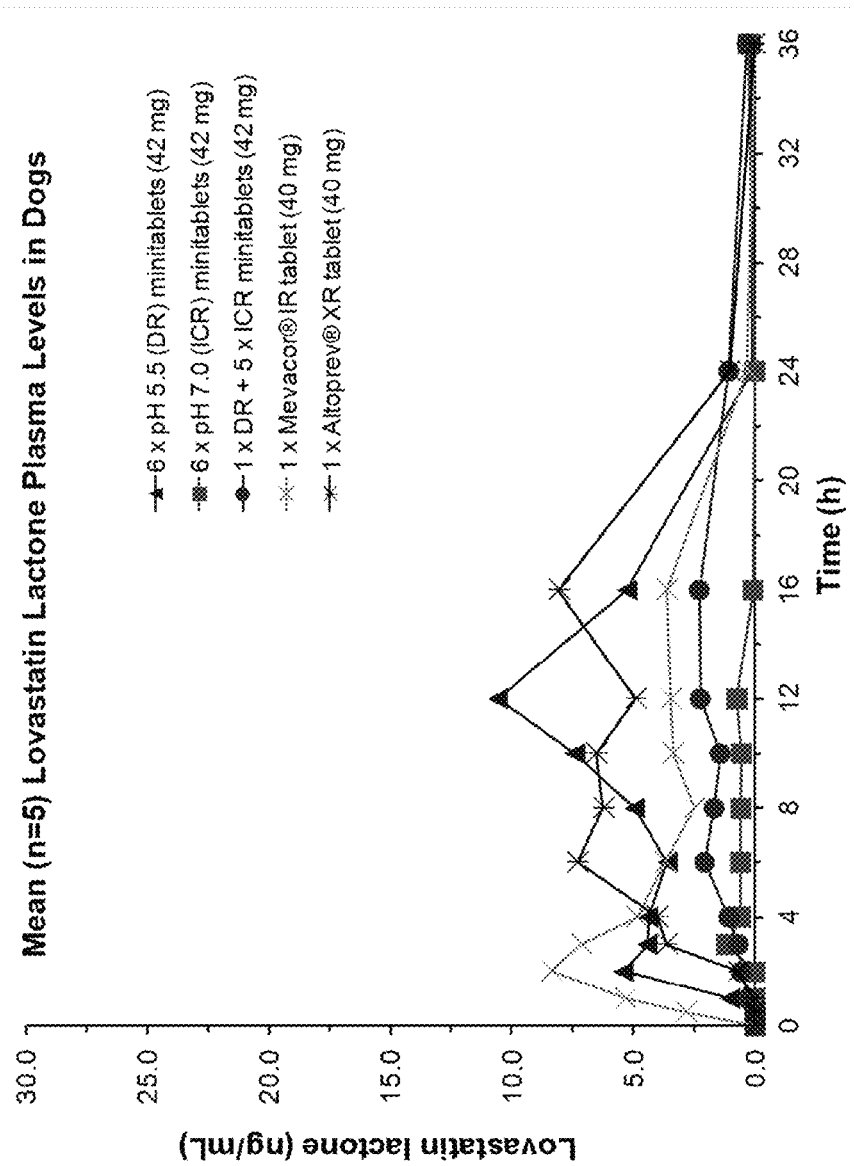
FIGS. 12A-12B show mean (n=5) plasma concentration time profiles for lovastatin lactone and lovastatin ß-hydroxy-acid, respectively, after oral administration of different lovastatin formulations to beagle dogs.
Figure 12B:
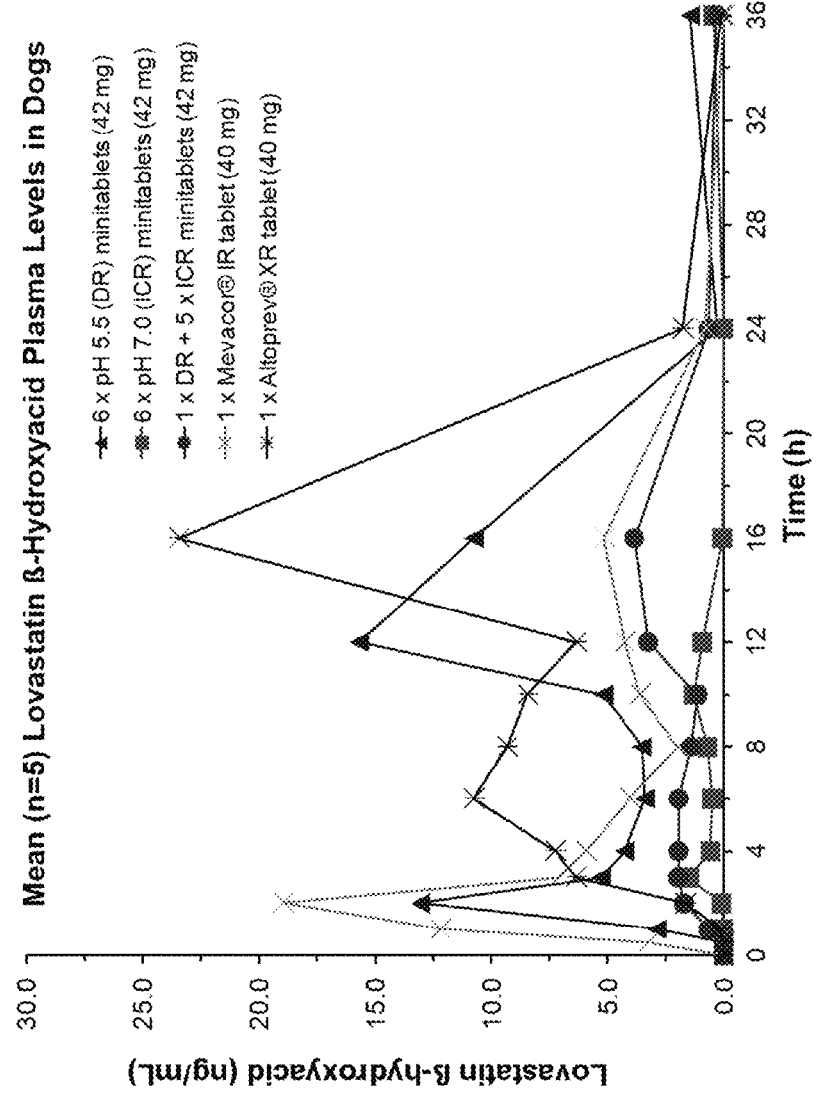

Mean concentration versus time profiles for the different doses are presented in FIG. 12. Plasma levels of lovastatin ß-hydroxyacid tracked almost identically with lovastatin lactone, consistent with published reports that conversion of lactone to ß-hydroxyacid occurs predominantly after absorption from the GI tract. The AUCacid/AUClactone ratio (1.5-1.7) was not different for Doses A, C, D and E; but was only 0.8 for Dose B, due to very low lovastatin absorption from the Dose B formulation.

The comparative pharmacokinetic behaviors of MEVACOR and ALTOPREV in this dog study were consistent with published clinical studies and pharmacokinetic parameters for these formulations were similar to those reported in published dog studies. A key difference in the current work was the presence of a large second peak concentration ($C_{peak,2}$) of both lactone and ß-hydroxyacid in some dogs, which has not previously been reported.

The DR mini-tablets (Dose A) provided similar overall lovastatin exposure (AUC) to the MEVACOR and ALTOPREV formulations; however, unlike MEVACOR, the pharmacokinetic profile for Dose A indicated that the pH 5.5 enteric coating delayed lovastatin release until the mini-tablets reached the upper small intestine. This was reflected in longer times before the first measurable lovastatin lactone and ß-hydroxyacid concentrations ($T_{lag}$ 1.0-2.0 h) and a later first peak plasma concentration ($T_{peak,1}$ 2.0-6.0 h) for Dose A compared to the MEVACOR immediate release formulation ($T_{lag}$ 0.5-1.0 h and $T_{peak,1}$ 1.0-2.0 h). As observed for MEVACOR, Dose A also demonstrated a large mean $C_{peak,2}$ that was predominantly due to two dogs. This second peak may reflect delayed release of one or more mini-tablets from the stomach of these animals. Published reports have identified that the dog pylorus is more restrictive than the human pylorus, and particles ≥5 mm in diameter (such as the SYN-010 mini-tablets) tend to be retained in the stomach until expelled with the next GI housekeeper wave (Phase III of the migrating motor complex), regardless of prandial state. The time between housekeeper waves in fed dogs (5-13 h) is highly variable and significantly longer than observed in fed humans (2-5 h). In the present study, food was restored to dogs 2.0-2.5 h post-dose. If SYN-010 mini-tablets were administered to fasted dogs immediately after a housekeeping wave, and one or more mini-tablets did not exit the stomach, these mini-tablets could be retained in the stomach for a significant period of time prior to release with the next housekeeper wave.

The results obtained with the ICR mini-tablets (Dose B) and the 1×DR+5×ICR combination (Dose C) were compelling with respect to the potential utility of these formulations in IBS-C. The very low to undetectable levels of lovastatin lactone and ß-hydroxyacid after administration of Dose B suggest negligible lovastatin absorption from the GI tract and retention of lovastatin lactone in the intestinal lumen. No undisintegrated mini-tablets or tablet fragments were reported in dog feces during routine cage-side observations. Dose C delivered low systemic lovastatin levels (i.e. the mean dose-normalized lovastatin lactone AUC was 56% of the mean dose-normalized MEVACOR AUC) and exhibited a dual pulse release profile, with two peak concentrations for each analyte separated by ~14 h. As for Dose A, the second peak was largely due to two dogs that had very large $C_{peak,2}$. Considering the negligible plasma levels of lovastatin lactone and ß-hydroxyacid observed with the ICR component alone (Dose B), the plasma concentration vs. time profiles for these analytes in Dose C appears to be predominantly due to the DR component of the formulation.

SYN-010 mini-tablets were among the drug products used in this study. Each enteric-coated mini-tablet contains 7 mg of lovastatin combined with USP excipients and coated with a EUDRAGIT® enteric polymer that dissolves at either pH 5.5 (DR) or pH 7.0 (ICR). Each mini-tablet is circular in shape, with diameter ~5 mm, height ~3 mm, and weight ~54 mg. DR mini-tablets have a pale blue color while ICR mini-tablets are white. MEVACOR 40 mg IR lovastatin tablets; ALTOPREV 40 mg XR lovastatin tablets and veterinary size 000 porcine gelatin capsules (Torpac, Fairfield N.J.) were also used. All materials were ready to use and maintained at room temperature; ALTOPREV and MEVACOR were stored desiccated in the dark.

Example 6: Phase 2 Clinical Trial of SYN-010 for IBS-C

A Phase 2, randomized, double-blind, parallel-group, placebo-controlled, multi-dose study is being conducted. The primary objective of this study is to evaluate the change from baseline in breath methane, as determined by a lactulose breath test, in methane-positive patients with IBS-C after seven days of treatment with one of two formulations of SYN-010 compared with placebo. Approximately 60 patients are being enrolled and randomly assigned in a 1:1:1 ratio to one of three groups, including two different SYN-010 dose groups, 21 mg and 42 mg, and a placebo group. Patients are scheduled to receive single oral doses of SYN-010 each day for 28 days. Sixty subjects with who are between the ages of 18 and 65, inclusive, are being enrolled.

Inclusion criteria are: subjects must have IBS-C and have a positive breath methane test result (>10 ppm) at screening, subject must meet the modified Rome III criteria for IBS-C, subject must have an average abdominal pain intensity score of ≥3 (scale 0-10) reported at screening and baseline, subject must have an average of fewer than 3 complete spontaneous bowel movement (CSBMs) per week and subject must agree to refrain from making any lifestyle changes that may affect IBS-C symptoms from the time of screening to the end of the study.

Exclusion Criteria are: subject has taken IBS treatments (prescription or over-the-counter), proton pump inhibitors, laxatives, antibiotics, subject currently has any structural abnormality of the gastrointestinal (GI) tract or a disease or condition that can affect GI motility, or any unexplained and clinically significant symptoms such as lower GI bleeding, rectal bleeding, heme-positive stool, iron-deficiency anemia, weight loss, or systemic signs of infection, subject has been diagnosed with or has a family history of familial adenomatous polyposis, hereditary nonpolyposis colorectal cancer, or any other form of familial colorectal cancer, and subject reports loose (mushy) or watery stools (Bristol Stool Form Scale [BSFS] score of 6 or 7).

A decrease from baseline in breath methane, as determined by a lactulose breath test, in methane-positive patients with IBS-C is expected.

Definitions

As used herein, "a," "an," or "the" can mean one or more than one.

Further, the term "about" when used in connection with a referenced numeric indication means the referenced numeric indication plus or minus up to 10% of that referenced numeric indication. For example, the language "about 50%" covers the range of 45% to 55%.

An "effective amount," when used in connection with medical uses is an amount that is effective for providing a measurable treatment, prevention, or reduction in the rate of pathogenesis of a disorder of interest.

As used herein, something is "decreased" if a read-out of activity and/or effect is reduced by a significant amount, such as by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100%, in the presence of an agent or stimulus relative to the absence of such modulation. As will be understood by one of ordinary skill in the art, in some embodiments, activity is decreased and some downstream read-outs will decrease but others can increase.

Conversely, activity is "increased" if a read-out of activity and/or effect is increased by a significant amount, for example by at least about 10%, at least about 20%, at least about 30%, at least about 40%, at least about 50%, at least about 60%, at least about 70%, at least about 80%, at least about 90%, at least about 95%, at least about 97%, at least about 98%, or more, up to and including at least about 100% or more, at least about 2-fold, at least about 3-fold, at least about 4-fold, at least about 5-fold, at least about 6-fold, at least about 7-fold, at least about 8-fold, at least about 9-fold, at least about 10-fold, at least about 50-fold, at least about 100-fold, in the presence of an agent or stimulus, relative to the absence of such agent or stimulus.

As referred to herein, all compositional percentages are by weight of the total composition, unless otherwise specified. As used herein, the word "include," and its variants, is intended to be non-limiting, such that recitation of items in a list is not to the exclusion of other like items that may also be useful in the compositions and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of terms such as including, containing, or having, is used herein to describe and claim the invention, the present invention, or embodiments thereof, may alternatively be described using alternative terms such as "consisting of" or "consisting essentially of."

As used herein, the words "preferred" and "preferably" refer to embodiments of the technology that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the technology.

The amount of compositions described herein needed for achieving a therapeutic effect may be determined empirically in accordance with conventional procedures for the particular purpose. Generally, for administering therapeutic agents (e.g., antimethanogenic statins and/or additional therapeutic agents described herein) for therapeutic purposes, the therapeutic agents are given at a pharmacologically effective dose. A "pharmacologically effective amount," "pharmacologically effective dose," "therapeutically effective amount," or "effective amount" refers to an amount sufficient to produce the desired physiological effect or amount capable of achieving the desired result, particularly for treating the disorder or disease. An effective amount as used herein would include an amount sufficient to, for example, delay the development of a symptom of the disorder or disease, alter the course of a symptom of the disorder or disease (e.g., slow the progression of a symptom of the disease), reduce or eliminate one or more symptoms or manifestations of the disorder or disease, and reverse a symptom of a disorder or disease. Therapeutic benefit also includes halting or slowing the progression of the underlying disease or disorder, regardless of whether improvement is realized.

Effective amounts, toxicity, and therapeutic efficacy can be determined by standard pharmaceutical procedures in cell cultures, tissue samples, tissue homogenates or experimental animals, e.g., for determining the LD50 (the dose lethal to about 50% of the population) and the ED50 (the dose therapeutically effective in about 50% of the population). The dosage can vary depending upon the dosage form employed and the route of administration utilized. The dose ratio between toxic and therapeutic effects is the therapeutic index and can be expressed as the ratio LD50/ED50. In some embodiments, compositions and methods that exhibit large therapeutic indices are preferred. A therapeutically effective dose can be estimated initially from in vitro assays, including, for example, cell culture assays or measurements or methane production in stool samples. Also, a dose can be formulated in animal models to achieve a circulating plasma concentration range that includes the IC50 as determined in cell culture, or in an appropriate animal model. Levels of the described compositions in plasma can be measured, for example, by high performance liquid chromatography. The effects of any particular dosage can be monitored by a suitable bioassay. The dosage can be determined by a physician and adjusted, as necessary, to suit observed effects of the treatment.

In certain embodiments, the effect will result in a quantifiable change of at least about 10%, at least about 20%, at least about 30%, at least about 50%, at least about 70%, or at least about 90%. In some embodiments, the effect will result in a quantifiable change of about 10%, about 20%, about 30%, about 50%, about 70%, or even about 90% or more. Therapeutic benefit also includes halting or slowing the progression of the underlying disease or disorder, regardless of whether improvement is realized.

As used herein, "methods of treatment" are equally applicable to use of a composition for treating the diseases or disorders described herein and/or compositions for use and/or uses in the manufacture of a medicaments for treating the diseases or disorders described herein.

EQUIVALENTS

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

Those skilled in the art will recognize, or be able to ascertain, using no more than routine experimentation, numerous equivalents to the specific embodiments described specifically herein. Such equivalents are intended to be encompassed in the scope of the following claims.

INCORPORATION BY REFERENCE

All patents and publications referenced herein are hereby incorporated by reference in their entireties.

The publications discussed herein are provided solely for their disclosure prior to the filing date of the present application. Nothing herein is to be construed as an admission that the present invention is not entitled to antedate such publication by virtue of prior invention.

As used herein, all headings are simply for organization and are not intended to limit the disclosure in any manner. The content of any individual section may be equally applicable to all sections.

What is claimed is:

1. A pharmaceutical formulation, comprising at least two types of modified-release particles, each modified-release particle containing:
   about 5-20% by weight antimethanogenic statin;
   about 50-70% by weight microcrystalline cellulose;
   about 1-10% by weight copovidone;
   about 0.1-3.0% by weight silicon dioxide;
   about 0.1-3.0% by weight magnesium stearate;
   about 1-10% by weight crospovidone; and
   about 10-20% by weight enteric polymer,
   wherein each modified-release particle comprises about 7 mg of the antimethanogenic statin;
   wherein a first type of modified-release particle comprises a first enteric polymer that dissolves at a pH of about 5.5 and a second type of modified-release particle comprises a second enteric polymer that dissolves at a pH of about 7.0.

2. The pharmaceutical formulation of claim 1, wherein each modified-release particle contains:
   about 12% by weight antimethanogenic statin;
   about 61% by weight microcrystalline cellulose;
   about 6% by weight copovidone;
   about 2% by weight silicon dioxide;
   about 1% by weight magnesium stearate;
   about 5% by weight crospovidone; and
   about 15% by weight of the first or the second enteric polymer;
   wherein each modified-release particle comprises about 7 mg of the antimethanogenic statin.

3. The pharmaceutical formulation of claim 1, wherein the first type of modified-release particle and the second type of modified-release particle are present at a ratio of about 1:2.

4. The pharmaceutical formulation of claim 1, wherein the first type of modified-release particle and the second type of modified-release particle type are present at a ratio of about 1:5.

5. The pharmaceutical formulation of claim 1, wherein each modified-release particle is a microbead or mini-tablet.

6. The pharmaceutical formulation of claim 1, wherein the antimethanogenic statin is lovastatin.

7. The pharmaceutical formulation of claim 6, wherein the lovastatin is the lactone form.

8. The pharmaceutical formulation of claim 1, wherein the first enteric polymer releases the antimethanogenic statin into the duodenum.

9. The pharmaceutical formulation of claim 1, wherein the second enteric polymer releases the antimethanogenic statin into the ileocecal junction.

10. The pharmaceutical formulation of claim 1, wherein the formulation is a capsule or tablet.

11. The pharmaceutical formulation of claim 1, wherein the formulation is suitable for oral administration.

12. The pharmaceutical formulation of claim 1, wherein the first enteric polymer that dissolves at a pH of about 5.5 is poly(methacrylic acid-co-ethyl acrylate) 1:1.

13. The pharmaceutical formulation of claim 1, wherein the second enteric polymer that dissolves at a pH of about 7.0 is poly(methyl acrylate-co-methyl methacrylate-co-methacrylic acid) 7:3:1.

14. A pharmaceutical formulation, comprising:
   about 5-20% by weight of the antimethanogenic statin;
   about 30-60% by weight microcrystalline cellulose;
   about 1-10% by weight copovidone;
   about 0.1-3.0% by weight silicon dioxide;
   about 0.1-3.0% by weight magnesium stearate;
   about 1-10% by weight crospovidone;
   about 0.5-10% by weight a first enteric polymer that dissolves at a pH of about 5.5 and encapsulates a first type particle comprising the antimethanogenic statin;
   about 1-15% by weight a second enteric polymer that dissolves at a pH of about 7.0 and encapsulates a second type particle comprising the antimethanogenic statin;
   wherein each particle comprises about 7 mg of the antimethanogenic statin;
   wherein the first type particle and the second type particle are present in a ratio of about 1:2, such that the formulation has a unit dosage of about 21 mg.

15. The pharmaceutical formulation of claim 14, wherein the antimethanogenic statin is lovastatin.

16. The pharmaceutical formulation of claim 15, wherein the lovastatin is the lactone form.

17. A pharmaceutical formulation, comprising:
  about 5-20% by weight of the antimethanogenic statin;
  about 30-60% by weight microcrystalline cellulose;
  about 1-10% by weight copovidone;
  about 0.1-3.0% by weight silicon dioxide;
  about 0.1-3.0% by weight magnesium stearate;
  about 1-10% by weight crospovidone;
  about 0.5-10% by weight a first enteric polymer that dissolves at a pH of about 5.5 and encapsulates a first type particle comprising the antimethanogenic statin;
  about 1-15% by weight a second enteric polymer that dissolves at a pH of about 7.0 and encapsulates a second type particle comprising the antimethanogenic statin;
  wherein each particle comprises about 7 mg of the antimethanogenic statin;
  wherein the first type particle and the second type particle types are present in a ratio of about 1:5, such that the formulation has a unit dosage of about 42 mg.

18. The pharmaceutical formulation of claim 17, wherein the antimethanogenic statin is lovastatin.

19. The pharmaceutical formulation of claim 18, wherein the lovastatin is the lactone form.

20. The method of treating constipation-associated IBS (IBS-C), comprising administering an effective amount of the pharmaceutical formulation of claim 1 to a patient in need thereof.

21. The method of treating constipation-associated IBS (1138-C), comprising administering an effective amount of the pharmaceutical formulation of claim 14 to a patient in need thereof.

22. The method of treating constipation-associated IBS (1138-C), comprising administering an effective amount of the pharmaceutical formulation of claim 17 to a patient in need thereof.

* * * * *